United States Patent
Blair et al.

(10) Patent No.: US 12,312,405 B2
(45) Date of Patent: May 27, 2025

(54) ANTI-PD-1 ANTIBODIES

(71) Applicant: Boehringer Ingelheim International GmbH, Ingelheim am Rhein (DE)

(72) Inventors: David A. Blair, Sandy Hook, CT (US); Nicole K. Garaffa, Trumbull, CT (US); Pankaj Gupta, Scarsdale, NY (US); Priyanka Gupta, Newtown, CT (US); Fei Han, Acton, MA (US); Aaron Timothy Karlak, Beacon Falls, CT (US); Dongmei Liu, Oxford, CT (US); Mouhamadou Lamine Mbow, Echichens (CH); Joseph A. Mozdzierz, Mahopac, NY (US); Kerry L. M. Ralph, Bethel, CT (US); Abdulsalam Shaaban, Ridgefield, CT (US); Helen Haixia Wu, Danbury, CT (US); Guangwei Yang, Cheshire, CT (US)

(73) Assignee: Boehringer Ingelheim International GmbH

( * ) Notice: Subject to any disclaimer, the term of this patent is extended or adjusted under 35 U.S.C. 154(b) by 14 days.

(21) Appl. No.: 17/328,050

(22) Filed: May 24, 2021

(65) Prior Publication Data
US 2021/0380696 A1 Dec. 9, 2021

Related U.S. Application Data

(60) Provisional application No. 63/039,686, filed on Jun. 16, 2020, provisional application No. 63/029,962, filed on May 26, 2020.

(51) Int. Cl.
*C07K 16/28* (2006.01)
*A61K 39/00* (2006.01)

(52) U.S. Cl.
CPC ...... *C07K 16/2818* (2013.01); *C07K 16/2803* (2013.01); *A61K 2039/505* (2013.01); *C07K 2317/24* (2013.01); *C07K 2317/31* (2013.01); *C07K 2317/75* (2013.01); *C07K 2317/92* (2013.01)

(58) Field of Classification Search
CPC ............ C07K 16/2818; C07K 16/2803; C07K 2317/24; C07K 2317/31; C07K 2317/75; C07K 2317/92; A61K 2039/505
See application file for complete search history.

(56) References Cited

U.S. PATENT DOCUMENTS

| | | |
|---|---|---|
| 4,179,337 A | 12/1979 | Davis et al. |
| 4,275,149 A | 6/1981 | Litman et al. |
| 4,301,144 A | 11/1981 | Iwashita et al. |
| 4,318,980 A | 3/1982 | Boguslaski et al. |
| 4,419,446 A | 12/1983 | Howley et al. |
| 4,496,689 A | 1/1985 | Mitra |
| 4,560,655 A | 12/1985 | Baker |
| 4,601,978 A | 7/1986 | Karin |
| 4,640,835 A | 2/1987 | Shimizu et al. |
| 4,657,866 A | 4/1987 | Kumar |
| 4,670,417 A | 6/1987 | Iwasaki et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,888,809 A | 3/1999 | Allison |
| 6,037,454 A | 3/2000 | Jardieu et al. |
| 6,054,297 A | 4/2000 | Carter et al. |
| 6,407,213 B1 | 6/2002 | Carter et al. |
| 6,737,056 B1 * | 5/2004 | Presta ............... C07K 16/18 530/387.3 |
| 10,414,821 B2 | 9/2019 | Liu |
| 2011/0008369 A1 | 1/2011 | Finnefrock et al. |
| 2011/0229461 A1 | 9/2011 | Tyson |
| 2012/0076790 A1 | 3/2012 | Classon et al. |
| 2017/0088618 A1 | 3/2017 | Bennett et al. |
| 2020/0165630 A1 * | 5/2020 | Paul ............... C12N 15/86 |
| 2023/0272076 A1 | 8/2023 | Bennett et al. |
| 2023/0272106 A1 | 8/2023 | Hu et al. |

FOREIGN PATENT DOCUMENTS

| | | |
|---|---|---|
| CN | 105330740 A | 2/2016 |
| CN | 107840887 A | 3/2018 |
| CN | 110167967 A | 8/2019 |
| CN | 110577599 A | 12/2019 |
| CN | 110734493 A | 1/2020 |
| CN | 111956799 A | 11/2020 |
| DE | 266710 A3 | 4/1989 |
| EP | 73657 A1 | 3/1983 |
| EP | 183070 A2 | 6/1986 |

(Continued)

OTHER PUBLICATIONS

Philips et al., Therapeutic uses of anti-PD-1 and anti-PD-L1 antibodies, 2014, International Immunology 27 (1): 39-46 (Year: 2014).*
Davies et al., Human IgG4: a structural perspective, 2015, Immunological Reviews 2015 vol. 268: 139-159 (Year: 2015).*
Kimura et al., Myasthenic crisis and polymyositis induced by one dose of nivolumab, 2016, Cancer Sci 107: 1055-1058 (Year: 2016).*
Le Burel et al., Prevalence of immune-related systemic adverse events in patients treated with anti-Programmed cell Death 1/anti-Programmed cell Death-Ligand 1 agents: A single-centre pharmacovigilance database analysis, 2017, European Journal of Cancer 82: 34-44 (Year: 2017).*

(Continued)

*Primary Examiner* — Vanessa L. Ford
*Assistant Examiner* — Danaya L Middleton
(74) *Attorney, Agent, or Firm* — Shelley A. Jones

(57) ABSTRACT

The present invention relates to new anti-PD-1 (Programmed cell death 1) antibodies and antigen-binding fragments thereof for therapeutic and diagnostic methods and compositions using them.

86 Claims, 14 Drawing Sheets
Specification includes a Sequence Listing.

(56) References Cited

FOREIGN PATENT DOCUMENTS

| | | |
|---|---|---|
| EP | 244234 A2 | 11/1987 |
| EP | 402226 A1 | 12/1990 |
| JP | 2013542194 A | 11/2013 |
| WO | 1987000195 A1 | 1/1987 |
| WO | 1990003430 A1 | 4/1990 |
| WO | 1990013646 A1 | 11/1990 |
| WO | 1994011026 A2 | 5/1994 |
| WO | 1996032478 A1 | 10/1996 |
| WO | 0114557 A1 | 3/2001 |
| WO | 02078731 A1 | 10/2002 |
| WO | 03011911 A1 | 2/2003 |
| WO | 2004056875 A1 | 7/2004 |
| WO | 2004072286 A1 | 8/2004 |
| WO | 2005077042 A2 | 8/2005 |
| WO | 2006121168 A1 | 11/2006 |
| WO | 2009026472 A1 | 2/2009 |
| WO | 2009067812 A1 | 6/2009 |
| WO | 2010029434 A1 | 3/2010 |
| WO | 2010029435 A1 | 3/2010 |
| WO | 2010036959 A2 | 4/2010 |
| WO | 2011110604 A1 | 9/2011 |
| WO | 2011110621 A1 | 9/2011 |
| WO | 2012092374 A2 | 7/2012 |
| WO | 2013022091 A1 | 2/2013 |
| WO | 2014179664 A2 | 11/2014 |
| WO | 2014206107 A1 | 12/2014 |
| WO | 2015036394 A1 | 3/2015 |
| WO | 2015112800 A1 | 7/2015 |
| WO | 2015112805 A1 | 7/2015 |
| WO | 2015112900 A1 | 7/2015 |
| WO | 2016020856 A2 | 2/2016 |
| WO | 2016106159 A1 | 6/2016 |
| WO | 2016210129 A1 | 12/2016 |
| WO | 2017016497 A1 | 2/2017 |
| WO | 2017055443 A1 | 4/2017 |
| WO | 2017055547 A1 | 4/2017 |
| WO | 2017058859 A1 | 4/2017 |
| WO | 2017079080 A1 | 5/2017 |
| WO | 2017087599 A1 | 5/2017 |
| WO | 2017124050 A1 | 7/2017 |
| WO | 2017211321 A1 | 12/2017 |
| WO | 2018013017 A1 | 1/2018 |
| WO | 2018050027 A1 | 3/2018 |
| WO | 2018053401 A1 | 3/2018 |
| WO | 2018053405 A1 | 3/2018 |
| WO | 2018053709 A1 | 3/2018 |
| WO | 2018085358 A1 | 5/2018 |
| WO | 2018085468 A1 | 5/2018 |
| WO | 2018091661 A1 | 5/2018 |
| WO | 2018113258 A1 | 6/2018 |
| WO | 2018/136553 A | 7/2018 |
| WO | 2018127709 A1 | 7/2018 |
| WO | 2018127710 A1 | 7/2018 |
| WO | 2018127711 A1 | 7/2018 |
| WO | 2018129559 A1 | 7/2018 |
| WO | 2018133837 A1 | 7/2018 |
| WO | 2018137576 A1 | 8/2018 |
| WO | 2018183459 A1 | 10/2018 |
| WO | 2018187057 A1 | 10/2018 |
| WO | 2018204368 A1 | 11/2018 |
| WO | 2018223923 A1 | 12/2018 |
| WO | 2018226580 A2 | 12/2018 |
| WO | 2019028316 A1 | 2/2019 |
| WO | 2019140196 A1 | 7/2019 |
| WO | 2019168745 A1 | 9/2019 |
| WO | 2019170885 A1 | 9/2019 |
| WO | 2019170898 A1 | 9/2019 |
| WO | 2019171253 A1 | 9/2019 |
| WO | 2019179390 A1 | 9/2019 |
| WO | 2019179391 A1 | 9/2019 |
| WO | 2019179396 A1 | 9/2019 |
| WO | 2019179421 A1 | 9/2019 |
| WO | 2019179434 A1 | 9/2019 |
| WO | 2019219064 A1 | 11/2019 |
| WO | 2020015722 A1 | 1/2020 |
| WO | 2020097141 A1 | 5/2020 |
| WO | 2020116636 A1 | 6/2020 |
| WO | 2020204152 A1 | 10/2020 |
| WO | 2020247648 A2 | 12/2020 |
| WO | 21011448 A1 | 1/2021 |
| WO | 21025140 A1 | 2/2021 |
| WO | 21034890 A1 | 2/2021 |
| WO | 21121373 A1 | 6/2021 |
| WO | 21123202 A1 | 6/2021 |
| WO | 21139642 A1 | 7/2021 |
| WO | 2021154027 A1 | 8/2021 |
| WO | 2021196443 A1 | 10/2021 |
| WO | 2021241523 A1 | 12/2021 |
| WO | 2021242663 A1 | 12/2021 |
| WO | 2021249551 A1 | 12/2021 |
| WO | 2021254447 A1 | 12/2021 |

OTHER PUBLICATIONS

Lo et al., Effector-attenuating Substitutions That Maintain Antibody Stability and Reduce Toxicity in Mice, 2017, The Journal of Biological Chemistry vol. 292, No. 9, pp. 3900-3908 (Year: 2017).*
Hanna, Review of PD-1-Induced Myositis and a Case of Pembrolizumab-Induced Myositis in a Patient with Metastatic Melanoma, 2018, J Hematol Oncol Pharm. 8(4):166-170 (Year: 2018).*
Kreuter et al., Nivolumab-Associated Giant Cell Arteritis With Scalp Necrosis, 2019, JAMA Dermatology Sep. 2019 vol. 155, No. 9: 1086-1087 (Year: 2019).*
Zhang et al., The PD-1/PD-L pathway in rheumatic diseases, 2021, Journal of the Formosan Medical Association 120, 48-59 (Year: 2021).*
Adamczyk et al., PD1/PD-L1 pathway in psoriasis and psoriatic arthritis: a review, 2021, Adv Dermatol Allergol 2021; XXXVIII (6): 925-930 (Year: 2021).*
Fife et al., Ann. N.Y. Acad. Sci. 1217 (2011) 45-59 (Year: 2011).*
Zamani et al., Cellular Immunology 310 (2016) 27-41 (Year: 2016).*
Weyand et al., J Leukoc Biol. 2018;103:565-575 (Year: 2018).*
Heppner et al., Tumor heterogeneity: biological implications and therapeutic consequences, 1983, Cancer Metastasis Reviews 2: 5-23 (Year: 1983).*
Abstract in English for CN107840887, dated Mar. 27, 2018.
Abstract in English for CN110577599, dated Dec. 17, 2019.
Abstract in English for CN111956799, dated Nov. 20, 2020.
Abstract in English for WO2018223923, dated Dec. 13, 2018.
Abstract in English for WO2020204152, dated Oct. 8, 2020.
Abstract in English for WO2021154027, dated Aug. 5, 2021.
Abstract in English for WO2021196443, dated Jul. 20, 2021.
Abstract in English for WO2021241523, dated Dec. 2, 2021.
Abstract in English for WO2021249551, dated Dec. 16, 2021.
International Search Report and Written Opinion for corresponding application, PCT/US2021/033823, dated Nov. 9, 2021.
Yu et al., "Reducing affinity as a strategy to boost immunomodulatory antibody agonism", Nature, 2023, pp. 1-33.
Abdiche et al., "High-Throughput Epitope Binning Assays on Label-Free Array-Based Biosensors Can Yield Exquisite Epitope Discrimination That Facilitates the Selection of Monoclonal Antibodies with Functional Activity", PLOS ONE, 2014, vol. 9, No. 3, pp. e92451.
Almagro et al., "Antibody modeling assessment", Proteins: Structure, Function, and Bioinformatics, 2011, vol. 79, No. 11, pp. 3050-3066.
Almagro et al., "Humanization of antibodies.", Frontiers in Bioscience ?: A Journal and Virtual Ibrary, 2008, vol. 13, pp. 1619-1633.
Altschul et al., "Basic local alignment search tool", Journal of Molecular Biology, 1990, vol. 215, No. 3, pp. 403-410.
Altschul et al., "Gapped BLAST and PSI-BLAST: a new generation of protein database search programs", Nucleic Acids Research, 1997, vol. 25, No. 17, pp. 3389-3402.
Baghban et al., "Yeast Expression Systems: Overview and Recent Advances", Molecular Biotechnology, 2019, vol. 61, No. 5, pp. 365-384.

(56) References Cited

OTHER PUBLICATIONS

Brennan et al., "Preparation of Bispecific Antibodies by Chemical Recombination of Monoclonal Immunoglobulin G1 Fragments", Science, 1985, vol. 229, No. 4708, pp. 81-83.
Brown et al., "Assessing the binding properties of the anti-PD-1 antibody landscape using label-free biosensors", PLOS ONE, 2020, vol. 15, No. 3, pages e0229206.
CAS No. 2412764-40-8. Retrieved from the internet Feb. 9, 2023: https://www.biochempartner.com/reference-1834871.
Chothia et al., "Canonical structures for the hypervariable regions of immunoglobulins", Journal of Molecular Biology, 1987, vol. 196, No. 4, pp. 901-917.
Chothia et al., "Domain association in immunoglobulin molecules The packing of variable domains", Journal of Molecular Biology, 1985, vol. 186, No. 3, pp. 651-663.
Clackson et al., "Making antibody fragments using phage display libraries", Nature, 1991, vol. 352, No. 6336, pp. 624-628.
Edge et al., "Deglycosylation of glycoproteins by trifluoromethanesulfonic acid", Analytical Biochemistry, 1981, vol. 118, No. 1, pp. 131-137.
Guss et al., "Structure of the IgG?binding regions of streptococcal protein G.", The EMBO Journal, 1986, vol. 5, No. 7, pp. 1567-1575.
Ham et al., "Media and growth requirements", Methods in Enzymology, 1979, vol. 58, pp. 44-93.
Higgins et al., "Using CLUSTAL for multiple sequence alignments", Methods in Enzymology, 1996, vol. 266, pp. 383-402.
Jones, "Proteinase Mutants of Saccharomyces Cerevisiae", Genetics, 1977, pp. 23-33.
Karlin et al., "Applications and statistics for multiple high-scoring segments in molecular sequences.", Proceedings of the National Academy of Sciences, 1993, vol. 90, No. 12, pp. 5873-5877.
Kohler et al., "Continuous cultures of fused cells secreting antibody of predefined specificity", Nature, 1975, vol. 256, pp. 495-497.
Lindmark et al., "Binding of immunoglobulins to protein A and immunoglobulin levels in mammalian sera", Journal of Immunological Methods, 1983, vol. 62, No. 1, pp. 1-13.
Maier et al., "Assessment of fully automated antibody homology modeling protocols in molecular operating environment", Proteins: Structure, Function, and Bioinformatics, 2014, vol. 82, No. 8, pp. 1599-1610.
Marks et al., "By-passing immunization Human antibodies from V-gene libraries displayed on phage", Journal of Molecular Biology, 1991, vol. 222, No. 3, pp. 581-597.
Mather et al., "Culture of Testicular Cells in Hormone Supplemented Serum Free Medium*", Annals of the New York Academy of Sciences, 1982, vol. 383, No. 1, pp. 44-68.
Mather, "Establishment and Characterization of Two Distinct Mouse Testicular Epithelial Cell Line", Biology of Reproduction, 1980, vol. 23, No. 1, pp. 243-252.
Morimoto et al., "Single-step purification of F(ab)2 fragments of mouse monoclonal antibodies (immunoglobulins G1) by hydrophobic interaction high performance liquid chromatography using TSKgel Phenyl-5PW", Journal of Biochemical and Biophysical Methods, 1992, vol. 24, No. 1-2, pp. 107-117.
Morrison et al., "Chimeric human antibody molecules: mouse antigen-binding domains with human constant region domains.", Proceedings of the National Academy of Sciences, 1984, vol. 81, No. 21, pp. 6851-6855.
Carter et al., "High Level *Escherichia coli* Expression and Production of a Bivalent Humanized Antibody Fragment", Bio/Technology, 1992, vol. 10, No. 2, pp. 163-167.
Fleer et al., "Stable multicopy vectors for high-level secretion of recombinant human serum albumin by Kluyveromyces yeasts", Bio/Technology, 1991, vol. 9, pp. 968-975.
Myers et al., "Approximate matching of regular expressions", Bulletin of Mathematical Biology, 1989, vol. 51, No. 1, pp. 5-37.
O'Sullivan et al., "Methods for the preparation of enzyme-antibody conjugates for use in enzyme immunoassay", Methods in Enzymology, 1981, vol. 73, pp. 147-166.
Paluch et al., "Immune Checkpoints as Therapeutic Targets in Autoimmunity", Frontiers in Immunology, 2018, vol. 9, Article 2306, pp. 1-11.
Pearson et al., "Improved tools for biological sequence comparison", Proceedings of the National Academy of Sciences USA, 1988, vol. 85, No. 8, pp. 2444-2448.
Reyes et al., "Expression of human B-interferon cDNA under the control of a thymidine kinase promoter from herpes simplex virus", Nature, 1982, vol. 297, No. 5867, pp. 598-601.
Sojar et al., "A chemical method for the deglycosylation of proteins", Archives of Biochemistry and Biophysics, 1987, vol. 259, No. 1, pp. 52-57.
Stinchcomb et al., "Isolation and characterization of a yeast chromosomal replicator", Nature, 1979, vol. 282, pp. 39-43.
Thotakura et al., "Enzymatic deglycosylation of glycoproteins", Methods in Enzymology, 1987, vol. 138, pp. 350-359.
Urlaub et al., "Isolation of Chinese hamster cell mutants deficient in dihydrofolate reductase activity", Proceedings of the National Academy of Sciences, 1980, vol. 77, No. 7, pp. 4216-4220.
Van Den Berg et al., "Kluyveromyces as a host for heterologous gene expression: expression and secretion of prochymosin", Bio/Technology, 1990, vol. 8, pp. 135-139.
Vargas-Madrazo et al., "An improved model of association for VH-VL immunoglobulin domains: Asymmetries between VH and VL in the packing of some interface residues", Journal of Molecular Recognition, 2003, vol. 16, No. 3, pp. 113-120.
Zapata et al., "Engineering linear F(ab')2 fragments for efficient production in *Escherichia coli* and enhanced antiproliferative activity", "Protein Engineering, Design and Selection," 1995, vol. 8, No. 10, pp. 1057-1062.
Zola et al., "Using Monoclonal Antibodies: Soluble Antigens", in "Monoclonal Antibodies: A Manual of Techniques", CRC Press Inc., 1987, chapter 6, pp. 147-158.
Abstract in English for JP2013542194, dated Nov. 21, 2013.
Altshuler et al., Uspekhi Biologicheskoi Khimii, 2010, vol. 50, pp. 203-258. [English language version cited as NPL Reference No. 3].
Altshuler et al., "Generation of Recombinant Antibodies and Means for Increasing Their Affinity," Biochemistry (Moscow), 2010, vol. 75, No. 13, pp. 1584-1605 [English language version of Altshuler et al., Uspekhi Biologicheskoi Khimii, 2010, vol. 50, pp. 203-258].
Machine translation in English of CN110734493.

* cited by examiner

ID NO: 49 (H-CDR3), and

SEQUENCE LISTING

<160> NUMBER OF SEQ ID NOS: 167

<210> SEQ ID NO 1
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Lys Ser Leu Leu His Arg Asn Gly Ile Thr Tyr Leu Tyr
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Met Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gln Asn Leu Glu Phe Pro Leu Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ser Gln Asn Val Gly Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Val Ser Asn Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Tyr Ser Ser Tyr Pro Phe Thr
```

```
<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ala Ser Gln Gly Ile Asn Asn Asn Ile Gly
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Lys Ser Asn Leu Glu Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Gln Tyr Ala Gln Phe Pro Tyr Thr
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ser Lys Ser Leu Leu His Arg Asn Gly Ile Thr Tyr Leu Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Met Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 12

Ala Gln Asn Leu Glu Leu Pro Leu Thr
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Ser Gln Ser Leu Leu Tyr Ser Ser Asn Gln Lys Asn Tyr Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ala Ser Thr Arg Glu Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gln Tyr Tyr Ser Ser Pro Leu Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Gln Glu Ile Ser Gly Tyr Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ser Thr Leu Asp Ser
1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gln Tyr Ala Ser Tyr Pro Leu Thr
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ala Asn Ser Ser Val Ser Phe Met His
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Thr Ser Ser Leu Ala Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Arg Ser Ser Tyr Pro Leu Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Ser Gln Asn Val Val Thr Tyr Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Ser Ala Ser Tyr Arg Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr His Ser Tyr Pro Tyr Thr
1               5

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Glu Ser Val Asp Ile Tyr Gly Ile Ser Phe Leu His
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser Asn Leu Asp Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Ser Asn Lys Asp Pro Leu Thr
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Ser Ser Gln Ser Leu Leu Tyr Ser Ser Asn Gln Lys Ile Tyr Leu
1               5                   10                  15

Ala

<210> SEQ ID NO 29
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Tyr Tyr Asn Ser Pro Leu Thr
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ala Ser Ser Ser Ile Ser Ser Asp Tyr Leu His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Thr Ser Asn Leu Ala Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Gly Thr Ser Leu Pro Arg Ala
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Ser Ser Gln Ser Leu Leu His Ser Gly Asn Gln Lys Asn Tyr Met
1               5                   10                  15

Thr

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

Gln Asn Asp Tyr Ser Tyr Pro Leu Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Ala Ser Thr Leu Asp Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Gln Tyr Ala Asn Tyr Pro Tyr Thr
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ala Ser Gln Asp Ile Ile Asn Tyr Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Thr Ser Ser Leu His Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Gln Tyr Ser Gln Leu Pro Tyr Thr
1               5

<210> SEQ ID NO 40
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 40

Ser Ala Ser Gln Asp Ile Phe Asn Tyr Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Thr Ser Ser Leu His Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Tyr Ser Asn Leu Pro Tyr Thr
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Tyr Thr Phe Thr Asp Tyr Tyr Val Asn
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ile His Pro Asn Ser Gly Asp Thr Thr Tyr Asn Gln Lys Phe Lys
1               5                   10                  15

Asp

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

```
Arg Arg Tyr Asp Tyr Asp Gly Phe Ala Tyr
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ile His Pro Asn Asn Gly Gly Ile Thr Tyr Asn Gln Lys Phe Lys
1               5                   10                  15

Gly

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Thr Phe Ser Asp Tyr Gly Met His
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ile Asn Ser Asp Ser Asn Thr Ile Tyr Tyr Ala Asp Thr Val Lys
1               5                   10                  15

Gly

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Val Ala Pro Asp Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly His Thr Phe Thr Ser Asn Trp Ile His
1               5                   10

<210> SEQ ID NO 51
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Ile Asp Pro Ser Asp Ser Tyr Thr Tyr Tyr Asn Gln Lys Phe Lys
1               5                   10                  15
Gly

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Arg Asn Ser Asn Phe Ala Tyr
1               5

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Phe Ser Leu Ser Thr Ser Gly Met Gly Val Thr
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Ile Phe Trp Asp Gly Asp Lys Arg Tyr Asn Pro Ser Leu Lys Ser
1               5                   10                  15

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Tyr Tyr Phe Asp Tyr Gly Tyr Ala Ile Asp Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Gly Tyr Thr Phe Thr Ser Tyr Val Ile His
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Ile Asp Pro Ser Asn Asp Asp Thr Lys Tyr Asn Glu Lys Phe Lys
1               5                   10                  15

Gly

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Ala Tyr Tyr Gly Gly Leu Tyr Gly Met Asp Tyr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Tyr Thr Phe Ile Asp Tyr Thr Ile His
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Ile Phe Pro Gly Ser Thr Asn Asp Thr Lys Tyr Asn Asp Lys Phe
1               5                   10                  15

Lys Gly

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Tyr Arg Thr Asp Phe Asp Tyr
1               5
```

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Tyr Ser Phe Thr Ser Tyr Trp Met His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ile Asp Pro Ser Asn Ser Tyr Ala Tyr His Ser Gln Lys Phe Lys
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Asp Gly Thr Ser His Trp Tyr Phe Asp Val
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Tyr Thr Phe Thr Asp Tyr Tyr Leu Asn
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Ile Tyr Pro Gly Ser Ser Asp Thr Lys His Asn Glu Asn Phe Lys
1               5                   10                  15

Gly

<210> SEQ ID NO 67
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 67

Tyr Ser Asn Phe Phe Phe Asp Tyr
1               5

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Ser Leu Ser Thr Ser Gly Met Gly Val Ser
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

His Ile Tyr Trp Asp Asp Asp Lys Arg Tyr Asn Pro Ser Leu Lys Ser
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ser Gln Gly Leu Tyr Ser Ser Tyr Asp Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Tyr Thr Phe Thr Ser Tyr Val Met His
1               5                   10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Ile Asp Pro Asp Asn Asp Gly Thr Lys Tyr Asn Glu Lys Phe Lys
1               5                   10                  15
```

Gly

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Thr Phe Ser Asp Tyr Tyr Met Ser
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Ile Ser Ser Gly Gly Gly Ser Ser Tyr Tyr Pro Asp Ser Val Lys
1               5                   10                  15

Gly

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Pro His Tyr Phe Ala Met Asp Cys
1               5

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Ile Ser Ser Gly Gly Gly Ser Lys Tyr Tyr Pro Asp Leu Val Lys
1               5                   10                  15

Gly

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Pro His Tyr Phe Ala Met Asp Tyr
1               5

<210> SEQ ID NO 78
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Ile Ser Ser Gly Gly Gly Ser Ser Tyr Tyr Pro Asp Ala Val Lys
1               5                   10                  15

Gly

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Ile Ser Ser Gly Gly Gly Ser Ser Tyr Tyr Pro Asp Leu Val Lys
1               5                   10                  15

Gly

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Thr Phe Ser Asp Tyr Tyr Met Ala
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asn Ile Asn Tyr Asp Gly Phe Asn Thr Tyr Tyr Leu Asp Ser Leu Lys
1               5                   10                  15

Ser

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Tyr Trp Ser Leu Tyr Phe Asp Tyr
1               5                   10

<210> SEQ ID NO 83
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 83

Gly Tyr Thr Phe Thr Asp Tyr Tyr Ile Asn
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ile Tyr Pro Gly Gly Gly His Thr Lys Tyr Asn Glu Lys Phe Lys
1               5                   10                  15

Gly

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Ser Asn Tyr Tyr Phe Asp Phe
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Tyr Thr Phe Thr Ser Tyr Tyr Ile Gln
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Ile Tyr Pro Gly Asp Gly Thr Thr Asn Tyr Asn Glu Asn Phe Lys
1               5                   10                  15

Gly

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

```
<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

Tyr Gly Leu Val Pro Phe Asp Tyr
1               5

Gly Asn Thr Phe Asn Ser Asn Tyr Ile Gln
1               5                   10

```
<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

Trp Ile Tyr Pro Gly Asp Gly Ser Thr Asn Tyr Ser Glu Lys Phe Lys
1               5                   10                  15

Gly

```
<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Tyr Gly Pro Val Pro Phe Asp Tyr
1               5

```
<210> SEQ ID NO 92
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92
```

Glu Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Glu Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Gly Gln Asn
                85                  90                  95

Leu Glu Phe Pro Leu Thr Phe Gly Ala Gly Thr Lys Leu Glu Leu Lys
            100                 105                 110

<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Glu Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Glu Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Gln Gln Asn
                85                  90                  95

Leu Glu Phe Pro Leu Thr Phe Gly Ala Gly Thr Lys Leu Glu Leu Lys
            100                 105                 110

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Val Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Phe
                85                  90                  95

Thr Phe Gly Ala Gly Thr Lys Leu Glu Leu Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Asn Asn Asn

```
              20                  25                  30
Ile Gly Trp Leu Gln Gln Lys Pro Gly Lys Ser Phe Lys Gly Leu Ile
            35                  40                  45

Tyr His Lys Ser Asn Leu Glu Asp Gly Val Pro Ser Arg Phe Ser Gly
 50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Tyr
                85                  90                  95

Thr Phe Gly Gly Gly Thr Lys Leu Glu Ile Lys
            100                 105

<210> SEQ ID NO 96
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Val Met Thr Gln Ala Ala Phe Tyr Asn Pro Val Thr Leu Gly
 1               5                  10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Ala Asp Phe Thr Leu Arg Ile
 65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110

<210> SEQ ID NO 97
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Ser Gln Ser Pro Ser Ser Leu Ala Val Ser Val Gly
 1               5                  10                  15

Glu Lys Val Thr Met Thr Cys Lys Ser Ser Gln Ser Leu Leu Tyr Ser
            20                  25                  30

Ser Asn Gln Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys His Gln
                85                  90                  95

Tyr Tyr Ser Ser Pro Leu Thr Phe Gly Ala Gly Thr Lys Leu Glu Leu
```

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
            100                 105

<210> SEQ ID NO 99
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Ile Val Leu Thr Gln Ser Pro Gly Ile Met Ser Ala Ser Pro Gly
1               5                   10                  15

Glu Lys Val Thr Ile Thr Cys Ser Ala Asn Ser Ser Val Ser Phe Met
            20                  25                  30

His Trp Phe Gln Gln Lys Pro Gly Thr Ser Pro Lys Ile Trp Ile Tyr
        35                  40                  45

Ser Thr Ser Ser Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Asp Ile Val Met Thr Gln Ser Gln Lys Phe Leu Ser Thr Ser Val Gly
1               5                   10                  15

Asp Arg Val Arg Val Thr Cys Lys Ala Ser Gln Asn Val Thr Tyr
                20                  25                  30

Val Ala Trp Tyr Gln Gln Lys Pro Gly Gln Ser Pro Lys Ser Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Tyr Phe Thr Leu Thr Ile Asn Asn Val Gln Phe
65                  70                  75                  80

Glu Asp Leu Ala Glu Tyr Phe Cys Gln Gln Tyr His Ser Tyr Pro Tyr
                85                  90                  95

Thr Phe Gly Gly Gly Thr Lys Leu Glu Ile Lys
                100                 105
```

```
<210> SEQ ID NO 101
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ile Tyr
                20                  25                  30

Gly Ile Ser Phe Leu His Trp Tyr Gln Gln Lys Pro Gly Gln Pro Pro
            35                  40                  45

Lys His Leu Ile Tyr Arg Ala Ser Asn Leu Asp Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
                100                 105                 110
```

```
<210> SEQ ID NO 102
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Ser Gln Ser Pro Ser Ser Leu Thr Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Ile Tyr Leu Ala Trp Phe Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

-continued

Ile Ser Ser Val Lys Ala Glu Asp Leu Ala Val Tyr Tyr Cys Gln Gln
                85                  90                  95

Tyr Tyr Asn Ser Pro Leu Thr Phe Gly Ala Gly Thr Lys Leu Glu Leu
            100                 105                 110

Lys

<210> SEQ ID NO 103
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asp
            20                  25                  30

Tyr Leu His Trp Tyr Gln Gln Lys Pro Gly Phe Ser Pro Glu Leu Leu
            35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Ser Met Glu
65                  70                  75                  80

Ala Glu Asp Val Ala Thr Tyr Tyr Cys Gln Gln Gly Thr Ser Leu Pro
                85                  90                  95

Arg Ala Phe Gly Gly Gly Thr Lys Leu Glu Ile Lys
            100                 105

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu His Ser
            20                  25                  30

Gly Asn Gln Lys Asn Tyr Met Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 105
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 105

Asp Ile Gln Met Thr Gln Ser Pro Ser Ser Leu Ser Ala Ser Pro Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Val Ala Ser Thr Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Asn Tyr Pro Tyr
                85                  90                  95

Thr Phe Gly Gly Gly Thr Lys Leu Glu Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Ile Asn Tyr
            20                  25                  30

Leu Asn Trp Tyr Gln Gln Lys Pro Asp Gly Thr Val Lys Leu Leu Ile
        35                  40                  45

Tyr Ser Thr Ser Ser Leu His Ser Gly Val Ser Leu Arg Phe Ser Gly
50                  55                  60

Ser Gly Ser Gly Thr Asp Tyr Ser Leu Thr Ile Ser Asn Leu Glu Pro
65                  70                  75                  80

Glu Asp Val Ala Thr Tyr Tyr Cys His Gln Tyr Ser Gln Leu Pro Tyr
                85                  90                  95

Thr Phe Gly Gly Gly Thr Lys Leu Glu Ile Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Phe Asn Tyr
            20                  25                  30

Leu Asn Trp Tyr Gln Gln Lys Pro Asp Gly Thr Val Lys Leu Leu Ile
        35                  40                  45
```

```
Tyr Tyr Thr Ser Ser Leu His Ser Gly Val Pro Ser Arg Phe Ser Gly
    50                  55                  60

Ser Gly Ser Gly Thr Asp Phe Ser Leu Thr Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys
            100                 105
```

<210> SEQ ID NO 108
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Glu Val Gln Leu Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
                20                  25                  30

Tyr Val Asn Trp Val Lys Gln Ser His Gly Lys Ser Leu Glu Trp Phe
            35                  40                  45

Gly Asp Ile His Pro Asn Ser Gly Asp Thr Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Tyr Asp Tyr Asp Gly Phe Ala Tyr Trp Gly Gln Gly
            100                 105                 110

Thr Leu Val Thr Val Ser Ala
        115
```

<210> SEQ ID NO 109
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Val Asn Trp Val Lys Gln Ser His Gly Lys Ser Leu Glu Trp Phe
            35                  40                  45

Gly Asp Ile His Pro Asn Asn Gly Gly Ile Thr Tyr Asn Gln Lys Phe
    50                  55                  60

Lys Gly Lys Ala Ser Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Tyr Asp Tyr Asp Gly Phe Ala Tyr Trp Gly Gln Gly
            100                 105                 110
```

```
Thr Leu Val Thr Val Ser Ala
        115

<210> SEQ ID NO 110
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Thr Pro Glu Lys Gly Leu Glu Trp Ile
        35                  40                  45

Ala Tyr Ile Asn Ser Asp Ser Asn Thr Ile Tyr Tyr Ala Asp Thr Val
    50                  55                  60

Lys Gly Arg Phe Thr Ile Ser Arg Asp Asn Ala Arg Lys Thr Leu Tyr
65                  70                  75                  80

Leu Gln Met Thr Ser Leu Arg Ser Glu Asp Thr Ala Met Tyr Tyr Cys
                85                  90                  95

Ser Pro Leu Val Ala Pro Asp Tyr Trp Gly Gln Gly Thr Thr Leu Thr
            100                 105                 110

Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Gln Gln Pro Gly Ala Glu Leu Val Lys Pro Gly Ala
1               5                   10                  15

Ser Val Lys Leu Ser Cys Lys Ala Ser Gly His Thr Phe Thr Ser Asn
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Ser Cys
                85                  90                  95

Ala Cys Pro Gly Arg Asn Ser Asn Phe Ala Tyr Trp Gly Gln Gly Thr
            100                 105                 110

Thr Leu Thr Val Ser Ser
        115

<210> SEQ ID NO 112
<211> LENGTH: 122
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 112

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Thr Trp Ile Arg Lys Pro Ser Gly Gln Gly Leu Glu
        35                  40                  45

Trp Leu Ala His Ile Phe Trp Asp Gly Asp Lys Arg Tyr Asn Pro Ser
    50                  55                  60

Leu Lys Ser Arg Leu Thr Ile Ser Lys Asp Ser Ser Ser Asn Gln Val
65                  70                  75                  80

Phe Leu Met Ile Thr Gly Val Gly Thr Ala Asp Ala Ala Thr Tyr Tyr
                85                  90                  95

Cys Ala Arg Tyr Tyr Tyr Phe Asp Tyr Gly Tyr Ala Ile Asp Tyr Trp
            100                 105                 110

Gly Gln Gly Thr Ser Val Thr Val Ser Ser
        115                 120

<210> SEQ ID NO 113
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Ile Asp Pro Ser Asn Asp Asp Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Ala Tyr Tyr Gly Gly Leu Tyr Gly Met Asp Tyr Trp Gly
            100                 105                 110

Gln Gly Thr Ser Val Thr Val Ser Ser
        115                 120

<210> SEQ ID NO 114
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Ile Asp Tyr

```
                    20                  25                  30
Thr Ile His Trp Val Lys Gln Ser Pro Gly Gln Gly Leu Glu Trp Ile
            35                  40                  45

Gly Trp Ile Phe Pro Gly Ser Thr Asn Asp Thr Lys Tyr Asn Asp Lys
    50                  55                  60

Phe Lys Gly Lys Ala Thr Met Thr Ala Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Tyr Arg Thr Asp Phe Asp Tyr Trp Gly Gln Gly Thr Thr
            100                 105                 110

Leu Thr Val Ser Ser
        115

<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Arg Gln Arg Pro Gly Gln Gly Leu Glu Trp Ile
        35                  40                  45

Gly Asp Ile Asp Pro Ser Asn Ser Tyr Ala Tyr His Ser Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Asp Gly Thr Ser His Trp Tyr Phe Asp Val Trp Gly Ala
            100                 105                 110

Gly Thr Ala Val Thr Val Ser Ser
        115                 120

<210> SEQ ID NO 116
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Leu Asn Trp Val Lys Gln Arg Pro Gly His Gly Leu Glu Trp Ile
        35                  40                  45

Gly Trp Ile Tyr Pro Gly Ser Ser Asp Thr Lys His Asn Glu Asn Phe
    50                  55                  60

Lys Gly Lys Ala Thr Leu Thr Val Asp Thr Tyr Ser Ser Thr Ala Tyr
```

```
                65                  70                  75                  80
Met Gln Leu Gly Ser Leu Thr Ser Glu Asp Ser Ala Val Tyr Phe Cys
                    85                  90                  95

Thr Arg Tyr Ser Asn Phe Phe Asp Tyr Trp Gly Gln Gly Thr Thr
                100                 105                 110

Leu Thr Val Ser Ser
        115
```

<210> SEQ ID NO 117
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Thr His Ile Tyr Trp Asp Asp Asp Lys Arg Tyr Asn Pro Ser
        50                  55                  60

Leu Lys Ser Arg Leu Thr Ile Ser Lys Asp Thr Ser Arg Asn Gln Val
65                  70                  75                  80

Phe Leu Glu Ile Thr Ser Val Asp Thr Ala Asp Thr Ala Thr Tyr Phe
                85                  90                  95

Cys Ala Arg Ser Ser Gln Gly Leu Tyr Ser Ser Tyr Asp Tyr Trp Gly
                100                 105                 110

Gln Gly Thr Thr Leu Thr Val Ser Ser
        115                 120
```

<210> SEQ ID NO 118
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Arg Gln Lys Pro Gly Gln Gly Leu Glu Trp Ile
            35                  40                  45

Gly Tyr Ile Asp Pro Asp Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Ala Tyr Tyr Gly Gly Leu Tyr Gly Met Asp Tyr Trp Gly
                100                 105                 110

Gln Gly Ser Ser Val Thr Val Ser Ser
```

```
              115                 120

<210> SEQ ID NO 119
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Gly Gly Gly Ser Tyr Tyr Pro Asp Ser Val
    50                  55                  60

Lys Gly Arg Phe Thr Ile Ser Arg Asp Asn Thr Lys Asn Thr Leu Tyr
65                  70                  75                  80

Leu Gln Met Ser Ser Leu Lys Ser Glu Asp Thr Ala Val Tyr Tyr Cys
                85                  90                  95

Ala Arg Leu Pro His Tyr Phe Ala Met Asp Cys Trp Gly Gln Gly Thr
            100                 105                 110

Ser Val Thr Val Ser Ser
        115

<210> SEQ ID NO 120
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Phe Asn Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Gly Gly Tyr Trp Ser Leu Tyr Phe Asp Tyr Trp Gly Gln Gly
            100                 105                 110

Thr Thr Leu Thr Val Ser Ser
        115

<210> SEQ ID NO 121
<211> LENGTH: 117
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 121

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Gly His Thr Lys Tyr Asn Glu Lys Phe
    50                  55                  60

Lys Gly Glu Ala Thr Leu Thr Val Asp Thr Ser Arg Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Ser Asn Tyr Tyr Phe Asp Phe Trp Gly His Gly Thr Thr
            100                 105                 110

Leu Thr Val Ser Ser
        115

<210> SEQ ID NO 122
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Ser Tyr
            20                  25                  30

Tyr Ile Gln Trp Val Lys Gln Arg Pro Gly Gln Gly Leu Glu Trp Ile
        35                  40                  45

Gly Trp Ile Tyr Pro Gly Asp Gly Thr Thr Asn Tyr Asn Glu Asn Phe
    50                  55                  60

Lys Gly Lys Thr Thr Leu Thr Ala Asp Lys Ser Ser Thr Val Tyr
65                  70                  75                  80

Met Leu Leu Ser Ser Leu Thr Ser Glu Asp Ser Ala Val Tyr Phe Cys
                85                  90                  95

Ala Arg Tyr Gly Leu Val Pro Phe Asp Tyr Trp Gly Gln Gly Thr Thr
            100                 105                 110

Leu Thr Val Ser Ser
        115

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ile Gln Leu Gln Gln Ser Gly Pro Glu Leu Val Lys Thr Gly Ala
1               5                   10                  15

Ser Val Lys Ile Ser Cys Lys Ala Ser Gly Asn Thr Phe Asn Ser Asn
            20                  25                  30

-continued

```
Tyr Ile Gln Trp Val Lys Gln Arg Pro Gly Gln Gly Leu Glu Trp Ile
            35                  40                  45

Gly Trp Ile Tyr Pro Gly Asp Gly Ser Thr Asn Tyr Ser Glu Lys Phe
 50                  55                  60

Lys Gly Lys Thr Thr Leu Thr Ala Asp Lys Ser Ser Thr Ala Tyr
 65                  70                  75                  80

Met Leu Val Ser Ser Leu Thr Ser Glu Asp Ser Ala Val Tyr Phe Cys
                 85                  90                  95

Ala Arg Tyr Gly Pro Val Pro Phe Asp Tyr Trp Gly Gln Gly Thr Thr
                100                 105                 110

Leu Ser Val Ser Ser
            115

<210> SEQ ID NO 124
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gatatccaga tgacgcagag cccaagcagc ctgagcgcgt ccgtgggcga ccgcgtgacg      60
atcacctgta gcgcgtccca gagcatcagc agcgactatc tgcattggta tcagcagaaa    120
ccaggtaaag cccctaaaact gctgatctac cggacctcca atctggcaag cggcgtgcct   180
agccgtttca gcgtagcgg ctccggtacc gacttcacct ttactatctc cagcctgcag     240
cctgaagaca tcgcgacgta ttattgtcag cagggtacta gcctgcctcg cgccttcggc    300
caggggacca aactggaaat caaa                                           324

<210> SEQ ID NO 125
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Ser Ile Ser Ser Asp
             20                  25                  30

Tyr Leu His Trp Tyr Gln Gln Lys Pro Gly Lys Ala Pro Lys Leu Leu
         35                  40                  45

Ile Tyr Arg Thr Ser Asn Leu Ala Ser Gly Val Pro Ser Arg Phe Ser
 50                  55                  60

Gly Ser Gly Ser Gly Thr Asp Phe Thr Phe Thr Ile Ser Ser Leu Gln
 65                  70                  75                  80

Pro Glu Asp Ile Ala Thr Tyr Tyr Cys Gln Gln Gly Thr Ser Leu Pro
                 85                  90                  95

Arg Ala Phe Gly Gln Gly Thr Lys Leu Glu Ile Lys
                100                 105

<210> SEQ ID NO 126
<211> LENGTH: 324
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 126
gatatccaga tgacgcagag cccaagcagc ctgagcgcgt ccgtgggcga ccgcgtgacg         60
atcacctgtc aggcgtccca gagcatcagc agcgactatc tgcattggta tcagcagaaa        120
ccaggtaaag ccccctaaact gctgatctac cggacctcca atctggaaac cggcgtgcct       180
agccgtttca gcggtagcgg ctccggtacc gacttcacct ttactatctc cagcctgcag        240
cctgaagaca tcgcgacgta ttattgtcag cagggtacta gcctgcctcg cgccttcggc        300
caggggacca aactggaaat caaa                                                324

<210> SEQ ID NO 127
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Asp
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Glu Thr Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Gly Thr Ser Leu Pro
                85                  90                  95

Arg Ala Phe Gly Gln Gly Thr Lys Leu Glu Ile Lys
            100                 105

<210> SEQ ID NO 128
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
gatatccaga tgacgcagag cccaagcagc ctgagcgcgt ccgtgggcga ccgcgtgacg         60
atcacctgtc aggcgtccca gagcatcagc agcgactatc tgcattggta tcagcagaaa        120
ccaggtaaag ccccctaaact gctgatctac cggacctcca atctggaaag cggcgtgcct       180
agccgtttca gcggtagcgg ctccggtacc gacttcacct ttactatctc cagcctgcag        240
cctgaagaca tcgcgacgta ttattgtcag cagggtacta gcctgcctcg cgccttcggc        300
caggggacca aactggaaat caaa                                                324

<210> SEQ ID NO 129
<211> LENGTH: 108
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Asp
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Glu Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Gly Thr Ser Leu Pro
                85                  90                  95

Arg Ala Phe Gly Gln Gly Thr Lys Leu Glu Ile Lys
            100                 105

<210> SEQ ID NO 130
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gaagtgcagc tggtggaaag cggtggtggc ctggtgcagc caggcggctc cctgcgcctg      60
agctgcgccg caagcggttt cacctttagc gactactata tgtcctgggt gcgtcaggcg     120
ccaggtaaag gtctggaatg gtgtcatac atcagctccg ggggcggtag caagtactat      180
ccggacctgg tgaaagggcg ctttactatc tcccgggata atgcaaaaaa tagcctgtac     240
ctgcagatga gcagcctgcg ggcggaagat accgccgtgt attactgtgc gcgtctgccg     300
cattatttcg ccatggatta ctggggccag gggaccctgg tgaccgtgag cagc           354

<210> SEQ ID NO 131
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Tyr Ile Ser Ser Gly Gly Gly Ser Lys Tyr Tyr Pro Asp Leu Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr

Leu Val Thr Val Ser Ser
        115

<210> SEQ ID NO 132
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
gaagtgcagc tggtggaaag cggtggtggc ctggtgcagc caggcggctc cctgcgcctg      60
agctgcgccg caagcggttt cacctttagc gactactata tgtcctgggt gcgtcaggcg     120
ccaggtaaag gtctggaatg ggtggcatac atcagctccg ggggcggtag cagctactat     180
ccggacctgg tgaaagggcg ctttactatc tcccgggata atgcaaaaaa tagcctgtac     240
ctgcagatgc agagcctgcg gcggaagat accgccgtgt attactgtgc gcgtctgccg     300
cattatttcg ccatggatta ctggggccag ggaccctgg tgaccgtgag cagc            354

<210> SEQ ID NO 133
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Tyr Ile Ser Ser Gly Gly Gly Ser Ser Tyr Tyr Pro Asp Leu Val
    50                  55                  60

Lys Gly Arg Phe Thr Ile Ser Arg Asp Asn Ala Lys Asn Ser Leu Tyr
65                  70                  75                  80

Leu Gln Met Gln Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser
        115

<210> SEQ ID NO 134
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gaagtgcagc tggtggaaag cggtggtggc ctggtgcagc caggcggctc cctgcgcctg      60
agctgcgccg caagcggttt cacctttagc gactactata tgtcctgggt gcgtcaggcg     120
ccaggtaaag gtctggaatg ggtggcatac atcagctccg ggggcggtag cagctactat     180

```
ccggacgctg tgaaagggcg ctttactatc tcccgggata atgcaaaaca gagcctgtac    240
ctgcagatgc agagcctgcg ggcggaagat accgccgtgt attactgtgc gcgtctgccg    300
cattatttcg ccatggatta ctggggccag gggaccctgg tgaccgtgag cagc          354
```

<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Tyr Ile Ser Ser Gly Gly Gly Ser Ser Tyr Tyr Pro Asp Ala Val
    50                  55                  60

Lys Gly Arg Phe Thr Ile Ser Arg Asp Asn Ala Lys Gln Ser Leu Tyr
65                  70                  75                  80

Leu Gln Met Gln Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser
        115
```

<210> SEQ ID NO 136
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
gaagtgcagc tggtggaaag cggtggtggc ctggtgcagc caggcggctc cctgcgcctg    60
agctgcgccg caagcggttt cacctttagc gactactata tgtcctgggt gcgtcaggcg    120
ccaggtaaag gtctggaatg ggtggcctac atcagctccg gggcggtag cagctactat    180 ccggacctgg tgaaagggcg ctttactatc tcccgggata atgcaaaaca gagcctgtac    240
ctgcagatga acagcctgcg ggcggaagat accgccgtgt attactgtgc gcgtctgccg    300
cattatttcg ccatggatta ctggggccag gggaccctgg tgaccgtgag cagc          354
```

<210> SEQ ID NO 137
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Tyr Ile Ser Ser Gly Gly Gly Ser Ser Tyr Tyr Pro Asp Leu Val
    50                  55                  60

Lys Gly Arg Phe Thr Ile Ser Arg Asp Asn Ala Lys Gln Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser
            115

<210> SEQ ID NO 138
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gaagtgcagc tggtggaaag cggtggtggc ctggtgcagc caggcggctc cctgcgcctg      60
agctgcgccg caagcggttt cacctttagc gactactata tgtcctgggt gcgtcaggcg     120
ccaggtaaag gtctggaatg ggtggcctac atcagctccg ggggcggtag cagctactat     180
ccggacctgg tgaaagggcg ctttactatc tcccgggata atgcaaaaca gagcctgtac     240
ctgcagatgc agagcctgcg ggcggaagat accgccgtgt attactgtgc gcgtctgccg     300
cattatttcg ccatggatta ctggggccag gggaccctgg tgaccgtgag cagc            354

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Tyr Ile Ser Ser Gly Gly Gly Ser Ser Tyr Tyr Pro Asp Leu Val
    50                  55                  60

Lys Gly Arg Phe Thr Ile Ser Arg Asp Asn Ala Lys Gln Ser Leu Tyr
65                  70                  75                  80

Leu Gln Met Gln Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser
            115
```

<210> SEQ ID NO 140
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
gatatccaga tgacgcagag cccaagcagc ctgagcgcgt ccgtgggcga ccgcgtgacg      60
atcacctgta gcgcgtccca gagcatcagc agcgactatc tgcattggta tcagcagaaa    120
ccaggtaaag cccctaaact gctgatctac cggacctcca atctggcaag cggcgtgcct    180
agccgtttca gcggtagcgg ctccggtacc gacttcacct ttactatctc cagcctgcag    240
cctgaagaca tcgcgacgta ttattgtcag cagggtacta gcctgcctcg cgccttcggc    300
caggggacca aactggaaat caaacgtact gtggctgcac catctgtctt catcttcccg    360
ccatctgatg agcaattgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                    645
```

<210> SEQ ID NO 141
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Ser Ile Ser Ser Asp
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Gly Thr Ser Leu Pro
                85                  90                  95

Arg Ala Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 142
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
gaagtgcagc tggtggaaag cggtggtggc ctggtgcagc caggcggctc cctgcgcctg      60
agctgcgccg caagcggttt caccttagc gactactata tgtcctgggt gcgtcaggcg     120
ccaggtaaag gtctggaatg ggtgtcatac atcagctccg ggggcggtag caagtactat     180
ccggacctgg tgaaagggcg ctttactatc tcccgggata atgcaaaaaa tagcctgtac     240
ctgcagatga gcagcctgcg ggcggaagat accgccgtgt attactgtgc gcgtctgccg     300
cattatttcg ccatggatta ctggggccag gggaccctgg tgaccgtgag cagcgcctcc     360
acaaagggcc cttccgtgtt ccccctggcc ccttgctccc ggtccacctc cgagtctacc     420
gccgctctgg gctgcctggt caaggactac ttccccgagc ccgtgaccgt gtcctggaac     480
tctggcgccc tgacctccgg cgtgcacacc ttccctgctg tgctgcagtc ctccggcctg     540
tactccctgt cctccgtcgt gaccgtgccc tcctctagcc tgggcaccaa gacctacacc     600
tgtaacgtgg accacaagcc ctccaacacc aaggtggaca gcgggtgga atctaagtac     660 ggccctccct gccccccctg ccctgcccct gaatttctgg gcggaccctc cgtgttcctg     720
ttccccccaa agcccaagga caccctgatg atctcccgga ccccgaagt gacctgcgtg     780 gtggtggacg tgtcccagga agatcccgag gtccagttta attggtacgt ggacggcgtg     840
gaagtgcaca acgccaagac caagcccaga gaggaacagt tcaactccac ctaccgggtg     900
gtgtccgtgc tgaccgtgct gcaccaggac tggctgaacg gcaaagagta caagtgcaag     960
gtgtccaaca agggcctgcc ctccagcatc gaaaagacca tctccaaggc caagggccag    1020
ccccgcgagc cccaggtgta caccctgcct ccaagccagg aagagatgac caagaaccag    1080
gtgtccctga cctgtctggt caagggcttc taccctccg atatcgccgt ggaatgggag    1140
tccaacggcc agcccgagaa caactacaag accaccccc ctgtgctgga ctccgacggc    1200
tccttcttcc tgtactctcg gctgaccgtg gacaagtccc ggtggcagga aggcaacgtc    1260
ttctcctgct ccgtgatgca cgaggccctg cacaaccact acacccagaa gtccctgtcc    1320
ctgagcctgg gc                                                        1332
```

<210> SEQ ID NO 143
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr

```
                20                  25                  30
Tyr Met Ser Trp Val Arg Gln Ala Pro Gly Lys Gly Leu Glu Trp Val
            35                  40                  45

Ser Tyr Ile Ser Ser Gly Gly Ser Lys Tyr Tyr Pro Asp Leu Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 144
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gacatccaga tgacccagag cccaagcagc ctgagcgcca gcgtgggcga ccgcgtgacc      60
atcacctgcc aggccagcca gagcatcagc agcgactacc tgcactggta ccagcagaag     120
ccaggcaagg ccccaaagct gctgatctac cgcaccagca acctggagac cggcgtgcca     180
agccgcttca gcggcagcgg cagcggcacc gacttcacct tcaccatcag cagcctgcag     240
ccagaggaca tcgccaccta ctactgccag cagggcacca gcctgccacg cgccttcggc     300
cagggcacca gcctggagat caagcgtact gtggctgcac catctgtctt catcttcccg     360
ccatctgatg agcaattgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac cgagaaacac aaagtctacg cctgcgaagt cacccatcag     600
ggcctgagct cgcccgtcac aaagagcttc aacaggggag agtgt                    645

<210> SEQ ID NO 145
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Asp
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Glu Thr Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Gly Thr Ser Leu Pro
                85                  90                  95

Arg Ala Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val 180                 185                 190
Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 146
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

| | | | | | |
|---|---|---|---|---|---|
| gaagtgcagc | tggtggaaag | cggcggaggc | ctggtgcagc | caggcggcag | cctgagactg | 60 |
| agctgcgccg | ccagcggctt | caccttcagc | gactactaca | tgagctgggt | gcgccaggcc | 120 |
| ccaggcaagg | gcctggagtg | ggtggcctac | atcagcagcg | gcggcggcag | cagctactac | 180 |
| ccagacctgg | tgaagggccg | cttcaccatc | agccgcgaca | acgccaagaa | cagcctgtac | 240 |
| ctgcagatgc | agagcctgcg | cgccgaggac | accgccgtgt | actactgcgc | cgcctgcca | 300 |
| cactacttcg | ccatggacta | ctggggccag | ggcaccctgg | tgaccgtgag | cagcgcctcc | 360 |
| acaaagggcc | cttccgtgtt | ccccctggcc | ccttgctccc | ggtccacctc | cgagtctacc | 420 |
| gccgctctgg | gctgcctggt | caaggactac | ttccccgagc | ccgtgaccgt | gtcctggaac | 480 |
| tctggcgccc | tgacctccgg | cgtgcacacc | ttccctgctg | tgctgcagtc | ctccggcctg | 540 |
| tactccctgt | cctccgtcgt | gaccgtgccc | tcctctagcc | tgggcaccaa | gacctacacc | 600 |
| tgtaacgtgg | accacaagcc | ctccaacacc | aaggtggaca | agcgggtgga | atctaagtac | 660 |
| ggccctccct | gccccccctg | ccctgcccct | gaatttctgg | gcggaccctc | cgtgttcctg | 720 |
| ttccccccaa | agcccaagga | caccctgatg | atctcccgga | cccccgaagt | gacctgcgtg | 780 |
| gtggtggacg | tgtcccagga | agatcccgag | gtccagtttta | attggtacgt | ggacggcgtg | 840 |
| gaagtgcaca | acgccaagac | caagcccaga | gaggaacagt | tcaactccac | ctaccgggtg | 900 |
| gtgtccgtgc | tgaccgtgct | gcaccaggac | tggctgaacg | gcaaagagta | caagtgcaag | 960 |
| gtgtccaaca | agggcctgcc | ctccagcatc | gaaaagacca | tctccaaggc | caagggccag | 1020 |
| ccccgcgagc | cccaggtgta | caccctgcct | ccaagccagg | aagagatgac | caagaaccag | 1080 |
| gtgtccctga | cctgtctggt | caagggcttc | tacccctccg | atatcgccgt | ggaatgggag | 1140 |
| tccaacggcc | agcccgagaa | caactacaag | accaccccc | ctgtgctgga | ctccgacggc | 1200 |
| tccttcttcc | tgtactctcg | gctgaccgtg | gacaagtccc | ggtggcagga | aggcaacgtc | 1260 |
| ttctcctgct | ccgtgatgca | cgaggccctg | cacaaccact | acacccagaa | gtccctgtcc | 1320 |
| ctgagcctgg | gc | | | | | 1332 |

<210> SEQ ID NO 147
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
         35                  40                  45

Ala Tyr Ile Ser Ser Gly Gly Ser Ser Tyr Tyr Pro Asp Leu Val
     50                  55                  60

Lys Gly Arg Phe Thr Ile Ser Arg Asp Asn Ala Lys Asn Ser Leu Tyr
 65                  70                  75                  80

Leu Gln Met Gln Ser Leu Arg Ala Glu Asp Thr Ala Val Tyr Tyr Cys
                 85                  90                  95

Ala Arg Leu Pro His Tyr Phe Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
```

<210> SEQ ID NO 148
<211> LENGTH: 1332
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 148

```
gaggtgcagc tggtggagag cggcggcggc ctggtgcagc aggtggtag cctgcgcctg      60
agctgcgccg ccagcggctt caccttcagc gactactaca tgagctgggt gcgccaggct    120
ccaggcaagg gtctggaatg ggtggcctac atcagcagcg gcggcggcag cagctactac    180
ccagacgccg tgaagggccg cttcaccatc agccgcgaca cgccaagca gagcctgtac     240
ctgcagatgc agagcctgcg cgccgaggac accgccgtgt actactgcgc ccgcctgcca    300
cactacttcg ccatggacta ctggggccag ggcaccctgg tgaccgtgag cagcgcctcc    360
acaaagggcc cttccgtgtt ccccctggcc ccttgctccc ggtccacctc cgagtctacc    420
gccgctctgg gctgcctggt caaggactac ttccccgagc ccgtgaccgt gtcctggaac    480
tctggcgccc tgacctccgg cgtgcacacc ttccctgctg tgctgcagtc ctccggcctg    540
tactccctgt cctccgtcgt gaccgtgccc tcctctagcc tgggcaccaa gacctacacc    600
tgtaacgtgg accacaagcc ctccaacacc aaggtggaca gcgggtgga atctaagtac    660
ggccctccct gccccccctg ccctgcccct gaatttctgg gcggaccctc cgtgttcctg    720
ttcccccca agcccaagga caccctgatg atctcccgga cccccgaagt gacctgcgtg    780
gtggtggacg tgtcccagga agatcccgag gtccagttta attggtacgt ggacggcgtg    840
gaagtgcaca acgccaagac caagcccaga gaggaacagt tcaactccac ctaccgggtg    900
gtgtccgtgc tgaccgtgct gcaccaggac tggctgaacg gcaaagagta caagtgcaag    960
gtgtccaaca agggcctgcc ctccagcatc gaaaagacca tctccaaggc caagggccag   1020
ccccgcgagc cccaggtgta caccctgcct ccaagccagg aagagatgac caagaaccag   1080
gtgtccctga cctgtctggt caagggcttc taccctccg atatcgccgt ggaatgggag   1140
tccaacggcc agcccgagaa caactacaag accacccccc ctgtgctgga ctccgacggc   1200
tccttcttcc tgtactctcg gctgaccgtg gacaagtccc ggtggcagga aggcaacgtc   1260
ttctcctgct ccgtgatgca cgaggccctg cacaaccact acacccagaa gtccctgtcc   1320
ctgagcctgg gc                                                       1332
```

<210> SEQ ID NO 149
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

```
Ala Tyr Ile Ser Ser Gly Gly Gly Ser Ser Tyr Tyr Pro Asp Ala Val
 50                  55                  60

Lys Gly Arg Phe Thr Ile Ser Arg Asp Asn Ala Lys Gln Ser Leu Tyr
 65                  70                  75                  80

Leu Gln Met Gln Ser Leu Arg Ala Glu Asp Thr Ala Val Tyr Tyr Cys
                 85                  90                  95

Ala Arg Leu Pro His Tyr Phe Ala Met Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
                435                 440

<210> SEQ ID NO 150
<211> LENGTH: 645
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 150

```
gacatccaga tgacccagag cccaagcagc ctgagcgcca gcgtgggcga ccgcgtgacc    60
atcacctgcc aggccagcca gagcatcagc agcgactacc tgcactggta ccagcagaag   120
ccaggcaagg ccccaaagct gctgatctac cgcaccagca acctggagag cggcgtgcca   180
agccgcttca gcggcagcgg cagcggcacc gacttcacct tcaccatcag cagcctgcag   240
ccagaggaca tcgccaccta ctactgccag cagggcacca gcctgccacg cgccttcggc   300
cagggcacca agctggagat caagcgtact gtggctgcac catctgtctt catcttcccg   360
ccatctgatg agcaattgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgt                   645
```

<210> SEQ ID NO 151
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Asp
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Glu Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Gly Thr Ser Leu Pro
                85                  90                  95

Arg Ala Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215
```

<210> SEQ ID NO 152
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152

| | |
|---|---|
| gaagtgcagc tggtggaaag cggtggtggc ctggtgcagc caggcggctc cctgcgcctg | 60 |
| agctgcgccg caagcggttt cacctttagc gactactata tgtcctgggt gcgtcaggcg | 120 |
| ccaggtaaag gtctggaatg ggtggcctac atcagctccg ggggcggtag cagctactat | 180 |
| ccggacctgg tgaaagggcg ctttactatc tcccgggata atgcaaaaca gagcctgtac | 240 |
| ctgcagatga acagcctgcg ggcggaagat accgccgtgt attactgtgc gcgtctgccg | 300 |
| cattatttcg ccatggatta ctgggccag gggaccctgg tgaccgtgag cagcgcctcc | 360 |
| acaaagggcc cttccgtgtt ccccctggcc ccttgctccc ggtccacctc cgagtctacc | 420 |
| gccgctctgg gctgcctggt caaggactac ttccccgagc ccgtgaccgt gtcctggaac | 480 |
| tctggcgccc tgacctccgg cgtgcacacc ttccctgctg tgctgcagtc ctccggcctg | 540 |
| tactccctgt cctccgtcgt gaccgtgccc tcctctagcc tgggcaccaa gacctacacc | 600 |
| tgtaacgtgg accacaagcc ctccaacacc aaggtggaca gcgggtgga atctaagtac | 660 |
| ggccctccct gccccccctg ccctgcccct gaatttctgg gcggaccctc cgtgttcctg | 720 |
| ttcccccaa agcccaagga caccctgatg atctcccgga ccccgaagt gacctgcgtg | 780 |
| gtggtggacg tgtcccagga agatcccgag gtccagttta attggtacgt ggacggcgtg | 840 |
| gaagtgcaca acgccaagac caagcccaga gaggaacagt tcaactccac ctaccgggtg | 900 |
| gtgtccgtgc tgaccgtgct gcaccaggac tggctgaacg gcaaagagta caagtgcaag | 960 |
| gtgtccaaca agggcctgcc ctccagcatc gaaaagacca tctccaaggc caagggccag | 1020 |
| ccccgcgagc cccaggtgta caccctgcct ccaagccagg aagagatgac caagaaccag | 1080 |
| gtgtccctga cctgtctggt caagggcttc taccctccg atatcgccgt ggaatgggag | 1140 |
| tccaacggcc agcccgagaa caactacaag accacccccc ctgtgctgga ctccgacggc | 1200 |
| tccttcttcc tgtactctcg gctgaccgtg gacaagtccc ggtggcagga aggcaacgtc | 1260 |
| ttctcctgct ccgtgatgca cgaggccctg cacaaccact acacccagaa gtccctgtcc | 1320 |
| ctgagcctgg gc | 1332 |

<210> SEQ ID NO 153
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45
```

```
Ala Tyr Ile Ser Ser Gly Gly Ser Ser Tyr Tyr Pro Asp Leu Val
 50                  55                  60

Lys Gly Arg Phe Thr Ile Ser Arg Asp Asn Ala Lys Gln Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Pro His Tyr Phe Ala Met Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 154
<211> LENGTH: 1332
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
gaggtgcagc tggtggagag cggcggcggc ctggtgcagc aggtggtag cctgcgcctg      60
agctgcgccg ccagcggctt caccttcagc gactactaca tgagctgggt gcgccaggct     120
ccaggcaagg gtctggaatg ggtggcctac atcagcagcg gcggcggcag cagctactac     180
ccagacctgg tgaagggccg cttcaccatc agccgcgaca cgccaagca gagcctgtac      240
ctgcagatgc agagcctgcg cgccgaggac accgccgtgt actactgcgc ccgcctgcca     300
cactacttcg ccatggacta ctggggccag ggcaccctgg tgaccgtgag cagcgcctcc     360
acaaagggcc cttccgtgtt cccctggcc ccttgctccc ggtccacctc cgagtctacc      420
gccgctctgg gctgcctggt caaggactac ttccccgagc ccgtgaccgt gtcctggaac     480
tctggcgccc tgacctccgg cgtgcacacc ttccctgctg tgctgcagtc ctccggcctg     540
tactccctgt cctccgtcgt gaccgtgccc tcctctagcc tgggcaccaa gacctacacc     600
tgtaacgtgg accacaagcc ctccaacacc aaggtggaca gcgggtgga atctaagtac      660
ggccctccct gccccccctg ccctgccccct gaatttctgg gcggaccctc cgtgttcctg    720
ttccccccaa agcccaagga caccctgatg atctcccgga cccccgaagt gacctgcgtg    780
gtggtggacg tgtcccagga agatcccgag gtccagtttta attggtacgt ggacggcgtg    840
gaagtgcaca cgccaagac caagcccaga gaggaacagt tcaactccac ctaccgggtg    900
gtgtccgtgc tgaccgtgct gcaccaggac tggctgaacg gcaaagagta caagtgcaag    960
gtgtccaaca gggcctgcc ctccagcatc gaaaagacca ctctccaaggc caagggccag   1020
ccccgcgagc ccaggtgta cacctgcct ccaagccagg aagagatgac caagaaccag    1080
gtgtccctga cctgtctggt caagggcttc taccccctccg atatcgccgt ggaatgggag   1140
tccaacggcc agcccgagaa caactacaag accacccccc ctgtgctgga ctccgacggc   1200
tccttcttcc tgtactctcg gctgaccgtg gacaagtccc ggtggcagga aggcaacgtc   1260
ttctcctgct ccgtgatgca cgaggccctg cacaaccact acacccagaa gtccctgtcc   1320
ctgagcctgg gc                                                       1332

<210> SEQ ID NO 155
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Tyr Ile Ser Ser Gly Gly Gly Ser Ser Tyr Tyr Pro Asp Leu Val
    50                  55                  60

Lys Gly Arg Phe Thr Ile Ser Arg Asp Asn Ala Lys Gln Ser Leu Tyr
65                  70                  75                  80
```

Leu Gln Met Gln Ser Leu Arg Ala Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 156
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 156

```
gagatcgtgc tgacacagag ccctaccaca atggccgcct ctccaggcga gaagatcacc    60
atcacatgta gcgccagcag cagcatcagc agcgactacc tgcactggta tcagcagaag   120
cctggcttca gccccgagct gctgatctac agaacaagca atctggccag cggcgtgcca   180
gccagatttt ctggttctgg cagcggcacc agctacagcc tgacaatcgg atccatggaa   240
gccgaggacg tggccaccta ttactgtcag cagggcacaa gcctgcctag gcctttggc   300
ggaggcacca agctggaaat caagcgtact gtggctgcac catctgtctt catcttccg   360
ccatctgatg agcaattgaa atctggaact gcctctgttg tgtgcctgct gaataacttc   420
tatcccagag aaggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgt              645
```

<210> SEQ ID NO 157
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

```
Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asp
            20                  25                  30

Tyr Leu His Trp Tyr Gln Gln Lys Pro Gly Phe Ser Pro Glu Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Ser Met Glu
65                  70                  75                  80

Ala Glu Asp Val Ala Thr Tyr Tyr Cys Gln Gln Gly Thr Ser Leu Pro
                85                  90                  95

Arg Ala Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 158

<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158

```
gaagtgcagc tggtggaatc tggcggagga cttgttcaac ctggcggcag cctgaaactg      60
tcttgtgccg ccagcggctt caccttcagc gactactaca tgagctgggt ccgacagacc     120
cctgagaaga gactggaatg ggtcgcctac atcagctctg gcggcggaag cagctactac     180
cctgatagcg tgaagggcag attcaccatc agccgggaca caccaagaa cacccctgtac     240
ctgcagatgt ccagcctgaa gtctgaggac accgccgtgt actactgtgc cagactgcct     300
cactacttcg ccatggatta ttggggccag ggcaccagcg tgaccgtttc ttctgcctcc     360
accaagggcc catcggtctt cccgctagca cctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gcgcgttga cccaaatct      660
tgtgacaaaa ctcacacatg cccaccgtgc ccagcacctg aactactagg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc ccgagaacc acaggtgtac accctgcccc catcccgcga ggagatgacc    1080
aagaaccagg taagtttgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 159
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Gly Gly Gly Ser Ser Tyr Tyr Pro Asp Ser Val
    50                  55                  60

Lys Gly Arg Phe Thr Ile Ser Arg Asp Asn Thr Lys Asn Thr Leu Tyr
```

```
             65                  70                  75                  80
Leu Gln Met Ser Ser Leu Lys Ser Glu Asp Thr Ala Val Tyr Tyr Cys
                85                  90                  95

Ala Arg Leu Pro His Tyr Phe Ala Met Asp Tyr Trp Gly Gln Gly Thr
                100                 105                 110

Ser Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 160
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 160

```
gaagtgcagc tggtggaatc tggcggagga cttgttcaac ctggcggcag cctgaaactg      60
tcttgtgccg ccagcggctt caccttcagc gactactaca tgagctgggt ccgacagacc     120
cctgagaaga gactggaatg ggtcgcctac atcagtctg gcggcggaag cagctactac      180
cctgatagcg tgaagggcag attcaccatc agccgggaca acaccaagaa caccctgtac     240
ctgcagatgt ccagcctgaa gtctgaggac accgccgtgt actactgtgc agactgcct     300
cactacttcg ccatggattg ttggggccag ggcacatctg tgaccgttag ttctgcctcc     360
accaagggcc catcggtctt cccgctagca ccctcctcca gagcacctc tgggggcaca     420
gcggccctgg gctgcctggt caaggactac ttccccgaac cggtgacggt gtcgtggaac     480
tcaggcgccc tgaccagcgg cgtgcacacc ttccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gcgcgttga gcccaaatct     660
tgtgacaaaa ctcacacatg cccaccgtgc ccagcacctg aagccgctgg ggaccgtca     720
gtcttcctct ccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccgcga ggagatgacc    1080
aagaaccagg taagtttgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 161
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Gly Gly Gly Ser Ser Tyr Tyr Pro Asp Ser Val
    50                  55                  60

Lys Gly Arg Phe Thr Ile Ser Arg Asp Asn Lys Asn Thr Leu Tyr
65                  70                  75                  80

Leu Gln Met Ser Ser Leu Lys Ser Glu Asp Thr Ala Val Tyr Tyr Cys
                85                  90                  95

Ala Arg Leu Pro His Tyr Phe Ala Met Asp Cys Trp Gly Gln Gly Thr
```

|     |     |     |     |     | 100 |     |     |     | 105 |     |     |     |     | 110 |     |
| --- | --- | --- | --- | --- | --- | --- | --- | --- | --- | --- | --- | --- | --- | --- | --- |

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 162
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
gaagtgcagc tggtggaatc tggcggagga cttgttcaac tggcggcag cctgaaactg      60 tcttgtgccg ccagcggctt caccttcagc gactactaca tgagctgggt ccgacagacc    120

```
cctgagaaga gactggaatg ggtcgcctac atcagctctg gcggcggaag cagctactac    180
cctgatagcg tgaagggcag attcaccatc agccgggaca acaccaagaa cacccctgta    240
ctgcagatgt ccagcctgaa gtctgaggac accgccgtgt actactgtgc cagactgcct    300
cactacttcg ccatggatta ttggggccag ggcaccagcg tgaccgtttc ttctgcctcc    360
acaaagggcc cttccgtgtt ccccctggcc ccttgctccc ggtccacctc cgagtctacc    420
gccgctctgg gctgcctggt caaggactac ttccccgagc ccgtgaccgt gtcctggaac    480
tctggcgccc tgacctccgg cgtgcacacc ttccctgctg tgctgcagtc ctccggcctg    540
tactccctgt cctccgtcgt gaccgtgccc tcctctagcc tgggcaccaa gacctacacc    600
tgtaacgtgg accacaagcc ctccaacacc aaggtggaca gcgggtgga atctaagtac    660
ggccctccct gcccccctg ccctgcccct gaatttctgg gcggaccctc cgtgttcctg    720
ttcccccaa agcccaagga caccctgatg atctcccgga cccccgaagt gacctgcgtg    780
gtggtggacg tgtcccagga agatcccgag gtccagttta attggtacgt ggacggcgtg    840
gaagtgcaca acgccaagac caagcccaga gaggaacagt tcaactccac ctaccgggtg    900
gtgtccgtgc tgaccgtgct gcaccaggac tggctgaacg gcaaagagta caagtgcaag    960
gtgtccaaca agggcctgcc ctccagcatc gaaaagacca tctccaaggc caagggccag   1020
ccccgcgagc cccaggtgta cacccctgcct ccaagccagg aagagatgac caagaaccag   1080
gtgtccctga cctgtctggt caagggcttc taccctccg atatcgccgt ggaatgggag   1140
tccaacggcc agcccgagaa caactacaag accacccccc ctgtgctgga ctccgacggc   1200
tccttcttcc tgtactctcg gctgaccgtg gacaagtccc ggtggcagga aggcaacgtc   1260
ttctcctgct ccgtgatgca cgaggccctg cacaaccact acacccagaa gtccctgtcc   1320
ctgagcctgg gc                                                       1332
```

<210> SEQ ID NO 163
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Gly Gly Ser Ser Tyr Tyr Pro Asp Ser Val
    50                  55                  60

Lys Gly Arg Phe Thr Ile Ser Arg Asp Asn Lys Asn Thr Leu Tyr
65                  70                  75                  80

Leu Gln Met Ser Ser Leu Lys Ser Glu Asp Thr Ala Val Tyr Tyr Cys
                85                  90                  95

Ala Arg Leu Pro His Tyr Phe Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
```

```
            130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
        435                 440

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ala Ser Gln Ser Ile Ser Ser Asp Tyr Leu His
1               5                   10

<210> SEQ ID NO 165
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 165

Gln Ala Ser Gln Ser Ile Ser Ser Asp Tyr Leu His
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Thr Ser Asn Leu Glu Thr
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Thr Ser Asn Leu Glu Ser
1               5
```

ANTI-PD-1 ANTIBODIES

SEQUENCE LISTING

The instant application contains a Sequence Listing which has been submitted electronically in ASCII format and is hereby incorporated by reference in its entirety. Said ASCII copy, created on Apr. 29, 2021, is named 09-0701-US-3_SL.txt and is 132,853 bytes in size.

FIELD OF THE INVENTION

This invention generally relates to anti-PD-1 (Programmed cell death 1) antibodies for therapeutic and diagnostic use. More specifically, anti-PD-1 antibodies and methods of use for the treatment of various diseases or disorders characterized by cells expressing PD-1 are disclosed. Pharmaceutical compositions and kits comprising the anti-PD-1 antibodies are also disclosed.

BACKGROUND OF THE INVENTION

Programmed cell death 1, also known as PD-1 and CD279 (cluster of differentiation 279), is a cell surface receptor protein expressed primarily on T-cells, but also on other immune cells. The PD-1 pathway is a key regulator in the induction and maintenance of immunological tolerance. The protein functions as an "immune checkpoint" inhibitor, i.e. it acts to modulate the activity of cells in the immune system so as to regulate and limit autoimmune diseases. PD-1 has two ligands, PD-L1 and PD-L2, which interact with the cell surface receptor. On binding, PD-1 induces an intracellular signal, which negatively regulates T-cell responses. On the surface of activated T cells, PD-1 expression is upregulated after the recognition of peripheral antigens by T cells; subsequently, the elevated binding of PD-1 to PD-L1 and PD-L2 becomes a key step for downstream inhibitory signaling. PD-1 is also associated with increased Treg-cell proliferation and enhanced immunosuppressive function.

It has been recently understood that many cancers can protect themselves from the immune system by modifying "immune checkpoint" inhibitors and thus avoid detection. PD-1 inhibitors, a new class of drugs that block PD-1, activate the immune system to attack tumors and are used to treat certain types of cancer.

In contrast, defective PD-1 inhibitory functions have also been associated with pathophysiology of immune-mediated diseases, and expression of PD-1 or it is ligands may be dysregulated or not fully engaged in certain autoimmune indications. Induction of PD-1 activation and the use of the PD-1/PD-L1 and/or PD-L2 system thus represent an alternative approach to suppress the immune response and provide treatments for various immune and inflammatory disorders.

There is therefore a need for therapies, which induce the PD-1 pathway, enhance suppressive function and provide treatments for immune and inflammatory disorders controlled by the PD-1/PD-L1 and/or PD-L2 system. In particular, there is a need for biological therapeutics, such as antibodies, which modulate the interaction between PD-1 and PD-L1 or PD-L2 without blocking such interaction.

BRIEF SUMMARY OF THE INVENTION

The present invention provides antibodies that specifically bind to human PD-1. In one aspect of the invention, the antibodies of the present invention do not block the interaction between PD-1 and PD-L1. In one aspect of the invention, the antibodies of the present invention enhance the interaction between PD-1 and PD-L1. In one aspect of the invention, the antibodies of the present invention activate the PD-1 signaling pathway. In one aspect of the invention, the antibodies of the present invention are anti-PD-1 agonist antibodies. The antibodies of the invention are useful, for example, for the treatment and/or prevention of diseases or disorders that can be alleviated by modulating the interaction between PD-1 and PD-L1, in particular by activating the PD-1 pathway.

In one aspect, the present invention provides an anti-PD-1 antibody, in particular a monoclonal anti-PD-1 antibody, for example a humanized monoclonal anti-PD-1 antibody, having one or more of the properties described herein below. In one aspect, an anti-PD-1 antibody of the present invention binds to purified recombinant human PD-1 at high affinity, for example 20 nM or less, for example 10 nM or less, for example 5 nM of less. In one aspect, an anti-PD-1 antibody of the present invention binds to purified recombinant cynomologus PD-1 at an affinity of 50 nM or less. In one aspect, an anti-PD-1 antibody of the present invention selectively binds to PD-1, in particular human PD-1. In one aspect, an antibody of the present invention does not bind to mouse, rat, or rabbit PD-1. In one aspect, an anti-PD-1 antibody of the present invention does not block the binding of PD-L1 to PD-1. In one aspect, an anti-PD-1 antibody of the present invention enhances the binding of PD-L1 to PD-1. In one aspect, an anti-PD-1 antibody of the present invention attenuates T cell activity in a functional cell assay, for example by inhibition of IFNγ production, inhibition of IL-17A production or inhibition of IL-21 production. In one aspect, an anti-PD-1 antibody of the present invention inhibits human cell accumulation in a mouse model and reduces the levels of human inflammatory cytokines in the mouse model. In one aspect, an anti-PD-1 antibody of the present invention has favorable pharmacokinetic properties. In one aspect, an anti-PD-1 antibody of the present invention has favorable biophysical properties, for example yield, quality, stability or solubility. In one aspect, the present invention provides antigen-binding fragments of an antibody of the present invention.

In one embodiment, the present invention provides an anti-PD-1 antibody or antigen-binding fragment thereof comprising:
  a heavy chain variable region comprising the amino acid sequence of SEQ ID NO: 43 (H-CDR1); the amino acid sequence of SEQ ID NO: 44 (H-CDR2); and the amino acid sequence of SEQ ID NO: 45 (H-CDR3), and
  a light chain variable region comprising the amino acid sequence of SEQ ID NO: 1 (L-CDR1); the amino acid sequence of SEQ ID NO: 2 (L-CDR2); and the amino acid sequence of SEQ ID NO: 3 (L-CDR3),
  or
  a heavy chain variable region comprising the amino acid sequence of SEQ ID NO: 43 (H-CDR1); the amino acid sequence of SEQ ID NO: 46 (H-CDR2); and the amino acid sequence of SEQ ID NO: 45 (H-CDR3), and
  a light chain variable region comprising the amino acid sequence of SEQ ID NO: 1 (L-CDR1); the amino acid sequence of SEQ ID NO: 2 (L-CDR2); and the amino acid sequence of SEQ ID NO: 3 (L-CDR3),
  or
  a heavy chain variable region comprising the amino acid sequence of SEQ ID NO: 47 (H-CDR1); the amino acid sequence of SEQ ID NO: 48 (H-CDR2); and the amino acid sequence of SEQ ID NO: 49 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3), or a heavy chain variable region comprising the amino acid sequence of SEQ ID NO: 50 (H-CDR1); the amino acid sequence of SEQ ID NO: 51 (H-CDR2); and the amino acid sequence of SEQ ID NO: 52 (H-CDR3), and a light chain variable region comprising the amino acid sequence of SEQ ID NO: 7 (L-CDR1); the amino acid sequence of SEQ ID NO: 8 (L-CDR2); and the amino acid sequence of SEQ ID NO: 9 (L-CDR3), or a heavy chain variable region comprising the amino acid sequence of SEQ ID NO: 53 (H-CDR1); the amino acid sequence of SEQ ID NO: 54 (H-CDR2); and the amino acid sequence of SEQ ID NO: 55 (H-CDR3), and a light chain variable region comprising the amino acid sequence of SEQ ID NO: 10 (L-CDR1); the amino acid sequence of SEQ ID NO: 11 (L-CDR2); and the amino acid sequence of SEQ ID NO: 12 (L-CDR3), or a heavy chain variable region comprising the amino acid sequence of SEQ ID NO: 56 (H-CDR1); the amino acid sequence of SEQ ID NO: 57 (H-CDR2); and the amino acid sequence of SEQ ID NO: 58 (H-CDR3), and a light chain variable region comprising the amino acid sequence of SEQ ID NO: 13 (L-CDR1); the amino acid sequence of SEQ ID NO: 14 (L-CDR2); and the amino acid sequence of SEQ ID NO: 15 (L-CDR3), or a heavy chain variable region comprising the amino acid sequence of SEQ ID NO: 59 (H-CDR1); the amino acid sequence of SEQ ID NO: 60 (H-CDR2); and the amino acid sequence of SEQ ID NO: 61 (H-CDR3), and a light chain variable region comprising the amino acid sequence of SEQ ID NO: 16 (L-CDR1); the amino acid sequence of SEQ ID NO: 17 (L-CDR2); and the amino acid sequence of SEQ ID NO: 18 (L-CDR3), or a heavy chain variable region comprising the amino acid sequence of SEQ ID NO: 62 (H-CDR1); the amino acid sequence of SEQ ID NO: 63 (H-CDR2); and the amino acid sequence of SEQ ID NO: 64 (H-CDR3), and a light chain variable region comprising the amino acid sequence of SEQ ID NO: 19 (L-CDR1); the amino acid sequence of SEQ ID NO: 20 (L-CDR2); and the amino acid sequence of SEQ ID NO: 21 (L-CDR3), or a heavy chain variable region comprising the amino acid sequence of SEQ ID NO: 65 (H-CDR1); the amino acid sequence of SEQ ID NO: 66 (H-CDR2); and the amino acid sequence of SEQ ID NO: 67 (H-CDR3), and a light chain variable region comprising the amino acid sequence of SEQ ID NO: 22 (L-CDR1); the amino acid sequence of SEQ ID NO: 23 (L-CDR2); and the amino acid sequence of SEQ ID NO: 24 (L-CDR3), or a heavy chain variable region comprising the amino acid sequence of SEQ ID NO: 68 (H-CDR1); the amino acid sequence of SEQ ID NO: 69 (H-CDR2); and the amino acid sequence of SEQ ID NO: 70 (H-CDR3), and a light chain variable region comprising the amino acid sequence of SEQ ID NO: 25 (L-CDR1); the amino acid sequence of SEQ ID NO: 26 (L-CDR2); and the amino acid sequence of SEQ ID NO: 27 (L-CDR3), or a heavy chain variable region comprising the amino acid sequence of SEQ ID NO: 71 (H-CDR1); the amino acid sequence of SEQ ID NO: 72 (H-CDR2); and the amino acid sequence of SEQ ID NO: 58 (H-CDR3), and a light chain variable region comprising the amino acid sequence of SEQ ID NO: 28 (L-CDR1); the amino acid sequence of SEQ ID NO: 14 (L-CDR2); and the amino acid sequence of SEQ ID NO: 29 (L-CDR3), or a heavy chain variable region comprising the amino acid sequence of SEQ ID NO: 73 (H-CDR1); the amino acid sequence of SEQ ID NO: 74 (H-CDR2); and the amino acid sequence of SEQ ID NO: 75 (H-CDR3), and a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3), or a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3),
or
a heavy chain variable region comprising the amino acid sequence of SEQ ID NO: 80 (H-CDR1); the amino acid sequence of SEQ ID NO: 81 (H-CDR2); and the amino acid sequence of SEQ ID NO: 82 (H-CDR3), and
a light chain variable region comprising the amino acid sequence of SEQ ID NO: 33 (L-CDR1); the amino acid sequence of SEQ ID NO: 14 (L-CDR2); and the amino acid sequence of SEQ ID NO: 34 (L-CDR3),
or
a heavy chain variable region comprising the amino acid sequence of SEQ ID NO: 83 (H-CDR1); the amino acid sequence of SEQ ID NO: 84 (H-CDR2); and the amino acid sequence of SEQ ID NO: 85 (H-CDR3), and
a light chain variable region comprising the amino acid sequence of SEQ ID NO: 16 (L-CDR1); the amino acid sequence of SEQ ID NO: 35 (L-CDR2); and the amino acid sequence of SEQ ID NO: 36 (L-CDR3),
or
a heavy chain variable region comprising the amino acid sequence of SEQ ID NO: 86 (H-CDR1); the amino acid sequence of SEQ ID NO: 87 (H-CDR2); and the amino acid sequence of SEQ ID NO: 88 (H-CDR3), and
a light chain variable region comprising the amino acid sequence of SEQ ID NO: 37 (L-CDR1); the amino acid sequence of SEQ ID NO: 38 (L-CDR2); and the amino acid sequence of SEQ ID NO: 39 (L-CDR3),
or
a heavy chain variable region comprising the amino acid sequence of SEQ ID NO: 89 (H-CDR1); the amino acid sequence of SEQ ID NO: 90 (H-CDR2); and the amino acid sequence of SEQ ID NO: 91 (H-CDR3), and
a light chain variable region comprising the amino acid sequence of SEQ ID NO: 40 (L-CDR1); the amino acid sequence of SEQ ID NO: 41 (L-CDR2); and the amino acid sequence of SEQ ID NO: 42 (L-CDR3).

In one embodiment, the present invention provides an anti-PD-1 antibody or antigen-binding fragment comprising:
a heavy chain variable region comprising the amino acid sequence of SEQ ID NO: 73 (H-CDR1); the amino acid sequence of SEQ ID NO: 74 (H-CDR2); and the amino acid sequence of SEQ ID NO: 75 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3).

In one embodiment, the present invention provides an anti-PD-1 antibody or antigen-binding fragment comprising:
a heavy chain variable region comprising any one of:
the amino acid sequence SEQ ID NO: 73 (H-CDR1); the amino acid sequence of SEQ ID NO: 74 (H-CDR2); and the amino acid sequence of SEQ ID NO: 75 (H-CDR3), the amino acid sequence SEQ ID NO: 73 (H-CDR1); the amino acid sequence of SEQ ID NO: 76 (H-CDR2); and the amino acid sequence of SEQ ID NO: 77 (H-CDR3), the amino acid sequence SEQ ID NO: 73 (H-CDR1); the amino acid sequence of SEQ ID NO: 78 (H-CDR2); and the amino acid sequence of SEQ ID NO: 77 (H-CDR3), or the amino acid sequence SEQ ID NO: 73 (H-CDR1); the amino acid sequence of SEQ ID NO: 79 (H-CDR2); and the amino acid sequence of SEQ ID NO: 77 (H-CDR3);

and a light chain variable region comprising any one of:

the amino acid sequence of SEQ ID NO: 30 (L-CDR1); the amino acid sequence of SEQ ID NO: 31 (L-CDR2); and the amino acid sequence of SEQ ID NO: 32 (L-CDR3), the amino acid sequence of SEQ ID NO: 164 (L-CDR1); the amino acid sequence of SEQ ID NO: 31 (L-CDR2); and the amino acid sequence of SEQ ID NO: 32 (L-CDR3), the amino acid sequence of SEQ ID NO: 165 (L-CDR1); the amino acid sequence of SEQ ID NO: 166 (L-CDR2); and the amino acid sequence of SEQ ID NO: 32 (L-CDR3), the amino acid sequence of SEQ ID NO: 165 (L-CDR1); the amino acid sequence of SEQ ID NO: 167 (L-CDR2); and the amino acid sequence of SEQ ID NO: 32 (L-CDR3).

In one embodiment, the CDRs of the anti-PD-1 antibody or antigen-binding fragment thereof are defined per the Chemical Computing Group (CCG) numbering.

In one embodiment, the present invention provides an anti-PD1 antibody or antigen-binding fragment thereof as set forth above, wherein the antibody or antigen-binding fragment thereof is a humanized antibody or antigen-binding fragment thereof.

In one embodiment, the present invention provides an anti-PD1 antibody or antigen-binding fragment thereof as set forth above, wherein the antibody or antigen-binding fragment thereof is selected from the group consisting of a monoclonal antibody, a Fab, a F(ab')2, a Fv and an scFv.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 108 and SEQ ID NO: 92, respectively; SEQ ID NO: 109 and SEQ ID NO: 93, respectively; SEQ ID NO: 110 and SEQ ID NO: 94, respectively; SEQ ID NO: 111 and SEQ ID NO: 95, respectively; SEQ ID NO: 112 and SEQ ID NO: 96, respectively; SEQ ID NO: 113 and SEQ ID NO: 97, respectively; SEQ ID NO: 114 and SEQ ID NO: 98, respectively; SEQ ID NO: 115 and SEQ ID NO: 99, respectively; SEQ ID NO: 116 and SEQ ID NO: 100, respectively; SEQ ID NO: 117 and SEQ ID NO: 101, respectively; SEQ ID NO: 118 and SEQ ID NO: 102, respectively; SEQ ID NO: 119 and SEQ ID NO: 103, respectively; SEQ ID NO: 120 and SEQ ID NO: 104, respectively; SEQ ID NO: 121 and SEQ ID NO: 105, respectively; SEQ ID NO: 122 and SEQ ID NO: 106, respectively; SEQ ID NO: 123 and SEQ ID NO: 107, respectively.

In one embodiment, the present invention provides an anti-PD1 antibody or antigen-binding fragment thereof, wherein the antibody or antigen-binding fragment thereof comprises a heavy chain variable region comprising the amino acid sequence of any one of SEQ NO: 131, SEQ NO: 133, SEQ NO: 135, SEQ NO: 137 or SEQ NO: 139 and a light chain variable region comprising the amino acid sequence of any one of SEQ NO: 125, SEQ NO: 127 or SEQ NO: 129.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 131 and SEQ ID NO: 125, respectively.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 133 and SEQ ID NO: 127, respectively.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 135 and SEQ ID NO: 127, respectively.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 137 and SEQ ID NO: 129, respectively.

In one embodiment, the present invention provides an anti-PD1 antibody or antigen-binding fragment thereof, wherein the antibody or antigen-binding fragment thereof comprises a heavy chain variable region and a light chain variable region comprising the amino acid sequences of SEQ ID NO: 139 and SEQ ID NO: 129, respectively.

In one embodiment, the present invention provides an anti-PD1 antibody or antigen-binding fragment thereof, wherein the antibody or antigen-binding fragment thereof comprises a heavy chain variable region and a light chain variable region having at least 90%, at least 95%, at least 98%, or at least 99% identity to the amino acid sequences of SEQ ID NO: 131 and SEQ ID NO: 125, respectively.

In one embodiment, the present invention provides an anti-PD1 antibody or antigen-binding fragment thereof, wherein the antibody or antigen-binding fragment thereof comprises a heavy chain variable region and a light chain variable region having at least 90%, at least 95%, at least 98%, or at least 99% identity to the amino acid sequences of SEQ ID NO: 133 and SEQ ID NO: 127, respectively.

In one embodiment, the present invention provides an anti-PD1 antibody or antigen-binding fragment thereof, wherein the antibody or antigen-binding fragment thereof comprises a heavy chain variable region and a light chain variable region having at least 90%, at least 95%, at least 98%, or at least 99% identity to the amino acid sequences of SEQ ID NO: 135 and SEQ ID NO: 127, respectively.

In one embodiment, the present invention provides an anti-PD1 antibody or antigen-binding fragment thereof, wherein the antibody or antigen-binding fragment thereof comprises a heavy chain variable region and a light chain variable region having at least 90%, at least 95%, at least 98%, or at least 99% identity to the amino acid sequences of SEQ ID NO: 137 and SEQ ID NO: 129, respectively.

In one embodiment, the present invention provides an anti-PD1 antibody or antigen-binding fragment thereof, wherein the antibody or antigen-binding fragment thereof comprises a heavy chain variable region and a light chain variable region having at least 90%, at least 95%, at least 98%, or at least 99% identity to the amino acid sequences of SEQ ID NO: 139 and SEQ ID NO: 129, respectively.

In one embodiment, the present invention provides an anti-PD1 antibody or antigen-binding fragment thereof as described above, wherein the antibody comprises a heavy chain constant region selected from the group consisting of IgG1, IgG2, IgG3, IgG4, IgM, IgA and IgE constant regions, for example human IgG1, IgG2, IgG3, IgG4, IgM, IgA or IgE.

In one embodiment, the present invention provides an anti-PD1 antibody as described above, wherein the heavy chain constant region is a heavy chain constant region of an IgG4 with a Ser228Pro mutation.

In one embodiment, the present invention provides an anti-PD1 antibody as described above, wherein the heavy chain constant region is a heavy chain constant region of an IgG1.

In one embodiment, the present invention provides an anti-PD1 antibody as described above, wherein the heavy chain constant region is a heavy chain constant region of an IgG1 with Leu234Ala and Leu235Ala mutations.

In one embodiment, the present invention provides an anti-PD1 antibody or antigen-binding fragment thereof as described above wherein the antibody or antigen-binding fragment thereof comprises a light chain constant region selected from the group consisting of kappa and lambda.

In one embodiment, the present invention provides an anti-PD1 antibody, wherein the antibody comprises a heavy chain and a light chain comprising the amino acid sequences of SEQ ID NO: 143 and SEQ ID NO: 141, respectively.

In one embodiment, the present invention provides an anti-PD1 antibody, wherein the antibody comprises a heavy chain and a light chain comprising the amino acid sequences of SEQ ID NO: 147 and SEQ ID NO: 145, respectively.

In one embodiment, the present invention provides an anti-PD1 antibody, wherein the antibody comprises a heavy chain and a light chain comprising the amino acid sequences of SEQ ID NO: 149 and SEQ ID NO: 145, respectively.

In one embodiment, the present invention provides an anti-PD1 antibody, wherein the antibody comprises a heavy chain and a light chain comprising the amino acid sequences of SEQ ID NO: 153 and SEQ ID NO: 151, respectively.

In one embodiment, the present invention provides an anti-PD1 antibody, wherein the antibody comprises a heavy chain and a light chain comprising the amino acid sequences of SEQ ID NO: 155 and SEQ ID NO: 151, respectively.

In one embodiment, the present invention provides an anti-PD1 antibody, wherein the antibody comprises a heavy chain and a light chain, wherein the amino acid sequence of said heavy chain consists of the amino acids of SEQ ID NO: 143 and the amino acid sequence of said light chain consists of the amino acids of SEQ ID NO:141.

In one embodiment, the present invention provides an anti-PD1 antibody, wherein the antibody comprises a heavy chain and a light chain, wherein the amino acid sequence of said heavy chain consists of the amino acids of SEQ ID NO: 147 and the amino acid sequence of said light chain consists of the amino acids of SEQ ID NO:145.

In one embodiment, the present invention provides an anti-PD1 antibody, wherein the antibody comprises a heavy chain and a light chain, wherein the amino acid sequence of said heavy chain consists of the amino acids of SEQ ID NO: 149 and the amino acid sequence of said light chain consists of the amino acids of SEQ ID NO:145.

In one embodiment, the present invention provides an anti-PD1 antibody, wherein the antibody comprises a heavy chain and a light chain, wherein the amino acid sequence of said heavy chain consists of the amino acids of SEQ ID NO: 153 and the amino acid sequence of said light chain consists of the amino acids of SEQ ID NO:151.

In one embodiment, the present invention provides an anti-PD1 antibody, wherein the antibody comprises a heavy chain and a light chain, wherein the amino acid sequence of said heavy chain consists of the amino acids of SEQ ID NO: 155 and the amino acid sequence of said light chain consists of the amino acids of SEQ ID NO:151.

In one embodiment, an anti-PD1 antibody or antigen-binding fragment thereof as described above is a monoclonal antibody or antigen-binding fragment thereof.

In one embodiment, an anti-PD1 antibody or antigen-binding fragment thereof as described above is a humanized antibody or antigen-binding fragment thereof.

In one embodiment, an anti-PD1 antibody or antigen-binding fragment thereof as described above is an agonist anti-PD1 antibody or antigen-binding fragment thereof.

In one embodiment, an anti-PD1 antibody or antigen-binding fragment thereof as described above binds to human PD-1 at high affinity, for example 20 nM of less, for example 10 nM or less, for example 5 nM of less.

In one embodiment, the present invention provides an anti-PD1 antibody or antigen-binding fragment thereof that competes for binding to PD-1 with an anti-PD-1 antibody or antigen-binding fragment thereof as described above. In one embodiment, the present invention provides an anti-PD-1 antibody or antigen-binding fragment thereof that competes for binding to PD-1 with Antibody A, Antibody B, Antibody C, Antibody D or Antibody E.

In one embodiment, the present invention provides a pharmaceutical composition comprising an anti-PD-1 antibody or antigen-binding fragment thereof as described above, and a pharmaceutically acceptable excipient.

In one embodiment, the present invention provides an anti-PD-1 antibody or antigen-binding fragment thereof as described above for use as a medicament.

In one embodiment, the present invention provides a method of treating a PD-1 pathway disorder comprising administering to a patient in need thereof a pharmaceutically effective amount of the anti-PD-1 antibody or antigen-binding fragment thereof as described above. In one embodiment, the present invention provides an anti-PD-1 antibody or antigen-binding fragment thereof as described above for use in treating a PD-1 pathway disorder. In one embodiment, the present invention provides the use of the anti-PD-1 antibody or antigen-binding fragment thereof as described above in manufacture of a medicament for treating a PD-1 pathway disorder.

In one embodiment, the present invention provides a method of modulating the interaction between PD-1 and PD-L1 in a human patient comprising administering to the human patient a composition comprising an anti-PD-1 antibody or the antigen-binding fragment as described above in an amount sufficient to activate the PD-1 pathway in the human patient. In one embodiment, the present invention provides an anti-PD-1 antibody or the antigen-binding fragment as described above for use in modulating the interaction between PD-1 and PD-L1 in a human patient. In one embodiment, the present invention provides the use of an anti-PD-1 antibody or the antigen-binding fragment as described above in the manufacture of a medicament for modulating the interaction between PD-1 and PD-L1 in a human patient.

In one embodiment, the present invention provides a method of attenuating PD-1 expressing T cell activity in a human patient comprising administering to the human patient a composition comprising an anti-PD-1 antibody or the antigen-binding fragment as described above in an amount sufficient to down-modulate an immune response in the human patient. In one embodiment, the present invention provides an anti-PD-1 antibody or the antigen-binding fragment as described above for use in attenuating PD-1 expressing T cell activity in a human patient. In one embodiment, the present invention provides the use of an anti-PD-1 antibody or the antigen-binding fragment as described above in the manufacture of a medicament for attenuating PD-1 expressing T cell activity in a human patient.

In one embodiment, in a method above, in an anti-PD-1 antibody or antigen-binding fragment thereof for use above, or in the use of an anti-PD-1 antibody or antigen-binding fragment thereof above, the disease is selected from the group consisting of systemic sclerosis (SSc), systemic lupus erythematosus, polymyositis, giant cell arteritis, psoriasis, psoriatic arthritis, ankylosing spondylitis and inflammatory bowel disease.

In one embodiment, in the method above, in the anti-PD-1 antibody or antigen-binding fragment thereof for use above, or in the use of the anti-PD-1 antibody or antigen-binding fragment thereof above, the antibody or antigen-binding fragment thereof is administered by a parenteral route, intravenous route or subcutaneous route of administration.

In one embodiment, the present invention provides an isolated polynucleotide encoding a heavy chain variable region amino and/or a light chain variable region as described above.

In one embodiment, the present invention provides an isolated polynucleotide encoding a heavy chain and/or a light chain as described above.

In one embodiment, the present invention provides an expression vector comprising a polynucleotide as described above.

In one embodiment, the present invention provides a host cell comprising an expression vector as described above. In one embodiment, the host cell is a mammalian cell.

In one embodiment, the present invention provides a method of manufacturing an antibody comprising the steps of:
culturing a host cell comprising an expression vector comprising an isolated polynucleotide encoding a heavy chain variable region as described above and an expression vector comprising polynucleotide encoding light chain variable region as described above under conditions that allow formation of an antibody, and recovering said antibody.

In one embodiment, the present invention provides a method of manufacturing an antibody comprising the steps of:
culturing a host cell comprising an expression vector comprising an isolated polynucleotide encoding a heavy chain as described above and an expression vector comprising polynucleotide encoding light chain as described above under conditions that allow formation of an antibody; and recovering said antibody.

In one embodiment, a method above further comprises the step of purifying the antibody. In one embodiment, a method above further comprises the step of formulating the antibody into a pharmaceutical composition.

In one embodiment, the present invention provides a multi-specific antibody comprising a first anti-PD-1 agonist antigen-binding site and a second antigen-binding site.

In one embodiment, the second antigen-binding site is an anti-CD48 binding site, an anti-CD-2 binding site, an anti-CD11a binding site or an anti-CD3 binding site.

In one embodiment, the first anti-PD-1 agonist antigen-binding site comprises a heavy chain variable region and a light chain variable region as described above.

In one embodiment, the multi-specific antibody is a bi-specific antibody.

BRIEF DESCRIPTION OF THE DRAWINGS

In FIG. 3D, the individual data points are only depicted for Antibody C; the individual data points for the other antibodies are not depicted in FIG. 3D because of their close proximity to each other. POC stands for "percentage of control".

DETAILED DESCRIPTION OF THE INVENTION

Figure 1:
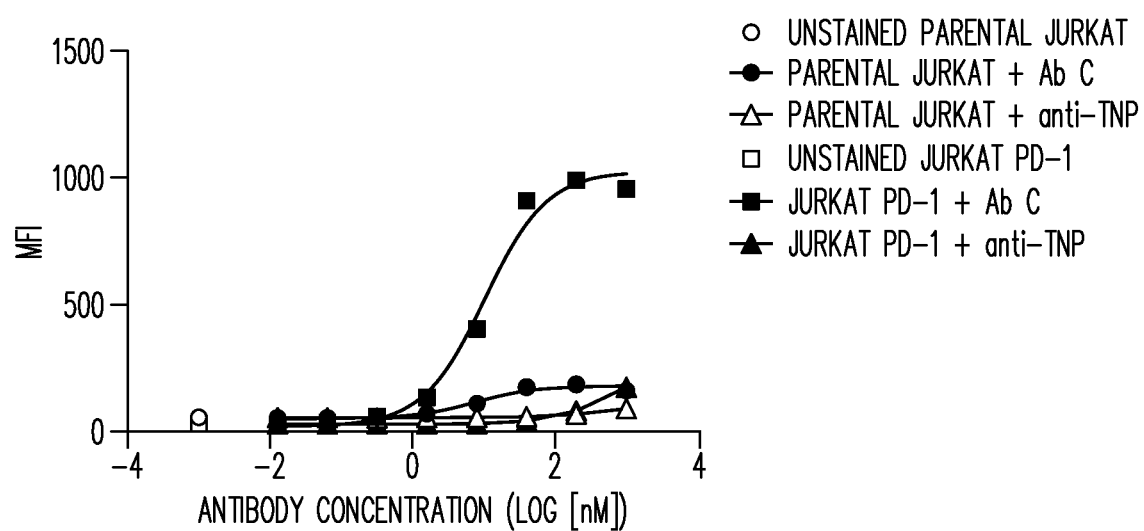
FIG. 1: Selectivity of anti-PD-1 antibody to human PD-1 protein in a cell-based assay evaluated by flow cytometry. MFI stands for "mean fluorescence intensity".

The present invention addresses the need for treatments for immune and inflammatory disorders, in particular immune and inflammatory disorders controlled by the PD-1/PD-L1 and/or PD-L2 system. To address this need, the present invention provides anti-PD-1 antibodies, which do not block the interaction between PD-1 and PD-L1. In one aspect, the present invention provides antibodies, which enhance the interaction between PD-1 and PD-L1. In one aspect of the invention, the antibodies of the present invention activate the PD-1 signaling pathway. In one aspect, the antibodies of the present invention are anti-PD-1 agonist antibodies. PD-1 agonism restores immune balance by inhibiting expansion and effector function of auto-reactive T cells in human diseases where PD-1 is expressed but may not be engaged, or optimally engaged by its ligands. In one aspect, the antibodies of the present invention are useful in treating in immune and inflammatory disorders and transplant rejection. For example, the antibodies of the present invention are useful for the treatment and/or prevention of diseases or disorders that can be alleviated by modulating the interaction between PD-1 and PD-L1, in particular by activating the PD-1 pathway. In one aspect, antibodies of the present invention are useful in treating and/or preventing systemic sclerosis (SSc), systemic lupus erythematosus, polymyositis, giant cell arteritis, psoriasis, psoriatic arthritis, ankylosing spondylitis or inflammatory bowel disease.

In one aspect, the present invention provides an anti-PD-1 antibody, in particular a monoclonal anti-PD-1 antibody, for example a humanized monoclonal anti-PD-1 antibody, having one or more of the properties described herein below. In one aspect, an anti-PD-1 antibody of the present invention binds to purified recombinant human PD-1 at high affinity, for example 20 nM or less, for example 10 nM or less, for example 5 nM of less. In one aspect, an anti-PD-1 antibody of the present invention binds to purified recombinant cynomologus PD-1 at an affinity of 50 nM or less. In one aspect, an anti-PD-1 antibody of the present invention selectively binds to PD-1, in particular human PD-1. In one aspect, an antibody of the present invention does not bind to mouse, rat, or rabbit PD-1. In one aspect, an anti-PD-1 antibody of the present invention does not block the binding of PD-L1 to PD-1. In one aspect, an anti-PD-1 antibody of the present invention enhances the binding of PD-L1 to PD-1. In one aspect, an anti-PD-1 antibody of the present invention attenuates T cell activity in several functional cell assays as shown herein below, for example by inhibition of IFNγ production, inhibition of IL-17A production or inhibition of IL-21 production. In one aspect, an anti-PD-1 antibody of the present invention inhibits human cell accumulation in a mouse model and reduces the levels of human inflammatory cytokines in the mouse model. In one aspect, an anti-PD-1 antibody of the present invention has favorable pharmacokinetic properties. In one aspect, an anti-PD-1 antibody of the present invention has favorable biophysical properties, for example yield, quality, stability or solubility. These properties are for example shown in the Examples herein below.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663, Vargas-Madrazo E, Paz-García E. J Mol Recognit. 2003; 16(3):113-120). The variable domains are also referred herein as variable regions, and the constant domains as constant regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, $5^{th}$ Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. An alternative definition of the CDRs is per the Chemical Computing Group (CCG) numbering (Almagro et al., Proteins 2011; 79:3050-3066 and Maier et al, Proteins 2014; 82:1599-1610). The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are generally not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-PD-1 antibody", "humanized anti-PD-1 antibody", and "variant humanized anti-PD-1 antibody" are used herein in the broadest sense and specifically encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., PD-1 binding.

The term "monoclonal antibody" (mAb) refers to an antibody of a population of substantially homogeneous antibodies; that is, the individual antibodies in that population are identical except for naturally occurring mutations or possible well-known alterations such as removal of C-terminal lysine from the antibody heavy chain or post-translational modifications such as amino acid isomerization or deamidation, methionine oxidation or asparagine or glutamine deamidation that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms "antibody fragment", "antigen binding fragment", "anti-PD-1 antibody fragment", "humanized anti-PD-1 antibody fragment", "variant humanized anti-PD-1 antibody fragment" refer to a portion of a full length anti-PD-1 antibody, in which a variable region or a functional capability is retained, for example, specific PD-1 epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Antibody fragments can be obtained for example by treating full-length antibodies treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a F(ab')$_2$ fragment that has two antigen-binding sites and is still capable of cross-linking antigen.

Another example of antibody fragments according to the invention are Fab' fragments. Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

A "Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

Antibody fragments may also include "Single-chain Fv" or "scFv" fragments. A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Antibody fragments may also form tandem Fd segments, which comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

In one aspect, an anti-PD-1 antibody of the invention is a humanized antibody or antibody fragment. A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. Methods of humanization of antibodies are for example described by Almagro et al., (2008) Frontiers in Bioscience 13, 1619-1633, or in WO12092374 A2.

The present invention describes specific humanized anti-PD-1 antibodies which contain CDRs derived from the mouse lead 723C2 inserted between the FRs of human germline sequence heavy and light chain variable domains. Additionally, a cysteine in the heavy chain CDR3 of mouse lead 723C2 was replaced with a tyrosine in the humanized anti-PD-1 antibodies derived from mouse lead 723C2 ("DC" to "DY").

In one aspect, a humanized anti-PD-1 antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, the CDRs are murine sequences of the mouse lead 723C2 and the FRs are those of a human immunoglobulin consensus or germline sequence. In another aspect, a humanized anti-PD-1 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-PD-1 antibody according to the invention can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibits cytotoxic activity, and the isotype is typically $IgG_1$. Where such cytotoxic activity is not desirable, the constant domain may be of another isotype, e.g., $IgG_2$. An alternative humanized anti-PD-1 antibody can comprise sequences from more than one immunoglobulin class or isotype, and selecting particular constant domains to optimize desired effector functions is within the ordinary skill in the art.

In one aspect, the constant domain of an antibody of the present invention is IgG4Pro, which has one replacement mutation (Ser228Pro) that prevents Fab-arm exchanging. This Ser to Pro mutation is in the hinge region of the IgG4 backbone and is commonly known as Ser228Pro, although its position in the heavy chain may vary by a few amino acids, for example depending on the length of the variable region and/or difference of the hinge length between IgG1 and IgG4. The Ser to Pro mutation in the hinge region (Cys-Pro-Ser-Cys-Pro) is referred herein as "Ser228Pro", independently of its position in the heavy chain. In another aspect, the constant domain of an antibody of the present invention is IgG1KO, which has two mutations in the hinge region, Leu234Ala and Leu235Ala, to reduce effector function (ADCC).

The FRs and CDRs, or HVLs, of a humanized anti-PD-1 antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to PD-1. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-PD-1 antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody, for example purified to at least greater than 95%, 96%, 97%, 98%, or 99%.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" as used according to the invention refers to factors/properties that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half-life of the antibody.

The term "agonist antibody" or "agonistic antibody" as used according to the invention refers to an antibody, which upon binding to PD-1, induces at least one biological activity that is induced by PD-1 ligand PD-L1. In one aspect, the induction is statistically significant when compared to the induction in the absence of the agonist antibody. In one aspect, the antibody is an agonist antibody when the at least one biological activity is induced by at least about 20%, 30%, 40%, 45%, 50%, 55%, 60%, 65%, 70%, 75%, 80%, 85%, 90%, 95%, or 100% greater than in the absence of the agonist antibody, for example when measured as in one of the Examples described herein below. In some embodiments, an "agonist antibody" enhances the interaction between PD-1 and PD-L1. Exemplary assays for detecting PD-1 agonist properties are described herein or are known in the art.

"Multispecific" refers to a protein, such as an antibody, that specifically binds two or more distinct antigens or two or more distinct epitopes within the same antigen.

"Bispecific" refers to a protein, such as an antibody, that specifically binds two distinct antigens or two distinct epitopes within the same antigen.

In some embodiments, the antibody that specifically binds PD-1 or the antigen-binding fragment thereof of the invention is a bispecific antibody. In some embodiments, the antibody or the antigen-binding fragment thereof of the invention is a multispecific antibody. The monospecific antibodies that specifically bind PD-1 provided herein may be engineered into bispecific antibodies, which are also encompassed within the scope of the invention.

Full-length bispecific antibodies may be generated for example using Fab arm exchange (e.g., half-molecule exchange, exchanging one heavy chain-light chain pair) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond Bispecific antibodies may also be generated using designs such as the Triomab/Quadroma (Trion Pharma/Fresenius Biotech), Knob-in-Hole (Genentech), CrossMAbs (Roche) and the electrostatically-induced CH3 interaction (Chugai, Amgen, NovoNordisk, Oncomed), the LUZ-Y (Genentech), the Strand Exchange Engineered Domain body (SEEDbody) (EMD Serono), the Biclonic (Merus) and as DuoBody® Products (Genmab A/S).

For example, a bispecific PD-1/CD2, a bispecific PD-1/CD48, a bispecific PD-1/CD11a or a PD-1/CD3 antibody can be generated using the VH/VL domains of the PD-1 antibodies described herein or any VH/VL regions of published anti-PD-1 agonist antibodies and any VH/VL regions of published anti-CD2, anti-CD48, anti-CD11a or anti-CD3 antibodies, respectively.

Another embodiment of the invention is a bispecific antibody comprising a first domain that binds PD-1 and a second domain that binds CD2, CD48, CD11a or CD3.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers, which may for example have been transfected with one or more expression vectors encoding one or more amino acids sequences of an antibody or antigen binding fragment thereof of the present invention.

The term "mammal" for purposes of treatment according to the invention refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with an anti-PD-1 antibody described herein, in particular a humanized anti-PD-1 antibody described herein. This includes chronic and acute disorders or diseases including those pathological conditions that predispose the mammal to the disorder in question.

As used herein, the term "PD-1 pathway disorder" or "PD-1 pathway disease" refers to a condition, which can be alleviated by modulating the interaction between PD-1 and PD-L1, in particular by activating the PD-1 pathway. A "PD-1 pathway disorder" or "PD-1 pathway disease" includes T-cell associated diseases where PD-1 is expressed, A "PD-1 pathway disorder" or "PD-1 pathway disease" also includes conditions characterized by activated auto-reactive T cells that express PD-1 and are drivers of chronic inflammation and autoimmune disease and in which attenuation of PD-1 expressing T cell activity and/or downmodulation of immune response is desired. Examples of PD-1 pathway disorders include diseases or disorders such as systemic sclerosis (SSc), systemic lupus erythematosus, polymyositis, giant cell arteritis, psoriasis, psoriatic arthritis, ankylosing spondylitis and inflammatory bowel disease.

The term "specifically binds," or the like, means that an anti-PD-1 antibody or antigen-binding fragment thereof forms a complex with an antigen that is relatively stable under physiologic conditions. Methods for determining whether two molecules specifically bind are described herein or a known in the art and include, for example, equilibrium dialysis, surface plasmon resonance, and the like. In one embodiment, specific binding is characterized by a $K_D$ of about $1\times10^{-7}$ M (100 nM) or less according to the Affinity Binding method described in the Examples section herein. In another embodiment, specific binding is characterized by a $K_D$ of about $5\times10^{-8}$ M (50 nM) or less according to the Affinity Binding method described in the Examples section herein. In another embodiment, specific binding is characterized by a $K_D$ of about $1\times10^{-8}$ M (10 nM) or less according to the Affinity Binding method described in the Examples section herein. In another embodiment, specific binding is characterized by a $K_D$ of about $5\times10^{-9}$ M (5 nM) or less according to the Affinity Binding method described in the Examples section herein. An isolated antibody that specifically binds human PD-1 may, however, have cross-reactivity to other antigens, such as PD-1 molecules from other species. Moreover, an isolated antibody may be substantially free of other cellular material and/or chemicals.

The term "subcutaneous administration" refers to introduction of a drug, for example an anti-PD-1 antibody or antigen-binding fragment thereof of the invention, under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug, for example an anti-PD-1 antibody or antigen-binding fragment thereof of the invention, under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue. For example, "subcutaneous bolus" refers to the administration of an anti-PD-1 antibody or antigen-binding fragment thereof of the invention to a human patient in less than approximately 15 minutes; in another aspect, less than 5 minutes, and in still another aspect, less than 60 seconds The term "therapeutically effective amount" is used to refer to an amount of an anti-PD-1 antibody or antigen-binding fragment thereof that relieves or ameliorates one or more of the symptoms of the disorder being treated. In doing so, it is that amount that has a beneficial patient outcome. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-PD-1 antibody or antigen-binding fragment thereof prior to or following the onset of a symptom of a disease or disorder thereby preventing or removing one or more signs of the disease or disorder. As another example, the term includes the administration of an anti-PD-1 antibody or antigen-binding fragment thereof after clinical manifestation of the disease to combat the symptoms of the disease. Further, administration of an anti-PD-1 antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-PD-1 antibody composition or antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are anti-PD-1 antibodies, in particular humanized anti-PD-1 antibodies, as well as compositions and articles of manufacture comprising anti-PD-1 antibodies of the present invention. Also described are antigen-binding fragments of an anti-PD-1 antibody. The anti-PD-1 antibodies and antigen-binding fragments thereof can be used in the treatment of a variety of diseases or disorders, in particular diseases or disorders characterized by activated auto-reactive T cells that express PD-1 and are drivers of chronic inflammation and autoimmune disease. An anti-PD-1 antibody and an antigen-binding fragment thereof each include at least a portion that specifically recognizes a PD-1 epitope. In one aspect, the anti-PD-1 antibodies of the present invention and antigen-binding fragments thereof are agonist anti-PD-1 antibodies and antigen-binding fragment thereof.

The generation of anti-PD-1 antibodies according to the invention and their characterization is described in the Examples. In an initial characterization, the anti-PD-1 chimeric lead 723C2 was selected based on its superior antibody performance, as for example described in the Examples below. A library of variants was generated by placing the CDRs of the chimeric lead into FRs of the human consensus heavy and light chain variable domains and furthermore by engineering the FRs with different alterations. Additionally, a cysteine in the heavy chain CDR3 of mouse lead 723C2 was replaced with a tyrosine in the humanized anti-PD-1 antibodies derived from mouse lead 723C2 ("DC" to "DY"). The change from "DC" to "DY" did not have an impact on the pharmacological properties of the antibodies. The process for the production of humanized antibodies is described in the Examples.

The amino acid sequences of variable regions of representative mouse leads are shown in Tables 1 and 2. The CDR regions of these mouse leads and the CDR regions of engineered variants of lead 723C2 are shown in Tables 3 and 4.

TABLE 1

| Anti-PD-1 Mouse Leads-VK Sequences | |
|---|---|
| 306E6VK | EIVMTQAAFSNPVTLGTSASISCRSSKSLLHRNGITYLYWYLQKPGQSP<br>QLLIYEMSNLASGVPDRFSSSGSGTDFTLRISRVEAEDVGVYYCGQNLE<br>FPLTFGAGTKLELK<br>(SEQ ID NO: 92) |
| 307A3VK | EIVMTQAAFSNPVTLGTSASISCRSSKSLLHRNGITYLYWYLQKPGQSP<br>QLLIYEMSNLASGVPDRFSGSGSGTDFTLRISRVEAEDVGVYYCGQNLE<br>FPLTFGAGTKLELK<br>(SEQ ID NO: 93) |
| 313C12VK | DIVMTQSQKFMSTTVGDRVSITCKASQNVGTAVAWYQQKPGQSPKLLIY<br>SVSNRYTGVPDRFTGSGSGTDFTLTISNMQSEDLADYFCQQYSSYPFTF<br>GAGTKLELK<br>(SEQ ID NO: 94) |
| 414A12VK | DILMTQSPSSMSVSLGDTVSITCHASQGINNNIGWLQQKPGKSFKGLIY<br>HKSNLEDGVPSRFSGSGSGADYSLTISSLESEDFADYYCVQYAQFPYTF<br>GGGTKLEIK<br>(SEQ ID NO: 95) |
| 502H1VK | DIVMTQAAFYNPVTLGTSASISCRSSKSLLHRNGITYLYWYLQKPGQSP<br>QLLIYQMSNLASGVPDRFSSSGSGADFTLRISRVEAEDVGVYYCAQNLE<br>LPLTFGAGTKLELK<br>(SEQ ID NO: 96) |
| 701C1VK | DIVMSQSPSSLAVSVGEKVTMTCKSSQSLLYSSNQKNYLAWYQQKPGQS<br>PKLLIYWASTRESGVPDRFTGSGSGTDFTLTISSVKAEDLAVYYCHQYY<br>SSPLTFGAGTKLELK<br>(SEQ ID NO: 97) |
| 701E9VK | DIQMTQSPSSLSASLGERVSLTCRASQEISGYLSWLQQKPDGTIKRLIY<br>AASTLDSGVPKRFSGSRSGSDYSLTISSLESEDFADYYCLQYASYPLTF<br>GAGTKLELK<br>(SEQ ID NO: 98) |

TABLE 1-continued

Anti-PD-1 Mouse Leads-VK Sequences

| | |
|---|---|
| 703D10VK | QIVLTQSPGIMSASPGEKVTITCSANSSVSFMHWFQQKPGTSPKIWIYS<br>TSSLASGVPARFSGSGSGTSYSLTISRMEAEDAATYYCQQRSSYPLTFG<br>AGTKLELK<br>(SEQ ID NO: 99) |
| 708E4VK | DIVMTQSQKFLSTSVGDRVRVTCKASQNVVTYVAWYQQKPGQSPKSLIY<br>SASYRYSGVPDRFTGSGSGTYFTLTINNVQFEDLAEYFCQQYHSYPYTF<br>GGGTKLEIK<br>(SEQ ID NO: 100) |
| 709A6VK | DIVLTQSPASLAVSLGQRATISCRASESVDIYGISFLHWYQQKPGQPPK<br>HLIYRASNLDSGIPARFSGSGSRTDFTLTINPVETDDVATYYCQQSNKD<br>PLTFGAGTKLELK<br>(SEQ ID NO: 101) |
| 718C2VK | DIVMSQSPSSLTVSVGEKVTMSCKSSQSLLYSSNQKIYLAWFQQKPGQS<br>PKLLIYWASTRESGVPDRFTGSGSGTDFTLTISSVKAEDLAVYYCQQYY<br>NSPLTFGAGTKLELK<br>(SEQ ID NO: 102) |
| 723C2VK | EIVLTQSPTTMAASPGEKITITCSASSSISSDYLHWYQQKPGFSPELLI<br>YRTSNLASGVPARFSGSGSGTSYSLTIGSMEAEDVATYYCQQGTSLPRA<br>FGGGTKLEIK<br>(SEQ ID NO: 103) |
| 803E6VK | DIVMTQSPSSLTVTAGEKVTMSCKSSQSLLHSGNQKNYMTWYQQKPGQP<br>PKLLIYWASTRESGVPDRFTGSGSGTDFTLTISSVQAEDLAVYYCQNDY<br>SYPLTFGAGTKLELK<br>(SEQ ID NO: 104) |
| 811G3VK | DIQMTQSPSSLSASPGERVSLTCRASQEISGYLSWLQQKPDGTIKRLIY<br>VASTLDSGVPKRFSGSRSGSDYSLTISSLESEDFADYYCLQYANYPYTF<br>GGGTKLEIK<br>(SEQ ID NO: 105) |
| 814E10VK | DIQMTQTTSSLSASLGDRVTISCSASQDIINYLNWYQQKPDGTVKLLIY<br>STSSLHSGVSLRFSGSGSGTDYSLTISNLEPEDVATYYCHQYSQLPYTF<br>GGGTKLEIK<br>(SEQ ID NO: 106) |
| 820C3VK | DIQMTQTTSSLSASLGDRVTISCSASQDIFNYLNWYQQKPDGTVKLLIY<br>YTSSLHSGVPSRFSGSGSGTDFSLTISNLEPEDIATYYCQQYSNLPYTF<br>GGGTKLEIK<br>(SEQ ID NO: 107) |

TABLE 2

Anti-PD-1 Mouse Leads-VH Sequences

| | |
|---|---|
| 306E6VH | EVQLQQSGPELVKPGSSVKISCKASGYTFTDYYVNWVKQSHGKSLEWFGD<br>IHPNSGDTTYNQKFKDKATLTVDKSSSTAYMELRSLTSEDSAVYYCARRR<br>YDYDGFAYWGQGTLVTVSA<br>(SEQ ID NO: 108) |
| 307A3VH | EVQLQQSGPELVKPGASVKISCKASGYTFTDYYVNWVKQSHGKSLEWFGD<br>IHPNNGGITYNQKFKGKASLTVDKSSSTAYMELRSLTSEDSAVYYCARRR<br>YDYDGFAYWGQGTLVTVSA<br>(SEQ ID NO: 109) |
| 313C12VH | EVQLVESGGGLVKPGGSLKLSCAASGFTFSDYGMHWVRQTPEKGLEWIAY<br>INSDSNTIYYADTVKGRFTISRDNARKTLYLQMTSLRSEDTAMYYCSPLV<br>APDYWGQGTTLTVSS<br>(SEQ ID NO: 110) |
| 414A12VH | QVQLQQPGAELVKPGASVKLSCKASGHTFTSNWIHWVKQRPGQGLEWIGE<br>IDPSDSYTYYNQKFKGKATLTVDKSSSTAYMQLSSLTSEDSAVYSCACPG<br>RNSNFAYWGQGTTLTVSS<br>(SEQ ID NO: 111) |
| 502H1VH | QVTLKESGPGILQPSQTLSLTCSFSGFSLSTSGMGVTWIRKPSGQGLEWL<br>AHIFWDGDKRYNPSLKSRLTISKDSSSNQVFLMITGVGTADAATYYCARY<br>YYFDYGYAIDYWGQGTSVTVSS<br>(SEQ ID NO: 112) |

TABLE 2-continued

Anti-PD-1 Mouse Leads-VH Sequences

701C1VH  EVQLQQSGPELVKPGASVKMSCKASGYTFTSYVIHWVKQKPGQGLEWIGY
IDPSNDDTKYNEKFKGKATLTSDKSSSTAYMELSSLTSEDSAVYYCAREA
YYGGLYGMDYWGQGTSVTVSS
(SEQ ID NO: 113)

701E9VH  QVQLQQSGPELVKPGASVKLSCKASGYTFIDYTIHWVKQSPGQGLEWIGW
IFPGSTNDTKYNDKFKGKATMTADKSSTAYMQLSSLTSEDSAVYFCARY
RTDFDYWGQGTTLTVSS
(SEQ ID NO: 114)

703D10VH  QVQLQQPGAELVKPGASVKLSCKASGYSFTSYWMHWVRQRPGQGLEWIGD
IDPSNSYAYHSQKFKGKATLTVDKSSSTAYMQLSSLTSEDSAVYFCARAD
GTSHWYFDVWGAGTAVTVSS
(SEQ ID NO: 115)

708E4VH  QIQLQQSGPELVKPGASVKISCKASGYTFTDYYLNWVKQRPGHGLEWIGW
IYPGSSDTKHNENFKGKATLTVDTYSSTAYMQLGSLTSEDSAVYFCTRYS
NFFFDYWGQGTTLTVSS
(SEQ ID NO: 116)

709A6VH  QVTLKESGPGILQPSQTLSLTCSFSGFSLSTSGMGVSWIRQPSGKGLEWL
THIYWDDDKRYNPSLKSRLTISKDTSRNQVFLEITSVDTADTATYFCARS
SQGLYSSYDYWGQGTTLTVSS
(SEQ ID NO: 117)

718C2VH  EVQLQQSGPELVKPGASVKMSCKASGYTFTSYVMHWVRQKPGQGLEWIGY
IDPDNDGTKYNEKFKGKATLTSDKSSSTAYMELSSLTSEDSAVYYCAREA
YYGGLYGMDYWGQGSSVTVSS
(SEQ ID NO: 118)

723C2VH  EVQLVESGGGLVQPGGSLKLSCAASGFTFSDYYMSWVRQTPEKRLEWVAY
ISSGGGSSYYPDSVKGRFTISRDNTKNTLYLQMSSLKSEDTAVYYCARLP
HYFAMDCWGQGTSVTVSS
(SEQ ID NO: 119)

803E6VH  EVKLVESEGGLVQPGSSMKLSCTASGFTFSDYYMAWVRQVPEKGLEWVAN
INYDGFNTYYLDSLKSRFIISRDNAKNILYLQMSSLKSEDTATYYCARGG
YWSLYFDYWGQGTTLTVSS
(SEQ ID NO: 120)

811G3VH  QIQLQQSGPEVVKPGASVKISCKASGYTFTDYYINWVKQRPGQGLEWIGW
IYPGGGHTKYNEKFKGEATLTVDTSSRTAYMQLSSLTSEDSAVYFCARYS
NYYFDFWGHGTTLTVSS
(SEQ ID NO: 121)

814E10VH  QIQLQQSGPELVKPGASVKISCKASGYTFTSYYIQWVKQRPGQGLEWIGW
IYPGDGTTNYNENFKGKTTLTADKSSSTVYMLLSSLTSEDSAVYFCARYG
LVPFDYWGQGTTLTVSS
(SEQ ID NO: 122)

820C3VH  QIQLQQSGPELVKTGASVKISCKASGNTFNSNYIQWVKQRPGQGLEWIGW
IYPGDGSTNYSEKFKGKTTLTADKSSSTAYMLVSSLTSEDSAVYFCARYG
PVPFDYWGQGTTLSVSS
(SEQ ID NO: 123)

The mouse light chain and heavy chain CDRs of the various mouse antibodies are shown in Table 3 and Table 4, respectively. Tables 3 and 4 also show three light chain CDRs and three heavy chains CDRs derived from the mouse antibody 723C2 through the humanization process.

TABLE 3

LIGHT CHAIN CDR sequences

| | L-CDR1 | L-CDR2 | L-CDR3 |
|---|---|---|---|
| 306E6 | RSSKSLLHRNGITYLY (SEQ ID NO: 1) | EMSNLAS (SEQ ID NO: 2) | GQNLEFPLT (SEQ ID NO: 3) |
| 307A3 | RSSKSLLHRNGITYLY (SEQ ID NO: 1) | EMSNLAS (SEQ ID NO: 2) | GQNLEFPLT (SEQ ID NO: 3) |
| 313C12 | KASQNVGTAVA (SEQ ID NO: 4) | SVSNRYT (SEQ ID NO: 5) | QQYSSYPFT (SEQ ID NO: 6) |

TABLE 3-continued

LIGHT CHAIN CDR sequences

| | L-CDR1 | L-CDR2 | L-CDR3 |
|---|---|---|---|
| 414A12 | HASQGINNNIG (SEQ ID NO: 7) | HKSNLED (SEQ ID NO: 8) | VQYAQFPYT (SEQ ID NO: 9) |
| 502H1 | RSSKSLLHRNGITYLY (SEQ ID NO: 10) | QMSNLAS (SEQ ID NO: 11) | AQNLELPLT (SEQ ID NO: 12) |
| 701C1 | KSSQSLLYSSNQKNYLA (SEQ ID NO: 13) | WASTRES (SEQ ID NO: 14) | HQYYSSPLT (SEQ ID NO: 15) |
| 701E9 | RASQEISGYLS (SEQ ID NO: 16) | AASTLDS (SEQ ID NO: 17) | LQYASYPLT (SEQ ID NO: 18) |
| 703D10 | SANSSVSFMH (SEQ ID NO: 19) | STSSLAS (SEQ ID NO: 20) | QQRSSYPLT (SEQ ID NO: 21) |
| 708E4 | KASQNVVTYVA (SEQ ID NO: 22) | SASYRYS (SEQ ID NO: 23) | QQYHSYPYT (SEQ ID NO: 24) |
| 709A6 | RASESVDIYGISFLH (SEQ ID NO: 25) | RASNLDS (SEQ ID NO: 26) | QQSNKDPLT (SEQ ID NO: 27) |
| 718C2 | KSSQSLLYSSNQKIYLA (SEQ ID NO: 28) | WASTRES (SEQ ID NO: 14) | QQYYNSPLT (SEQ ID NO: 29) |
| 723C2 | SASSSISSDYLH (SEQ ID NO: 30) | RTSNLAS (SEQ ID NO: 31) | QQGTSLPRA (SEQ ID NO: 32) |
| Hu_723C2-463-60 | SASQSISSDYLH (SEQ ID NO: 164) | RTSN LAS (SEQ ID NO: 31) | QQGTSLPRA (SEQ ID NO: 32) |
| Hu_723C2-462-07 | QASQSISSDYLH (SEQ ID NO: 165) | RTSN LET (SEQ ID NO: 166) | QQGTSLPRA (SEQ ID NO: 32) |
| Hu_723C2-462-08 | QASQSISSDYLH (SEQ ID NO: 165) | RTSN LES (SEQ ID NO: 167) | QQGTSLPRA (SEQ ID NO: 32) |
| 803E6 | KSSQSLLHSGNQKNYMT (SEQ ID NO: 33) | WASTRES (SEQ ID NO: 14) | QNDYSYPLT (SEQ ID NO: 34) |
| 811G3 | RASQEISGYLS (SEQ ID NO: 16) | VASTLDS (SEQ ID NO: 35) | LQYANYPYT (SEQ ID NO: 36) |
| 814E10 | SASQDIINYLN (SEQ ID NO: 37) | STSSLHS (SEQ ID NO: 38) | HQYSQLPYT (SEQ ID NO: 39) |
| 820C3 | SASQDIFNYLN (SEQ ID NO: 40) | YTSSLHS (SEQ ID NO: 41) | QQYSNLPYT (SEQ ID NO: 42) |

TABLE 4

HEAVY CHAIN CDR sequences

| | H-CDR1 | H-CDR2 | H-CDR3 |
|---|---|---|---|
| 306E6 | GYTFTDYYVN (SEQ ID NO: 43) | DIHPNSGDTTYNQKFKD (SEQ ID NO: 44) | RRYDYDGFAY (SEQ ID NO: 45) |
| 307A3 | GYTFTDYYVN (SEQ ID NO: 43) | DIHPNNGGITYNQKFKG (SEQ ID NO: 46) | RRYDYDGFAY (SEQ ID NO: 45) |
| 313C12 | GFTFSDYGMH (SEQ ID NO: 47) | YINSDSNTIYYADTVKG (SEQ ID NO: 48) | LVAPDY (SEQ ID NO: 49) |
| 414A12 | GHTFTSNWIH (SEQ ID NO: 50) | EIDPSDSYTYYNQKFKG (SEQ ID NO: 51) | PGRNSNFAY (SEQ ID NO: 52) |
| 502H1 | GFSLSTSGMGVT (SEQ ID NO: 53) | HIFWDGDKRYNPSLKS (SEQ ID NO: 54) | YYYFDYGYAIDY (SEQ ID NO: 55) |
| 701C1 | GYTFTSYVIH (SEQ ID NO: 56) | YIDPSNDDTKYNEKFKG (SEQ ID NO: 57) | EAYYGGLYGMDY (SEQ ID NO: 58) |

TABLE 4-continued

HEAVY CHAIN CDR sequences

| | H-CDR1 | H-CDR2 | H-CDR3 |
|---|---|---|---|
| 701E9 | GYTFIDYTIH (SEQ ID NO: 59) | WIFPGSTNDTKYNDKFKG (SEQ ID NO: 60) | YRTDFDY (SEQ ID NO: 61) |
| 703D10 | GYSFTSYWMH (SEQ ID NO: 62) | DIDPSNSYAYHSQKFKG (SEQ ID NO: 63) | ADGTSHWYFDV (SEQ ID NO: 64) |
| 708E4 | GYTFTDYYLN (SEQ ID NO: 65) | WIYPGSSDTKHNENFKG (SEQ ID NO: 66) | YSNFFFDY (SEQ ID NO: 67) |
| 709A6 | GFSLSTSGMGVS (SEQ ID NO: 68) | HIYWDDDKRYNPSLKS (SEQ ID NO: 69) | SSQGLYSSYDY (SEQ ID NO: 70) |
| 718C2 | GYTFTSYVMH (SEQ ID NO: 71) | YIDPDNDGTKYNEKFKG (SEQ ID NO: 72) | EAYYGGLYGMDY (SEQ ID NO: 58) |
| 723C2 | GFTFSDYYMS (SEQ ID NO: 73) | YISSGGGSSYYPDSVKG (SEQ ID NO: 74) | LPHYFAMDC (SEQ ID NO: 75) |
| Hu_723C2-463-60 | GFTFSDYYMS (SEQ ID NO: 73) | YISSGGGSKYYPDLVKG (SEQ ID NO: 76) | LPHYFAMDY (SEQ ID NO: 77) |
| Hu_723C2-461-47 | GFTFSDYYMS (SEQ ID NO: 73) | YISSGGGSSYYPDAVKG (SEQ ID NO: 78) | LPHYFAMDY (SEQ ID NO: 77) |
| Hu_723C2-461-40 | GFTFSDYYMS (SEQ ID NO: 73) | YISSGGGSSYYPDLVKG (SEQ ID NO: 79) | LPHYFAMDY (SEQ ID NO: 77) |
| 803E6 | GFTFSDYYMA (SEQ ID NO: 80) | NINYDGFNTYYLDSLKS (SEQ ID NO: 81) | GGYWSLYFDY (SEQ ID NO: 82) |
| 811G3 | GYTFTDYYIN (SEQ ID NO: 83) | WIYPGGGHTKYNEKFKG (SEQ ID NO: 84) | YSNYYFDF (SEQ ID NO: 85) |
| 814E10 | GYTFTSYYIQ (SEQ ID NO: 86) | WIYPGDGTTNYNENFKG (SEQ ID NO: 87) | YGLVPFDY (SEQ ID NO: 88) |
| 820C3 | GNTFNSNYIQ (SEQ ID NO: 89) | WIYPGDGSTNYSEKFKG (SEQ ID NO: 90) | YGPVPFDY (SEQ ID NO: 91) |

The CDRs listed above in Tables 3 and 4 are defined using the Chemical Computing Group (CCG) numbering are underlined (Almagro et al., Proteins 2011; 79:3050-3066 and Maier et al, Proteins 2014; 82:1599-1610).

A representative number of humanized light chain and heavy chain variable regions derived from mouse antibody 723C2 are provided and shown in Tables 5 and 6.

TABLE 5

Humanized 723C2-VK Sequences

| | |
|---|---|
| 723C2VK-463-60 | GATATCCAGATGACGCAGAGCCCAAGCAGCCTGAGCGCGTCCGTGGG CGACCGCGTGACGATCACCTGTAGCGCGTCCCAGAGCATCAGCAGCG ACTATCTGCATTGGTATCAGCAGAAACCAGGTAAAGCCCCTAAACTG CTGATCTACCGGACCTCCAATCTGGCAAGCGGCGTGCCTAGCCGTTT CAGCGGTAGCGGCTCCGGTACCGACTTCACCTTTACTATCTCCAGCC TGCAGCCTGAAGACATCGCGACGTATTATTGTCAGCAGGGTACTAGC CTGCCTCGCGCCTTCGGCCAGGGGACCAAACTGGAAATCAAA (SEQ ID NO: 124) |
| | DIQMTQSPSSLSASVGDRVTITCSASQSISSDYLHWYQQKPGKAPKL LIYRTSNLASGVPSRFSGSGSGTDFTFTISSLQPEDIATYYCQQGTS LPRAFGQGTKLEIK (SEQ ID NO: 125) |
| 723C2VK-462-07 | GATATCCAGATGACGCAGAGCCCAAGCAGCCTGAGCGCGTCCGTGGG CGACCGCGTGACGATCACCTGTCAGGCGTCCCAGAGCATCAGCAGCG ACTATCTGCATTGGTATCAGCAGAAACCAGGTAAAGCCCCTAAACTG CTGATCTACCGGACCTCCAATCTGGAAACCGGCGTGCCTAGCCGTTT CAGCGGTAGCGGCTCCGGTACCGACTTCACCTTTACTATCTCCAGCC |

TABLE 5-continued

Humanized 723C2-VK Sequences

|  |  |
|---|---|
|  | TGCAGCCTGAAGACATCGCGACGTATTATTGTCAGCAGGGTACTAGC<br>CTGCCTCGCGCCTTCGGCCAGGGGACCAAACTGGAAATCAAA<br>(SEQ ID NO: 126)<br><br>DIQMTQSPSSLSASVGDRVTITCQASQSISSDYLHWYQQKPGKAPKL<br>LIYRTSNLETGVPSRFSGSGSGTDFTFTISSLQPEDIATYYCQQGTS<br>LPRAFGQGTKLEIK<br>(SEQ ID NO: 127) |
| 723C2VK-<br>462-08 | GATATCCAGATGACGCAGAGCCCAAGCAGCCTGAGCGCGTCCGTGGG<br>CGACCGCGTGACGATCACCTGTCAGGCGTCCCAGAGCATCAGCAGCG<br>ACTATCTGCATTGGTATCAGCAGAAACCAGGTAAAGCCCCTAAACTG<br>CTGATCTACCGGACCTCCAATCTGGAAAGCGGCGTGCCTAGCCGTTT<br>CAGCGGTAGCGGCTCCGGTACCGACTTCACCTTTACTATCTCCAGCC<br>TGCAGCCTGAAGACATCGCGACGTATTATTGTCAGCAGGGTACTAGC<br>CTGCCTCGCGCCTTCGGCCAGGGGACCAAACTGGAAATCAAA<br>(SEQ ID NO: 128)<br><br>DIQMTQSPSSLSASVGDRVTITCQASQSISSDYLHWYQQKPGKAPKL<br>LIYRTSNLESGVPSRFSGSGSGTDFTFTISSLQPEDIATYYCQQGTS<br>LPRAFGQGTKLEIK<br>(SEQ ID NO: 129) |

TABLE 6

Humanized 723C2-VH Sequence

| 723C2VH-<br>463-60 | GAAGTGCAGCTGGTGGAAAGCGGTGGTGGCCTGGTGCAGCCAGGCGG<br>CTCCCTGCGCCTGAGCTGCGCCGCAAGCGGTTTCACCTTTAGCGACT<br>ACTATATGTCCTGGGTGCGTCAGGCGCCAGGTAAAGGTCTGGAATGG<br>GTGTCATACATCAGCTCCGGGGGCGGTAGCAAGTACTATCCGGACCT<br>GGTGAAAGGCGCTTTACTATCTCCCGGGATAATGCAAAAAATAGCC<br>TGTACCTGCAGATGAGCAGCCTGCGGGCGGAAGATACCGCCGTGTAT<br>TACTGTGCGCGTCTGCCGCATTATTTCGCCATGGATTACTGGGGCCA<br>GGGGACCCTGGTGACCGTGAGCAGC<br>(SEQ ID NO: 130)<br><br>EVQLVESGGGLVQPGGSLRLSCAASGFTFSDYYMSWVRQAPGKGLEW<br>VSYISSGGGSKYYPDLVKGRFTISRDNAKNSLYLQMSSLRAEDTAVY<br>YCARLPHYFAMDYWGQGTLVTVSS<br>(SEQ ID NO: 131) |
| 723C2VH-<br>461-41 | GAAGTGCAGCTGGTGGAAAGCGGTGGTGGCCTGGTGCAGCCAGGCGG<br>CTCCCTGCGCCTGAGCTGCGCCGCAAGCGGTTTCACCTTTAGCGACT<br>ACTATATGTCCTGGGTGCGTCAGGCGCCAGGTAAAGGTCTGGAATGG<br>GTGGCATACATCAGCTCCGGGGGCGGTAGCAGCTACTATCCGGACCT<br>GGTGAAAGGCGCTTTACTATCTCCCGGGATAATGCAAAAAATAGCC<br>TGTACCTGCAGATGCAGAGCCTGCGGGCGGAAGATACCGCCGTGTAT<br>TACTGTGCGCGTCTGCCGCATTATTTCGCCATGGATTACTGGGGCCA<br>GGGGACCCTGGTGACCGTGAGCAGC<br>(SEQ ID NO: 132)<br><br>EVQLVESGGGLVQPGGSLRLSCAASGFTFSDYYMSWVRQAPGKGLEW<br>VAYISSGGGSSYYPDLVKGRFTISRDNAKNSLYLQMQSLRAEDTAVY<br>YCARLPHYFAMDYWGQGTLVTVSS<br>(SEQ ID NO: 133) |
| 723C2VH-<br>461-47 | GAAGTGCAGCTGGTGGAAAGCGGTGGTGGCCTGGTGCAGCCAGGCGG<br>CTCCCTGCGCCTGAGCTGCGCCGCAAGCGGTTTCACCTTTAGCGACT<br>ACTATATGTCCTGGGTGCGTCAGGCGCCAGGTAAAGGTCTGGAATGG<br>GTGGCATACATCAGCTCCGGGGGCGGTAGCAGCTACTATCCGGACGC<br>TGTGAAAGGCGCTTTACTATCTCCCGGGATAATGCAAAACAGAGCC<br>TGTACCTGCAGATGCAGAGCCTGCGGGCGGAAGATACCGCCGTGTAT<br>TACTGTGCGCGTCTGCCGCATTATTTCGCCATGGATTACTGGGGCCA<br>GGGGACCCTGGTGACCGTGAGCAGC<br>(SEQ ID NO: 134)<br><br>EVQLVESGGGLVQPGGSLRLSCAASGFTFSDYYMSWVRQAPGKGLEW<br>VAYISSGGGSSYYPDAVKGRFTISRDNAKQSLYLQMQSLRAEDTAVY<br>YCARLPHYFAMDYWGQGTLVTVSS<br>(SEQ ID NO: 135) |
| 723C2VH-<br>461-44 | GAAGTGCAGCTGGTGGAAAGCGGTGGTGGCCTGGTGCAGCCAGGCGG<br>CTCCCTGCGCCTGAGCTGCGCCGCAAGCGGTTTCACCTTTAGCGACT<br>ACTATATGTCCTGGGTGCGTCAGGCGCCAGGTAAAGGTCTGGAATGG |

TABLE 6-continued

| | Humanized 723C2-VH Sequence |
|---|---|
| | GTGGCCTACATCAGCTCCGGGGGCGGTAGCAGCTACTATCCGGACCT<br>GGTGAAAGGGCGCTTTACTATCTCCCGGGATAATGCAAAACAGAGCC<br>TGTACCTGCAGATGAACAGCCTGCGGGCGGAAGATACCGCCGTGTAT<br>TACTGTGCGCGTCTGCCGCATTATTTCGCCATGGATTACTGGGGCCA<br>GGGGACCCTGGTGACCGTGAGCAGC<br>(SEQ ID NO: 136)<br><br>EVQLVESGGGLVQPGGSLRLSCAASGFTFSDYYMSWVRQAPGKGLEW<br>VAYISSGGGSSYYPDLVKGRFTISRDNAKQSLYLQMNSLRAEDTAVY<br>YCARLPHYFAMDYWGQGTLVTVSS<br>(SEQ ID NO: 137) |
| 723C2VH-<br>461-40 | GAAGTGCAGCTGGTGGAAAGCGGTGGTGGCCTGGTGCAGCCAGGCGG<br>CTCCCTGCGCCTGAGCTGCGCCGCAAGCGGTTTCACCTTTAGCGACT<br>ACTATATGTCCTGGGTGCGTCAGGCGCCAGGTAAAGGTCTGGAATGG<br>GTGGCCTACATCAGCTCCGGGGGCGGTAGCAGCTACTATCCGGACCT<br>GGTGAAAGGGCGCTTTACTATCTCCCGGGATAATGCAAAACAGAGCC<br>TGTACCTGCAGATGCAGAGCCTGCGGGCGGAAGATACCGCCGTGTAT<br>TACTGTGCGCGTCTGCCGCATTATTTCGCCATGGATTACTGGGGCCA<br>GGGGACCCTGGTGACCGTGAGCAGC<br>(SEQ ID NO: 138)<br><br>EVQLVESGGGLVQPGGSLRLSCAASGFTFSDYYMSWVRQAPGKGLEW<br>VAYISSGGGSSYYPDLVKGRFTISRDNAKQSLYLQMQSLRAEDTAVY<br>YCARLPHYFAMDYWGQGTLVTVSS<br>(SEQ ID NO: 139) |

Selected combination of humanized light chain and heavy chain variable regions derived from mouse antibody 723C2 resulted in Antibodies A, B, C, D and E: Antibody A: 723C2-IgG4Pro-463-60 with IgK-463-60 (heavy chain variable region 723C2VH-463-60 and light chain variable region 723C2VK-463-60); Antibody B: 723C2-IgG4Pro-461-41 with IgK-462-07 (heavy chain variable region 723C2VH-461-41 and light chain variable region 723C2VK-462-07); Antibody C: 723C2-IgG4Pro-461-47 with IgK-462-07 (heavy chain variable region 723C2VH-461-47 and light chain variable region 723C2VK-462-07); Antibody D: 723C2-IgG4Pro-461-44 with IgK-462-08 (heavy chain variable region 723C2VH-461-44 and light chain variable region 723C2VK-462-08). Antibody E: 723C2-IgG4Pro-461-40 with IgK-462-08 (heavy chain variable region 723C2VH-461-40 and light chain variable region 723C2VK-462-08).

Antibodies A, B, C, D and E have the heavy and light chain sequences shown in Table 7.

TABLE 7

| | | Heavy and Light Chain DNA and Amino Acid Sequences for Antibodies A, B, C, D, and E |
|---|---|---|
| Antibody A | IgK<br>light<br>Chain<br>#463-60 | GATATCCAGATGACGCAGAGCCCAAGCAGCCTGAGCG<br>CGTCCGTGGGCGACCGCGTGACGATCACCTGTAGCGC<br>GTCCCAGAGCATCAGCAGCGACTATCTGCATTGGTAT<br>CAGCAGAAACCAGGTAAAGCCCCTAAACTGCTGATCT<br>ACCGGACCTCCAATCTGGCAAGCGGCGTGCCTAGCCG<br>TTTCAGCGGTAGCGGCTCCGGTACCGACTTCACCTTT<br>ACTATCTCCAGCCTGCAGCCTGAAGACATCGCGACGT<br>ATTATTGTCAGCAGGGTACTAGCCTGCCTCGCGCCTT<br>CGGCCAGGGGACCAAACTGGAAATCAAACGTACTGTG<br>GCTGCACCATCTGTCTTCATCTTCCCGCCATCTGATG<br>AGCAATTGAAATCTGGAACTGCCTCTGTTGTGTGCCT<br>GCTGAATAACTTCTATCCCAGAGAGGCCAAAGTACAG<br>TGGAAGGTGGATAACGCCCTCCAATCGGGTAACTCCC<br>AGGAGAGTGTCACAGAGCAGGACAGCAAGGACAGCAC<br>CTACAGCCTCAGCAGCACCCTGACGCTGAGCAAAGCA<br>GACTACGAGAAACACAAAGTCTACGCCTGCGAAGTCA<br>CCCATCAGGGCCTGAGCTCGCCCGTCACAAAGAGCTT<br>CAACAGGGGAGAGTGT (SEQ ID NO: 140)<br><br><u>DIQMTQSPSSLSASVGDRVTITCSASQSISSDYLHWY</u><br><u>QQKPGKAPKLLIYRTSNLASGVPSRFSGSGSGTDFTF</u><br><u>TISSLQPEDIATYYCQQGTSLPRAFGQGTKLEIKRTV</u><br>AAPSVFIFPPSDEQLKSGTASVVCLLNNFYPREAKVQ<br>WKVDNALQSGNSQESVTEQDSKDSTYSLSSTLTLSKA<br>DYEKHKVYACEVTHQGLSSPVTKSFNRGEC<br>(SEQ ID NO: 141) |
| | IgG4Pro<br>Heavy<br>Chain<br>#463-60 | GAAGTGCAGCTGGTGGAAAGCGGTGGTGGCCTGGTGC<br>AGCCAGGCGGCTCCCTGCGCCTGAGCTGCGCCGCAAG<br>CGGTTTCACCTTTAGCGACTACTATATGTCCTGGGTG<br>CGTCAGGCGCCAGGTAAAGGTCTGGAATGGGTGTCAT |

TABLE 7 -continued

Heavy and Light Chain DNA and Amino Acid Sequences for Antibodies A, B, C, D, and E

| | | |
|---|---|---|
| | | ACATCAGCTCCGGGGGCGGTAGCAAGTACTATCCGGA<br>CCTGGTGAAAGGGCGCTTTACTATCTCCCGGGATAAT<br>GCAAAAAATAGCCTGTACCTGCAGATGAGCAGCCTGC<br>GGGCGGAAGATACCGCCGTGTATTACTGTGCGCGTCT<br>GCCGCATTATTTCGCCATGGATTACTGGGGCCAGGGG<br>ACCCTGGTGACCGTGAGCAGCGCCTCCACAAAGGGCC<br>CTTCCGTGTTCCCCCTGGCCCCTTGCTCCCGGTCCAC<br>CTCCGAGTCTACCGCCGCTCTGGGCTGCCTGGTCAAG<br>GACTACTTCCCCGAGCCCGTGACCGTGTCCTGGAACT<br>CTGGCGCCCTGACCTCCGGCGTGCACACCTTCCCTGC<br>TGTGCTGCAGTCCTCCGGCCTGTACTCCCTGTCCTCC<br>GTCGTGACCGTGCCCTCCTCTAGCCTGGGCACCAAGA<br>CCTACACCTGTAACGTGGACCACAAGCCCTCCAACAC<br>CAAGGTGGACAAGCGGGTGGAATCTAAGTACGGCCCT<br>CCCTGCCCCCCCTGCCCTGCCCCTGAATTTCTGGGCG<br>GACCCTCCGTGTTCCTGTTCCCCCCAAAGCCCAAGGA<br>CACCCTGATGATCTCCCGGACCCCCGAAGTGACCTGC<br>GTGGTGGTGGACGTGTCCCAGGAAGATCCCGAGGTCC<br>AGTTTAATTGGTACGTGGACGGCGTGGAAGTGCACAA<br>CGCCAAGACCAAGCCCAGAGAGGAACAGTTCAACTCC<br>ACCTACCGGGTGGTGTCCGTGCTGACCGTGCTGCACC<br>AGGACTGGCTGAACGGCAAAGAGTACAAGTGCAAGGT<br>GTCCAACAAGGGCCTGCCCTCCAGCATCGAAAAGACC<br>ATCTCCAAGGCCAAGGGCCAGCCCCGCGAGCCCCAGG<br>TGTACACCCTGCCTCCAAGCCAGGAAGAGATGACCAA<br>GAACCAGGTGTCCCTGACCTGTCTGGTCAAGGGCTTC<br>TACCCCTCCGATATCGCCGTGGAATGGGAGTCCAACG<br>GCCAGCCCGAGAACAACTACAAGACCACCCCCCCTGT<br>GCTGGACTCCGACGGCTCCTTCTTCCTGTACTCTCGG<br>CTGACCGTGGACAAGTCCCGGTGGCAGGAAGGCAACG<br>TCTTCTCCTGCTCCGTGATGCACGAGGCCCTGCACAA<br>CCACTACACCCAGAAGTCCCTGTCCCTGAGCCTGGGC<br>(SEQ ID NO: 142)<br><br>_EVQLVESGGGLVQPGGSLRLSCAASGFTFSDYYMSWV_<br>_RQAPGKGLEWVSYISSGGGSKYYPDLVKGRFTISRDN_<br>_AKNSLYLQMSSLRAEDTAVYYCARLPHYFAMDYWGQG_<br>_TLVTVSSASTKGPSVFPLAPCSRSTSESTAALGCLVK_<br>DYFPEPVTVSWNSGALTSGVHTFPAVLQSSGLYSLSS<br>VVTVPSSSLGTKTYTCNVDHKPSNTKVDKRVESKYGP<br><br>PCP͟P͟CPAPEFLGGPSVFLFPPKPKDTLMISRTPEVTC<br><br>VVVDVSQEDPEVQFNWYVDGVEVHNAKTKPREEQFNS<br>TYRVVSVLTVLHQDWLNGKEYKCKVSNKGLPSSIEKT<br>ISKAKGQPREPQVYTLPPSQEEMTKNQVSLTCLVKGF<br>YPSDIAVEWESNGQPENNYKTTPPVLDSDGSFFLYSR<br>LTVDKSRWQEGNVFSCSVMHEALHNHYTQKSLSLSLG<br>(SEQ ID NO: 143) |
| Antibody B | IgK<br>light<br>Chain<br>#462-07 | GACATCCAGATGACCCAGAGCCCAAGCAGCCTGAGCG<br>CCAGCGTGGGCGACCGCGTGACCATCACCTGCCAGGC<br>CAGCCAGAGCATCAGCAGCGACTACCTGCACTGGTAC<br>CAGCAGAAGCCAGGCAAGGCCCCCAAAGCTGCTGATCT<br>ACCGCACCAGCAACCTGGAGACCGGCGTGCCAAGCCG<br>CTTCAGCGGCAGCGGCAGCGGCACCGACTTCACCTTC<br>ACCATCAGCAGCCTGCAGCCAGAGGACATCGCCACCT<br>ACTACTGCCAGCAGGGCACCAGCCTGCCACGCGCCTT<br>CGGCCAGGGCACCAAGCTGGAGATCAAGCGTACGTGTG<br>GCTGCACCATCTGTCTTCATCTTCCCGCCATCTGATG<br>AGCAATTGAAATCTGGAACTGCCTCTGTTGTGTGCCT<br>GCTGAATAACTTCTATCCCAGAGAGGCCAAAGTACAG<br>TGGAAGGTGGATAACGCCCTCCAATCGGGTAACTCCC<br>AGGAGAGTGTCACAGAGCAGGACAGCAAGGACAGCAC<br>CTACAGCCTCAGCAGCACCCTGACGCTGAGCAAAGCA<br>GACTACGAGAAACACAAAGTCTACGCCTGCGAAGTCA<br>CCCATCAGGGCCTGAGCTCGCCCGTCACAAAGAGCTT<br>CAACAGGGGAGAGTGT (SEQ ID NO: 144)<br><br>_DIQMTQSPSSLSASVGDRVTITCQASQSISSDYLHWY_<br>_QQKPGKAPKLLIYRTSNLETGVPSRFSGSGSGTDFTF_<br>_TISSLQPEDIATYYCQQGTSLPRAFGQGTKLEIK_RTV<br>AAPSVFIFPPSDEQLKSGTASVVCLLNNFYPREAKVQ<br>WKVDNALQSGNSQESVTEQDSKDSTYSLSSTLTLSKA<br>DYEKHKVYACEVTHQGLSSPVTKSFNRGEC<br>(SEQ ID NO: 145) |

TABLE 7 -continued

Heavy and Light Chain DNA and Amino Acid Sequences for Antibodies A, B, C, D, and E

| | | |
|---|---|---|
| | IgG4Pro Heavy Chain #461-41 | GAAGTGCAGCTGGTGGAAAGCGGCGGAGGCCTGGTGC<br>AGCCAGGCGGCAGCCTGAGACTGAGCTGCGCCGCCAG<br>CGGCTTCACCTTCAGCGACTACTACATGAGCTGGGTG<br>CGCCAGGCCCCAGGCAAGGGCCTGGAGTGGGTGGCCT<br>ACATCAGCAGCGGCGGCGGCAGCAGCTACTACCCAGA<br>CCTGGTGAAGGGCCGCTTCACCATCAGCCGCGACAAC<br>GCCAAGAACAGCCTGTACCTGCAGATGCAGAGCCTGC<br>GCGCCGAGGACACCGCCGTGTACTACTGCGCCCGCCT<br>GCCACACTACTTCGCCATGGACTACTGGGGCCAGGGC<br>ACCCTGGTGACCGTGAGCAGCGCCTCCACAAAGGGCC<br>CTTCCGTGTTCCCCCTGGCCCCTTGCTCCCGGTCCAC<br>CTCCGAGTCTACCGCCGCTCTGGGCTGCCTGGTCAAG<br>GACTACTTCCCCGAGCCCGTGACCGTGTCCTGGAACT<br>CTGGCGCCCTGACCTCCGGCGTGCACACCTTCCCTGC<br>TGTGCTGCAGTCCTCCGGCCTGTACTCCCTGTCCTCC<br>GTCGTGACCGTGCCCTCCTCTAGCCTGGGCACCAAGA<br>CCTACACCTGTAACGTGGACCACAAGCCCTCCAACAC<br>CAAGGTGGACAAGCGGGTGGAATCTAAGTACGGCCCT<br>CCCTGCCCCCCCTGCCCTGCCCCTGAATTTCTGGGCG<br>GACCCTCCGTGTTCCTGTTCCCCCCAAAGCCCAAGGA<br>CACCCTGATGATCTCCCGGACCCCCGAAGTGACCTGC<br>GTGGTGGTGGACGTGTCCCAGGAAGATCCCGAGGTCC<br>AGTTTAATTGGTACGTGGACGGCGTGGAAGTGCACAA<br>CGCCAAGACCAAGCCCAGAGAGGAACAGTTCAACTCC<br>ACCTACCGGGTGGTGTCCGTGCTGACCGTGCTGCACC<br>AGGACTGGCTGAACGGCAAAGAGTACAAGTGCAAGGT<br>GTCCAACAAGGGCCTGCCCTCCAGCATCGAAAAGACC<br>ATCTCCAAGGCCAAGGGCCAGCCCCGCGAGCCCCAGG<br>TGTACACCCTGCCTCCAAGCCAGGAAGAGATGACCAA<br>GAACCAGGTGTCCCTGACCTGTCTGGTCAAGGGCTTC<br>TACCCCTCCGATATCGCCGTGGAATGGGAGTCCAACG<br>GCCAGCCCGAGAACAACTACAAGACCACCCCCCCTGT<br>GCTGGACTCCGACGGCTCCTTCTTCCTGTACTCTCGG<br>CTGACCGTGGACAAGTCCCGGTGGCAGGAAGGCAACG<br>TCTTCTCCTGCTCCGTGATGCACGAGGCCCTGCACAA<br>CCACTACACCCAGAAGTCCCTGTCCCTGAGCCTGGGC<br>(SEQ ID NO: 146)<br><br>EVQLVESGGGLVQPGGSLRLSCAASGFTFSDYYMSWV<br>RQAPGKGLEWVAYISSGGGSSYYPDLVKGRFTISRDN<br>AKNSLYLQMQSLRAEDTAVYYCARLPHYFAMDYWGQG<br>TLVTVSSASTKGPSVFPLAPCSRSTSESTAALGCLVK<br>DYFPEPVTVSWNSGALTSGVHTFPAVLQSSGLYSLSS<br>VVTVPSSSLGTKTYTCNVDHKPSNTKVDKRVESKYGP<br><br>PCPECPAPEFLGGPSVFLFPPKPKDTLMISTPEVTC<br><br>VVVDVSQEDPEVQFNWYVDGVEVHNAKTKPREEQFNS<br>TYRVVSVLTVLHQDWLNGKEYKCKVSNKGLPSSIEKT<br>ISKAKGQPREPQVYTLPPSQEEMTKNQVSLTCLVKGF<br>YPSDIAVEWESNGQPENNYKTTPPVLDSDGSFFLYSR<br>LTVDKSRWQEGNVFSCSVMHEALHNHYTQKSLSLSLG<br>(SEQ ID NO: 147) |
| Antibody C | IgK light Chain #462-07 | GACATCCAGATGACCCAGAGCCCAAGCAGCCTGAGCG<br>CCAGCGTGGGCGACCGCGTGACCATCACCTGCCAGGC<br>CAGCCAGAGCATCAGCAGCGACTACCTGCACTGGTAC<br>CAGCAGAAGCCAGGCAAGGCCCCAAAGCTGCTGATCT<br>ACCGCACCAGCAACCTGGAGACCGGCGTGCCAAGCCG<br>CTTCAGCGGCAGCGGCAGCGGCACCGACTTCACCTTC<br>ACCATCAGCAGCCTGCAGCCAGAGGACATCGCCACCT<br>ACTACTGCCAGCAGGGCACCAGCCTGCCACGCGCCTT<br>CGGCCAGGGCACCAAGCTGGAGATCAAGCGTACTGTG<br>GCTGCACCATCTGTCTTCATCTTCCCGCCATCTGATG<br>AGCAATTGAAATCTGGAACTGCCTCTGTTGTGTGCCT<br>GCTGAATAACTTCTATCCCAGAGAGGCCAAAGTACAG<br>TGGAAGGTGGATAACGCCCTCCAATCGGGTAACTCCC<br>AGGAGAGTGTCACAGAGCAGGACAGCAAGGACAGCAC<br>CTACAGCCTCAGCAGCACCCTGACGCTGAGCAAAGCA<br>GACTACGAGAAACACAAAGTCTACGCCTGCGAAGTCA<br>CCCATCAGGGCCTGAGCTCGCCCGTCACAAAGAGCTT<br>CAACAGGGGAGAGTGT (SEQ ID NO: 144)<br><br>DIQMTQSPSSLSASVGDRVTITCQASQSISSDYLHWY<br>QQKPGKAPKLLIYRTSNLETGVPSRFSGSGSGTDFTF |

TABLE 7 -continued

Heavy and Light Chain DNA and Amino Acid Sequences for Antibodies A, B, C, D, and E

|  |  |  |
|---|---|---|
|  |  | TISSLQPEDIATYYCQQGTSLPRAFGQGTKLEIKRTV<br>AAPSVFIFPPSDEQLKSGTASVVCLLNNFYPREAKVQ<br>WKVDNALQSGNSQESVTEQDSKDSTYSLSSTLTLSKA<br>DYEKHKVYACEVTHQGLSSPVTKSFNRGEC<br>(SEQ ID NO: 145) |
|  | IgG4Pro<br>Heavy<br>Chain<br>#461-47 | GAGGTGCAGCTGGTGGAGAGCGGCGGCGGCCTGGTGC<br>AGCCAGGTGGTAGCCTGCGCCTGAGCTGCGCCGCCAG<br>CGGCTTCACCTTCAGCGACTACTACATGAGCTGGGTG<br>CGCCAGGCTCCAGGCAAGGGTCTGGAATGGGTGGCCT<br>ACATCAGCAGCGGCGGCGGCAGCAGCTACTACCCAGA<br>CGCCGTGAAGGGCCGCTTCACCATCAGCCGCGACAAC<br>GCCAAGCAGAGCCTGTACCTGCAGATGCAGAGCCTGC<br>GCGCCGAGGACACCGCCGTGTACTACTGCGCCCGCCT<br>GCCACACTACTTCGCCATGGACTACTGGGGCCAGGGC<br>ACCCTGGTGACCGTGAGCAGCGCCTCCACAAGGGCC<br>CTTCCGTGTTCCCCCTGGCCCCTTGCTCCCGGTCCAC<br>CTCCGAGTCTACCGCCGCTCTGGGCTGCCTGGTCAAG<br>GACTACTTCCCCGAGCCCGTGACCGTGTCCTGGAACT<br>CTGGCGCCCTGACCTCCGGCGTGCACACCTTCCCTGC<br>TGTGCTGCAGTCCTCCGGCCTGTACTCCCTGTCCTCC<br>GTCGTGACCGTGCCCTCCTCTAGCCTGGGCACCAAGA<br>CCTACACCTGTAACGTGGACCACAAGCCCTCCAACAC<br>CAAGGTGGACAAGCGGGTGGAATCTAAGTACGGCCCT<br>CCCTGCCCCCCCTGCCCTGCCCTGAATTTCTGGGCG<br>GACCCTCCGTGTTCCTGTTCCCCCCAAAGCCCAAGGA<br>CACCCTGATGATCTCCCGGACCCCCGAAGTGACCTGC<br>GTGGTGGTGGACGTGTCCCAGGAAGATCCCGAGGTCC<br>AGTTTAATTGGTACGTGGACGGCGTGGAAGTGCACAA<br>CGCCAAGACCAAGCCCAGAGAGGAACAGTTCAACTCC<br>ACCTACCGGGTGGTGTCCGTGCTGACCGTGCTGCACC<br>AGGACTGGCTGAACGGCAAAGAGTACAAGTGCAAGGT<br>GTCCAACAAGGGCCTGCCCTCCAGCATCGAAAAGACC<br>ATCTCCAAGGCCAAGGGCCAGCCCCGCGAGCCCCAGG<br>TGTACACCCTGCCTCCAAGCCAGGAAGAGATGACCAA<br>GAACCAGGTGTCCCTGACCTGTCTGGTCAAGGGCTTC<br>TACCCCTCCGATATCGCCGTGGAATGGGAGTCCAACG<br>GCCAGCCCGAGAACAACTACAAGACCACCCCCCCTGT<br>GCTGGACTCCGACGGCTCCTTCTTCCTGTACTCTCGG<br>CTGACCGTGGACAAGTCCCGGTGGCAGGAAGGCAACG<br>TCTTCTCCTGCTCCGTGATGCACGAGGCCCTGCACAA<br>CCACTACACCCAGAAGTCCCTGTCCCTGAGCCTGGGC<br>(SEQ ID NO: 148) |
|  |  | EVQLVESGGGLVQPGGSLRLSCAASGFTFSDYYMSWV<br>RQAPGKGLEWVAYISSGGGSSYYPDAVKGRFTISRDN<br>AKQSLYLQMQSLRAEDTAVYYCARLPHYFAMDYWGQG<br>TLVTVSSASTKGPSVFPLAPCSRSTSESTAALGCLVK<br>DYFPEPVTVSWNSGALTSGVHTFPAVLQSSGLYSLSS<br>VVTVPSSSLGTKTYTCNVDHKPSNTKVDKRVESKYGP<br><br>PCPPCPAPEFLGGPSVFLFPPKPKDTLMISRTPEVTC<br><br>VVVDVSQEDPEVQFNWYVDGVEVHNAKTKPREEQFNS<br>TYRVVSVLTVLHQDWLNGKEYKCKVSNKGLPSSIEKT<br>ISKAKGQPREPQVYTLPPSQEEMTKNQVSLTCLVKGF<br>YPSDIAVEWESNGQPENNYKTTPPVLDSDGSFFLYSR<br>LTVDKSRWQEGNVFSCSVMHEALHNHYTQKSLSLSLG<br>(SEQ ID NO: 149) |
| Antibody D | IgK<br>light<br>Chain<br>#462-08 | GACATCCAGATGACCCAGAGCCCAAGCAGCCTGAGCG<br>CCAGCGTGGGCGACCGCGTGACCATCACCTGCCAGGC<br>CAGCCAGAGCATCAGCAGCGACTACCTGCACTGGTAC<br>CAGCAGAAGCCAGGCAAGGCCCCAAAGCTGCTGATCT<br>ACCGCACCAGCAACCTGGAGAGCGGCGTGCCAAGCCG<br>CTTCAGCGGCAGCGGCAGCGGCACCGACTTCACCTTC<br>ACCATCAGCAGCCTGCAGCCAGAGGACATCGCCACCT<br>ACTACTGCCAGCAGGGCACCAGCCTGCCACGCGCCTT<br>CGGCCAGGGCACCAAGCTGGAGATCAAGCGTACTGTG<br>GCTGCACCATCTGTCTTCATCTTCCCGCCATCTGATG<br>AGCAATTGAAATCTGGAACTGCCTCTGTTGTGTGCCT<br>GCTGAATAACTTCTATCCCAGAGAGGCCAAAGTACAG<br>TGGAAGGTGGATAACGCCCTCCAATCGGGTAACTCCC<br>AGGAGAGTGTCACAGAGCAGGACAGCAAGGACAGCAC<br>CTACAGCCTCAGCAGCACCCTGACGCTGAGCAAAGCA<br>GACTACGAGAAACACAAAGTCTACGCCTGCGAAGTCA |

TABLE 7 -continued

Heavy and Light Chain DNA and Amino Acid Sequences for Antibodies A, B, C, D, and E

|  |  |  |
|---|---|---|
|  |  | CCCATCAGGGCCTGAGCTCGCCCGTCACAAAGAGCTT CAACAGGGGAGAGTGT (SEQ ID NO: 150) |
|  |  | DIQMTQSPSSLSASVGDRVTITCQASQSISSDYLHWY QQKPGKAPKLLIYRTSNLESGVPSRFSGSGSGTDFTF TISSLQPEDIATYYCQQGTSLPRAFGQGTKLEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC (SEQ ID NO: 151) |
|  | IgG4Pro Heavy Chain #461-44 | GAAGTGCAGCTGGTGGAAAGCGGTGGTGGCCTGGTGC AGCCAGGCGGCTCCCTGCGCCTGAGCTGCGCCGCAAG CGGTTTCACCTTTAGCGACTACTATATGTCCTGGGTG CGTCAGGCGCCAGGTAAAGGTCTGGAATGGGTGGCCT ACATCAGCTCCGGGGGCGGTAGCAGCTACTATCCGGA CCTGGTGAAAGGGCGCTTTACTATCTCCCGGGATAAT GCAAAACAGAGCCTGTACCTGCAGATGAACAGCCTGC GGGCGGAAGATACCGCCGTGTATTACTGTGCGCGTCT GCCGCATTATTTCGCCATGGATTACTGGGGCCAGGGG ACCCTGGTGACCGTGAGCAGCGCCTCCACAAAGGGCC CTTCCGTGTTCCCCCTGGCCCCTTGCTCCCGGTCCAC CTCCGAGTCTACCGCCGCTCTGGGCTGCCTGGTCAAG GACTACTTCCCCGAGCCCGTGACCGTGTCCTGGAACT CTGGCGCCCTGACCTCCGGCGTGCACACCTTCCCTGC TGTGCTGCAGTCCTCCGGCCTGTACTCCCTGTCCTCC GTCGTGACCGTGCCCTCCTCTAGCCTGGGCACCAAGA CCTACACCTGTAACGTGGACCACAAGCCCTCCAACAC CAAGGTGGACAAGCGGGTGGAATCTAAGTACGGCCCT CCCTGCCCCCCCTGCCTGCCCCTGAATTTCTGGGCG GACCCTCCGTGTTCCTGTTCCCCCCAAAGCCCAAGGA CACCCTGATGATCTCCCGGACCCCCGAAGTGACCTGC GTGGTGGTGGACGTGTCCCAGGAAGATCCCGAGGTCC AGTTTAATTGGTACGTGGACGGCGTGGAAGTGCACAA CGCCAAGACCAAGCCCAGAGAGGAACAGTTCAACTCC ACCTACCGGGTGGTGTCCGTGCTGACCGTGCTGCACC AGGACTGGCTGAACGGCAAAGAGTACAAGTGCAAGGT GTCCAACAAGGGCCTGCCCTCCAGCATCGAAAAGACC ATCTCCAAGGCCAAGGGCCAGCCCCGCGAGCCCCAGG TGTACACCCTGCCTCCAAGCCAGGAAGAGATGACCAA GAACCAGGTGTCCCTGACCTGTCTGGTCAAGGGCTTC TACCCCTCCGATATCGCCGTGGAATGGGAGTCCAACG GCCAGCCCGAGAACAACTACAAGACCACCCCCCCTGT GCTGGACTCCGACGGCTCCTTCTTCCTGTACTCTCGG CTGACCGTGGACAAGTCCCGGTGGCAGGAAGGCAACG TCTTCTCCTGCTCCGTGATGCACGAGGCCCTGCACAA CCACTACACCCAGAAGTCCCTGTCCCTGAGCCTGGGC (SEQ ID NO: 152) |
|  |  | EVQLVESGGGLVQPGGSLRLSCAASGFTFSDYYMSWV RQAPGKGLEWVAYISSGGGSSYYPDLVKGRFTISRDN AKQSLYLQMNSLRAEDTAVYYCARLPHYFAMDYWGQG TLVTVSSASTKGPSVFPLAPCSRSTSESTAALGCLVK DYFPEPVTVSWNSGALTSGVHTFPAVLQSSGLYSLSS VVIVPSSSLGIKTYTCNVDHKPSNIKVDKRVESKYGP PCP☐CPAPEFLGGPSVFLFPPKPKDTLMISRTPEVTC VVVDVSQEDPEVQFNWYVDGVEVHNAKTKPREEQFNS TYRVVSVLTVLHQDWLNGKEYKCKVSNKGLPSSIEKT ISKAKGQPREPQVYTLPPSQEEMTKNQVSLTCLVKGF YPSDIAVEWESNGQPENNYKTTPPVLDSDGSFFLYSR LTVDKSRWQEGNVFSCSVMHEALHNHYTQKSLSLSLG (SEQ ID NO: 153) |
| Antibody E | IgK light Chain #462-08 | GACATCCAGATGACCCAGAGCCCAAGCAGCCTGAGCG CCAGCGTGGGCGACCGCGTGACCATCACCTGCCAGGC CAGCCAGAGCATCAGCAGCGACTACCTGCACTGGTAC CAGCAGAAGCCAGGCAAGGCCCCAAAGCTGCTGATCT ACCGCACCAGCAACCTGGAGAGCGGCGTGCCAAGCCG CTTCAGCGGCAGCGGCAGCGGCACCGACTTCACCTTC ACCATCAGCAGCCTGCAGCCAGAGGACATCGCCACCT ACTACTGCCAGCAGGGCACCAGCCTGCCACGCGCCTT CGGCCAGGGCACCAAGCTGGAGATCAAGCGTACTGTG GCTGCACCATCTGTCTTCATCTTCCCGCCATCTGATG AGCAATTGAAATCTGGAACTGCCTCTGTTGTGTGCCT |

TABLE 7 -continued

Heavy and Light Chain DNA and Amino Acid Sequences for Antibodies A, B, C, D, and E

|  |  |
|---|---|
|  | GCTGAATAACTTCTATCCCAGAGAGGCCAAAGTACAG<br>TGGAAGGTGGATAACGCCCTCCAATCGGGTAACTCCC<br>AGGAGAGTGTCACAGAGCAGGACAGCAAGGACAGCAC<br>CTACAGCCTCAGCAGCACCCTGACGCTGAGCAAAGCA<br>GACTACGAGAAACACAAAGTCTACGCCTGCGAAGTCA<br>CCCATCAGGGCCTGAGCTCGCCCGTCACAAAGAGCTT<br>CAACAGGGGAGAGTGT (SEQ ID NO:150)<br><br>DIQMTQSPSSLSASVGDRVTITCQASQSISSDYLHWY<br>QQKPGKAPKLLIYRTSNLESGVPSRFSGSGSGTDFTF<br>TISSLQPEDIATYYCQQGTSLPRAFGQGTKLEIKRTV<br>AAPSVFIFPPSDEQLKSGTASVVCLLNNFYPREAKVQ<br>WKVDNALQSGNSQESVTEQDSKDSTYSLSSTLTLSKA<br>DYEKHKVYACEVTHQGLSSPVTKSFNRGEC<br>(SEQ ID NO: 151) |
| IgG4Pro<br>Heavy<br>Chain<br>#461-40 | GAGGTGCAGCTGGTGGAGAGCGGCGGCGGCCTGGTGC<br>AGCCAGGTGGTAGCCTGCGCCTGAGCTGCGCCGCCAG<br>CGGCTTCACCTTCAGCGACTACTACATGAGCTGGGTG<br>CGCCAGGCTCCAGGCAAGGGTCTGGAATGGGTGGCCT<br>ACATCAGCAGCGGCGGCGGCAGCAGCTACTACCCAGA<br>CCTGGTGAAGGGCCGCTTCACCATCAGCCGCGACAAC<br>GCCAAGCAGAGCCTGTACCTGCAGATGCAGAGCCTGC<br>GCGCCGAGGACACCGCCGTGTACTACTGCGCCCGCCT<br>GCCACACTACTTCGCCATGGACTACTGGGGCCAGGGC<br>ACCCTGGTGACCGTGAGCAGCGCCTCCACAAAGGGCC<br>CTTCCGTGTTCCCCCTGGCCCCTTGCTCCCGGTCCAC<br>CTCCGAGTCTACCGCCGCTCTGGGCTGCCTGGTCAAG<br>GACTACTTCCCCGAGCCCGTGACCGTGTCCTGGAACT<br>CTGGCGCCCTGACCTCCGGCGTGCACACCTTCCCTGC<br>TGTGCTGCAGTCCTCCGGCCTGTACTCCCTGTCCTCC<br>GTCGTGACCGTGCCCTCCTCTAGCCTGGGCACCAAGA<br>CCTACACCTGTAACGTGGACCACAAGCCCTCCAACAC<br>CAAGGTGGACAAGCGGGTGGAATCTAAGTACGGCCCT<br>CCCTGCCCCCCCTGCCCTGCCCCTGAATTTCTGGGCG<br>GACCCTCCGTGTTCCTGTTCCCCCCAAAGCCCAAGGA<br>CACCCTGATGATCTCCCGGACCCCCGAAGTGACCTGC<br>GTGGTGGTGGACGTGTCCCAGGAAGATCCCGAGGTCC<br>AGTTTAATTGGTACGTGGACGGCGTGGAAGTGCACAA<br>CGCCAAGACCAAGCCCAGAGAGGAACAGTTCAACTCC<br>ACCTACCGGGTGGTGTCCGTGCTGACCGTGCTGCACC<br>AGGACTGGCTGAACGGCAAAGAGTACAAGTGCAAGGT<br>GTCCAACAAGGGCCTGCCCTCCAGCATCGAAAAGACC<br>ATCTCCAAGGCCAAGGGCCAGCCCCGCGAGCCCCAGG<br>TGTACACCCTGCCTCCAAGCCAGGAAGAGATGACCAA<br>GAACCAGGTGTCCCTGACCTGTCTGGTCAAGGGCTTC<br>TACCCCTCCGATATCGCCGTGGAATGGGAGTCCAACG<br>GCCAGCCCGAGAACAACTACAAGACCACCCCCCCTGT<br>GCTGGACTCCGACGGCTCCTTCTTCCTGTACTCTCGG<br>CTGACCGTGGACAAGTCCCGGTGGCAGGAAGGCAACG<br>TCTTCTCCTGCTCCGTGATGCACGAGGCCCTGCACAA<br>CCACTACACCCAGAAGTCCCTGTCCCTGAGCCTGGGC<br>(SEQ ID NO: 154)<br><br>EVQLVESGGGLVQPGGSLRLSCAASGFTFSDYYMSWV<br>RQAPGKGLEWVAYISSGGGSSYYPDLVKGRFTISRDN<br>AKQSLYLQMQSLRAEDTAVYYCARLPHYFAMDYWGQG<br>TLVTVSSASTKGPSVFPLAPCSRSTSESTAALGCLVK<br>DYFPEPVTVSWNSGALTSGVHTFPAVLQSSGLYSLSS<br>VVTVPSSSLGTKTYTCNVDHKPSNTKVDKRVESKYGP<br><br>PCPPCPAPEFLGGPSVFLFPPKPKDTLMISRTPEVTC<br><br>VVVDVSQEDPEVQFNWYVDGVEVHNAKTKPREEQFNS<br>TYRVVSVLTVLHQDWLNGKEYKCKVSNKGLPSSIEKT<br>ISKAKGQPREPQVYTLPPSQEEMTKNQVSLTCLVKGF<br>YPSDIAVEWESNGQPENNYKTTPPVLDSDGSFFLYSR<br>LTVDKSRWQEGNVFSCSVMHEALHNHYTQKSLSLSLG<br>(SEQ ID NO: 155) |

Light chains and heavy chain variable regions of Antibodies A, B, C, D, and E are underlined in Table 7. The hinge region in the heavy chain constant regions is shown in bold with the Ser228Pro mutation boxed.

Mouse lead 723C2 was also converted to human IgG1WT, IgG1KO, and IgG4Pro formats. IgG4Pro has one mutation in the hinge region, Ser228Pro, which prevents Fab-arm exchange. IgG1KO has two mutations in the hinge region, Leu234Ala and Leu235Ala, to reduce effector function (ADCC).

Chimeric 723C2 in human IgG1WT, IgG1 KO, and IgG4Pro formats are shown in Table 8.

TABLE 8

Heavy and Light Chain DNA and Amino Acid Sequences for chimeric 723C2 in human IgG1WT, IgG1KO and IgG4Pro

| | | |
|---|---|---|
| Chimeric 723C2 in IgG1WT (723-IgG1WT) | IgK light Chain | GAGATCGTGCTGACACAGAGCCCTACCACAATGGCCG CCTCTCCAGGCGAGAAGATCACCATCACATGTAGCGC CAGCAGCAGCATCAGCAGCGACTACCTGCACTGGTAT CAGCAGAAGCCTGGCTTCAGCCCCGAGCTGCTGATCT ACAGAACAAGCAATCTGGCCAGCGGCGTGCCAGCCAG ATTTTCTGGTTCTGGCAGCGGCACCAGCTACAGCCTG ACAATCGGATCCATGGAAGCCGAGGACGTGGCCACCT ATTACTGTCAGCAGGGCACAAGCCTGCCTAGAGCCTT TGGCGGAGGCACCAAGCTGGAAATCAAGCGTACTGTG GCTGCACCATCTGTCTTCATCTTCCCGCCATCTGATG AGCAATTGAAATCTGGAACTGCCTCTGTTGTGTGCCT GCTGAATAACTTCTATCCCAGAGAGGCCAAAGTACAG TGGAAGGTGGATAACGCCCTCCAATCGGGTAACTCCC AGGAGAGTGTCACAGAGCAGGACAGCAAGGACAGCAC CTACAGCCTCAGCAGCACCCTGACGCTGAGCAAAGCA GACTACGAGAAACACAAAGTCTACGCCTGCGAAGTCA CCCATCAGGGCCTGAGCTCGCCCGTCACAAAGAGCTT CAACAGGGGAGAGTGT (SEQ ID NO: 156) <br><br> EIVLTQSPTTMAASPGEKITITCSASSSISSDYLHWY QQKPGFSPELLIYRTSNLASGVPARFSGSGSGTSYSL TIGSMEAEDVATYYCQQGTSLPRAFGGGTKLEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC (SEQ ID NO: 157) |
| | IgG1WT heavy Chain | GAAGTGCAGCTGGTGGAATCTGGCGGAGGACTTGTTC AACCTGGCGGCAGCCTGAAACTGTCTTGTGCCGCCAG CGGCTTCACCTTCAGCGACTACTACATGAGCTGGGTC CGACAGACCCCTGAGAAGAGACTGGAATGGGTCGCCT ACATCAGCTCTGGCGGCGGAAGCAGCTACTACCCTGA TAGCGTGAAGGGCAGATTCACCATCAGCCGGGACAAC ACCAAGAACACCCTGTACCTGCAGATGTCCAGCCTGA AGTCTGAGGACACCGCCGTGTACTACTGTGCCAGACT GCCTCACTACTTCGCCATGGATTATTGGGGCCAGGGC ACCAGCGTGACCGTTTCTTCTGCCTCCACCAAGGGCC CATCGGTCTTCCCGCTAGCACCCTCCTCCAAGAGCAC CTCTGGGGGCACAGCGGCCCTGGGCTGCCTGGTCAAG GACTACTTCCCCGAACCGGTGACGGTGTCGTGGAACT CAGGCGCCCTGACCAGCGGCGTGCACACCTTCCCGGC TGTCCTACAGTCCTCAGGACTCTACTCCCTCAGCAGC GTGGTGACCGTGCCCTCCAGCAGCTTGGGCACCCAGA CCTACATCTGCAACGTGAATCACAAGCCCAGCAACAC CAAGGTGGACAAGCGCGTTGAGCCCAAATCTTGTGAC AAAACTCACACATGCCCACCGTGCCCAGCACCTGAAC TACTAGGGGACCGTCAGTCTTCCTCTTCCCCCCAAA ACCCAAGGACACCCTCATGATCTCCCGGACCCCTGAG GTCACATGCGTGGTGGTGGACGTGAGCCACGAAGACC CTGAGGTCAAGTTCAACTGGTACGTGGACGGCGTGGA GGTGCATAATGCCAAGACAAAGCCGCGGGAGGAGCAG TACAACAGCACGTACCGTGTGGTCAGCGTCCTCACCG TCCTGCACCAGGACTGGCTGAATGGCAAGGAGTACAA GTGCAAGGTCTCCAACAAAGCCCTCCCAGCCCCCATC GAGAAAACCATCTCCAAAGCCAAAGGGCAGCCCCGAG AACCACAGGTGTACACCCTGCCCCCATCCCGCGAGGA GATGACCAAGAACCAGGTAAGTTTGACCTGCCTGGTC AAAGGCTTCTATCCCAGCGACATCGCCGTGGAGTGGG AGAGCAATGGGCAGCCGGAGAACAACTACAAGACCAC GCCTCCCGTGCTGGACTCCGACGGCTCCTTCTTCCTC TATAGCAAGCTCACCGTGGACAAGAGCAGGTGGCAGC AGGGGAACGTCTTCTCATGCTCCGTGATGCATGAGGC TCTGCACAACCACTACACGCAGAAGAGCCTCTCCCTG TCTCCGGGT (SEQ ID NO: 158) |

TABLE 8-continued

Heavy and Light Chain DNA and Amino Acid Sequences
for chimeric 723C2 in human IgG1WT, IgG1KO and IgG4Pro

| | | |
|---|---|---|
| | | EVQLVESGGGLVQPGGSLKLSCAASGFTFSDYYMSWV
RQTPEKRLEWVAYISSGGGSSYYPDSVKGRFTISRDN
TKNTLYLQMSSLKSEDTAVYYCARLPHYFAMDYWGQG
TSVTVSSASTKGPSVFPLAPSSKSTSGGTAALGCLVK
DYFPEPVTVSWNSGALTSGVHTFPAVLQSSGLYSLSS
VVTVPSSSLGTQTYICNVNHKPSNTKVDKRVEPKSCD
KTHTCPPCPAPELLGGPSVFLFPPKPKDTLMISRTPE
VTCVVVDVSHEDPEVKFNWYVDGVEVHNAKTKPREEQ
YNSTYRVVSVLTVLHQDWLNGKEYKCKVSNKALPAPI
EKTISKAKGQPREPQVYTLPPSREEMTKNQVSLTCLV
KGFYPSDIAVEWESNGQPENNYKTTPPVLDSDGSFFL
YSKLTVDKSRWQQGNVFSCSVMHEALHNHYTQKSLSL
SPG
(SEQ ID NO: 159) |
| Chimeric
723C2 in
IgG1KO(723-
IgG1KO) | IgK light
Chain | (SEQ ID NO: 156)

(SEQ ID NO: 157) |
| | IgG1KO heavy
Chain | GAAGTGCAGCTGGTGGAATCTGGCGGAGGACTTGTTC
AACCTGGCGGCAGCCTGAAACTGTCTTGTGCCGCCAG
CGGCTTCACCTTCAGCGACTACTACATGAGCTGGGTC
CGACAGACCCCTGAGAAGAGACTGGAATGGGTCGCCT
ACATCAGCTCTGGCGGCGGAAGCAGCTACTACCCTGA
TAGCGTGAAGGGCAGATTCACCATCAGCCGGGACAAC
ACCAAGAACACCCTGTACCTGCAGATGTCCAGCCTGA
AGTCTGAGGACACCGCCGTGTACTACTGTGCCAGACT
GCCTCACTACTTCGCCATGGATTGTTGGGGCCAGGGC
ACATCTGTGACCGTTAGTTCTGCCTCCACCAAGGGCC
CATCGGTCTTCCCGCTAGCACCCTCCTCCAAGAGCAC
CTCTGGGGGCACAGCGGCCCTGGGCTGCCTGGTCAAG
GACTACTTCCCCGAACCGGTGACGGTGTCGTGGAACT
CAGGCGCCCTGACCAGCGGCGTGCACACCTTCCCGGC
TGTCCTACAGTCCTCAGGACTCTACTCCCTCAGCAGC
GTGGTGACCGTGCCCTCCAGCAGCTTGGGCACCCAGA
CCTACATCTGCAACGTGAATCACAAGCCCAGCAACAC
CAAGGTGGACAAGCGCGTTGAGCCCAAATCTTGTGAC
AAAACTCACACATGCCCACCGTGCCCAGCACCTGAAG
CCGCTGGGGGACCGTCAGTCTTCCTCTTCCCCCCAAA
ACCCAAGGACACCCTCATGATCTCCCGGACCCCTGAG
GTCACATGCGTGGTGGTGGACGTGAGCCACGAAGACC
CTGAGGTCAAGTTCAACTGGTACGTGGACGGCGTGGA
GGTGCATAATGCCAAGACAAAGCCGCGGGAGGAGCAG
TACAACAGCACGTACCGTGTGGTCAGCGTCCTCACCG
TCCTGCACCAGGACTGGCTGAATGGCAAGGAGTACAA
GTGCAAGGTCTCCAACAAAGCCCTCCCAGCCCCCATC
GAGAAAACCATCTCCAAAGCCAAAGGGCAGCCCCGAG
AACCACAGGTGTACACCCTGCCCCCATCCCGCGAGGA
GATGACCAAGAACCAGGTAAGTTTGACCTGCCTGGTC
AAAGGCTTCTATCCCAGCGACATCGCCGTGGAGTGGG
AGAGCAATGGGCAGCCGGAGAACAACTACAAGACCAC
GCCTCCCGTGCTGGACTCCGACGGCTCCTTCTTCCTC
TATAGCAAGCTCACCGTGGACAAGAGCAGGTGGCAGC
AGGGGAACGTCTTCTCATGCTCCGTGATGCATGAGGC
TCTGCACAACCACTACACGCAGAAGAGCCTCTCCCTG
TCTCCGGGT
(SEQ ID NO: 160) |
| | | EVQLVESGGGLVQPGGSLKLSCAASGFTFSDYYMSWV
RQTPEKRLEWVAYISSGGGSSYYPDSVKGRFTISRDN
TKNTLYLQMSSLKSEDTAVYYCARLPHYFAMDCWGQG
TSVTVSSASTKGPSVFPLAPSSKSTSGGTAALGCLVK
DYFPEPVTVSWNSGALTSGVHTFPAVLQSSGLYSLSS
VVTVPSSSLGTQTYICNVNHKPSNTKVDKRVEPKSCD
KTHTCPPCPAPEAAGGPSVFLFPPKPKDTLMISRTPE
VTCVVVDVSHEDPEVKFNWYVDGVEVHNAKTKPREEQ
YNSTYRVVSVLTVLHQDWLNGKEYKCKVSNKALPAPI
EKTISKAKGQPREPQVYTLPPSREEMTKNQVSLTCLV
KGFYPSDIAVEWESNGQPENNYKTTPPVLDSDGSFFL
YSKLTVDKSRWQQGNVFSCSVMHEALHNHYTQKSLSL
SPG
(SEQ ID NO: 161) |

TABLE 8-continued

Heavy and Light Chain DNA and Amino Acid Sequences for chimeric 723C2 in human IgG1WT, IgG1KO and IgG4Pro

| | | |
|---|---|---|
| Chimeric 723C2 IgG4Pro (723-IgG4Pro) | IgK in light Chain | (SEQ ID NO: 156) |
| | | (SEQ ID NO: 157) |
| | IgG4Pro heavy Chain | GAAGTGCAGCTGGTGGAATCTGGCGGAGGACTTGTTC AACCTGGCGGCAGCCTGAAACTGTCTTGTGCCGCCAG CGGCTTCACCTTCAGCGACTACTACATGAGCTGGGTC CGACAGACCCCTGAGAAGAGACTGGAATGGGTCGCCT ACATCAGCTCTGGCGGCGGAAGCAGCTACTACCCTGA TAGCGTGAAGGGCAGATTCACCATCAGCCGGGACAAC ACCAAGAACACCCTGTACCTGCAGATGTCCAGCCTGA AGTCTGAGGACACCGCCGTGTACTACTGTGCCAGACT GCCTCACTACTTCGCCATGGATTATTGGGGCCAGGGC ACCAGCGTGACCGTTTCTTCTGCCTCCACAAAGGGCC CTTCCGTGTTCCCCCTGGCCCCTTGCTCCCGGTCCAC CTCCGAGTCTACCGCCGCTCTGGGCTGCCTGGTCAAG GACTACTTCCCCGAGCCCGTGACCGTGTCCTGGAACT CTGGCGCCCTGACCTCCGGCGTGCACACCTTCCCTGC TGTGCTGCAGTCCTCCGGCCTGTACTCCCTGTCCTCC GTCGTGACCGTGCCCTCCTCTAGCCTGGGCACCAAGA CCTACACCTGTAACGTGGACCACAAGCCCTCCAACAC CAAGGTGGACAAGCGGGTGGAATCTAAGTACGGCCCT CCCTGCCCCCCTGCCCTGCCCCTGAATTTCTGGGCG GACCCTCCGTGTTCCTGTTCCCCCCAAAGCCCAAGGA CACCCTGATGATCTCCCGGACCCCCGAAGTGACCTGC GTGGTGGTGGACGTGTCCCAGGAAGATCCCGAGGTCC AGTTTAATTGGTACGTGGACGGCGTGGAAGTGCACAA CGCCAAGACCAAGCCCAGAGAGGAACAGTTCAACTCC ACCTACCGGGTGGTGTCCGTGCTGACCGTGCTGCACC AGGACTGGCTGAACGGCAAAGAGTACAAGTGCAAGGT GTCCAACAAGGGCCTGCCCTCCAGCATCGAAAAGACC ATCTCCAAGGCCAAGGGCCAGCCCCGCGAGCCCCAGG TGTACACCCTGCCTCCAAGCCAGGAAGAGATGACCAA GAACCAGGTGTCCCTGACCTGTCTGGTCAAGGGCTTC TACCCCTCCGATATCGCCGTGGAATGGGAGTCCAACG GCCAGCCCGAGAACAACTACAAGACCACCCCCCCTGT GCTGGACTCCGACGGCTCCTTCTTCCTGTACTCTCGG CTGACCGTGGACAAGTCCCGGTGGCAGGAAGGCAACG TCTTCTCCTGCTCCGTGATGCACGAGGCCCTGCACAA CCACTACACCCAGAAGTCCCTGTCCCTGAGCCTGGGC (SEQ ID NO: 162) |
| | | EVQLVESGGGLVQPGGSLKLSCAASGFTFSDYYMSWV RQTPEKRLEWVAYISSGGGSSYYPDSVKGRFTISRDN TKNTLYLQMSSLKSEDTAVYYCARLPHYFAMDYWGQG TSVTVSSASTKGPSVFPLAPCSRSTSESTAALGCLVK DYFPEPVTVSWNSGALTSGVHTFPAVLQSSGLYSLSS VVTVPSSSLGTKTYTCNVDHKPSNTKVDKRVESKYGP PCPPCPAPEFLGGPSVFLFPPKPKDTLMISRTPEVTC VVVDVSQEDPEVQFNWYVDGVEVHNAKTKPREEQFNS TYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLG (SEQ ID NO: 163) |

The amino acids corresponding to the change from DC to DY in H-CDR3 are underlined in the amino acid sequences in Table 8.

Humanization and Amino Acid Sequence Variants

Further variant anti-PD-1 antibodies and antibody fragments can be engineered based on the set of CDRs depicted in Tables 3 and 4. It is to be understood that in the variant anti-PD-1 antibodies and antibody fragments the amino acid sequence of the CDRs remain unchanged but the surrounding regions, e.g., FR regions can be engineered. Amino acid sequence variants of the anti-PD-1 antibody can be prepared by introducing appropriate nucleotide changes into the anti-PD-1 antibody DNA, or by peptide synthesis. Such variants include, for example, deletions from, and/or insertions into and/or substitutions of, residues within the amino acid sequences of the anti-PD-1 antibodies of the examples herein. Any combination of deletions, insertions, and substitutions is made to arrive at the final construct, provided that the final construct possesses the desired characteristics. The amino acid changes also may alter post-translational processes of the humanized or variant anti-PD-1 antibody, such as changing the number or position of glycosylation sites.

In some embodiments, the present invention includes anti-PD-1-antibodies or antibody fragments thereof having a variable heavy chain and a variable light chain, wherein the variable heavy chain amino acid sequence and the variable light chain amino acid sequence are at least 80%, at least 85%, at least 90%, at least 92.5%, at least 95%, at least 98%, or at least 99% identical to the amino acid sequences disclosed in Tables 1, 2, 5 and 6.

In some embodiments, the present invention includes anti-PD-1-antibodies or antibody fragments thereof having a variable heavy chain and a variable light chain, wherein the variable heavy chain amino acid sequence and the variable light chain amino acid sequence are at least 80%, at least 85%, at least 90%, at least 92.5%, at least 95%, at least 98%, or at least 99% identical to the amino acid sequences of SEQ ID NOs. 131, 133, 135, 137 or 139, and SEQ ID NOs. 125, 127 or 129, respectively.

In some embodiments, the present invention includes anti-PD-1 antibodies having a heavy chain and a light chain, wherein the heavy chain amino acid sequence and the light chain amino acid sequence are at least 95%, at least 98%, or at least 99% identical to the amino acid sequences disclosed in Tables 7 and 8.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody. For example, an antibody may comprise an amino acid substitution at position 297 of the human IgG1 heavy chain to abrogate oligosaccharyl-transferase enzyme complex-mediated glycosylation by replacing the asparagine 297 (e.g. N297A, N297G).

In some aspects, the present invention includes nucleic acid molecules that encode the amino acid sequence variants of the anti-PD-1 antibodies described herein. Nucleic acid molecules encoding amino acid sequence variants of an anti-PD-1 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-PD-1 antibody. For example, nucleic acid molecules according to the invention also encompass nucleic acid molecules which hybridize under stringent conditions to nucleic acid molecules as disclosed herein, whereby the term "stringent conditions" within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C.

In certain embodiments, the anti-PD-1 antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner.

In one aspect, the anti-PD-1 antibodies and antigen-binding fragments thereof can include modifications, such as glycosylation or deamidation.

In certain embodiments, it may be desirable to use an anti-PD-1 antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478. For example, antibody fragments of the invention may also be fused to human serum albumin to increase the serum half-life, if the use of a full-length IgG1 scaffold is undesirable. Such fusion proteins of the antibody fragment with human serum albumin may be advantageous in situations in which two different antibody fragments need to be fused to increase avidity, or to generate a bispecific binding protein with extended serum half-life (see e.g. WO05077042 A2).

In other embodiments, the present invention includes covalent modifications of the anti-PD-1 antibodies. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Epitope Binding

In another aspect, the invention relates to an antibody or antigen-binding fragment thereof that recognizes a specific "PD-1 antigen epitope" and "PD-1 epitope".

As used herein, the terms "PD-1 antigen epitope" and "PD-1 epitope" refer to a molecule (e.g., a peptide) or a fragment of a molecule capable of binding to an anti-PD-1 antibody or antigen-binding fragment thereof. These terms further include, for example, a PD-1 antigenic determinant recognized by any of the antibodies or antibody fragments of the present invention.

PD-1 antigen epitopes can be included in proteins, protein fragments, peptides or the like. The epitopes are most commonly proteins, short oligopeptides, oligopeptide mimics (i.e., organic compounds that mimic antibody binding properties of the PD-1 antigen), or combinations thereof.

In one aspect, an anti-PD-1 antibody of the present invention or antigen-binding fragment thereof binds specifically to a PD-1 epitope in a manner that mimics the binding of the physiological ligand resulting in antibody-mediated agonism.

The present invention also provides an anti-PD-1 antibody or antigen-binding fragment thereof that competes for binding to PD-1 with an anti-PD-1 antibody according to the present invention. In one embodiment, the present invention provides an anti-PD-1 antibody or antigen-binding fragment thereof that competes for binding to PD-1 with any one of Antibody A, Antibody B, Antibody C, Antibody D or Antibody E described herein. Competition assays may be conducted for example as described in PLoS One. 2014; 9(3): e92451 using a biosensor, or PLoS One 2020 Mar. 5; 15(3):e0229206, or by a method disclosed herein.

Therapeutic Uses

In one embodiment, the anti-PD-1 antibodies of the invention or antigen-binding fragments thereof are useful for treating or preventing PD-1 pathway disorders.

In another embodiment, the anti-PD-1 antibodies of the invention or antigen-binding fragments thereof are useful as a medicament.

Accordingly, in one embodiment, the present invention provides a method of modulating the interaction between PD-1 and PD-L1 in a human patient comprising administering to said human patient a composition comprising an anti-PD-1 antibody or antigen-binding fragment thereof according to the present invention in an amount sufficient to activate the PD-1 pathway in said human patient. In one embodiment, the present invention provides an anti-PD-1 antibody or antigen-binding fragment thereof according to the present invention for use in modulating the interaction between PD-1 and PD-L1 in a human patient. In one embodiment, the present invention provides the use of an anti-PD-1 antibody or antigen-binding fragment thereof according to the present invention in the manufacture of a medicament for modulating the interaction between PD-1 and PD-L1 in a human patient.

In one embodiment, the present invention provides a method of attenuating PD-1 expressing T cell activity in a human patient comprising administering to said human patient a composition comprising an anti-PD-1 antibody or antigen-binding fragment thereof according to the present invention in an amount sufficient to down-modulate an immune response in said human patient. In one embodiment, the present invention provides an anti-PD-1 antibody or antigen-binding fragment thereof according to the present invention for use in attenuating PD-1 expressing T cell activity in a human patient. In one embodiment, the present invention provides the use of an anti-PD-1 antibody or antigen-binding fragment thereof according to the present invention in the manufacture of a medicament for attenuating PD-1 expressing T cell activity in a human patient.

In one embodiment, a PD-1 pathway disease or disorder is systemic sclerosis (SSc), systemic lupus erythematosus, polymyositis, giant cell arteritis, psoriasis, psoriatic arthritis, ankylosing spondylitis or inflammatory bowel disease. Accordingly, in one embodiment, the present invention provides a method of treating or preventing systemic sclerosis (SSc), systemic lupus erythematosus, polymyositis, giant cell arteritis, psoriasis, psoriatic arthritis, ankylosing spondylitis or inflammatory bowel disease in a human patient comprising administering to said human patient a composition comprising an anti-PD-1 antibody or antigen-binding fragment thereof according to the present invention. In one embodiment, the present invention provides an anti-PD-1 antibody or antigen-binding fragment thereof according to the present invention for use in treating or preventing systemic sclerosis (SSc), systemic lupus erythematosus, polymyositis, giant cell arteritis, psoriasis, psoriatic arthritis, ankylosing spondylitis or inflammatory bowel disease in a human patient. In one embodiment, the present invention provides the use of an anti-PD-1 antibody or antigen-binding fragment thereof according to the present invention in the manufacture of a medicament for treating or preventing systemic sclerosis (SSc), systemic lupus erythematosus, polymyositis, giant cell arteritis, psoriasis, psoriatic arthritis, ankylosing spondylitis or inflammatory bowel disease in a human patient.

In one embodiment, a PD-1 pathway disease or disorder is chronic or acute, such as chronic inflammatory disease or acute inflammatory disease. In one embodiment, a PD-1 pathway disease or disorder is arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, psoriatic arthritis, vasculitis, surgical adhesions, stroke, Type I Diabetes, Lyme disease, meningoencephalitis, autoimmune uveitis, multiple sclerosis, lupus (such as systemic lupus erythematosus), Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia, infertility related to lack of fetal-maternal tolerance, Sjogren's Syndrome, vitiligo, myasthenia gravis or systemic sclerosis.

Accordingly, in one embodiment, the present invention provides a method of treating or preventing one of the above diseases or disorders in a human patient comprising administering to said human patient a composition comprising an anti-PD-1 antibody or antigen-binding fragment thereof according to the present invention. In one embodiment, the present invention provides an anti-PD-1 antibody or antigen-binding fragment thereof according to the present invention for use in treating or preventing one of the above diseases or disorders in a human patient. In one embodiment, the present invention provides the use of an anti-PD-1 antibody or antigen-binding fragment thereof according to the present invention in the manufacture of a medicament for treating or preventing one of the above diseases or disorders in a human patient.

In one aspect, the PD-1 antibody or antigen-binding fragment thereof for use or in a use as described above or in a method as described above is an agonist anti-PD-1 antibody or antigen-binding fragment thereof.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the PD-1 protein (or fragment thereof) to be purified, and thereafter the support is washed with a suitable solvent that will remove substantially all the material in the sample except the PD-1 protein, which is bound to the immobilized antibody. Finally, the support is washed with another suitable solvent that will release the PD-1 protein from the antibody.

The anti-PD-1 antibodies and fragments thereof of the invention as disclosed herein are also useful in diagnostic assays to detect and/or quantify PD-1 protein, for example, detecting PD-1 expression in specific cells, tissues, or serum.

It will be advantageous in some embodiments, for example, for diagnostic purposes to label the antibody with a detectable detectable moiety. Numerous detectable labels are available, including radioisotopes, fluorescent labels, enzyme substrate labels, quantum dots and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available, or e.g. any of the following fluorescent labels: dialkylaminocoumarin, rhodamine isothiocyanate, Alexa 350, Alexa 430, Alexa Fluor 488, Alexa Fluor 532, Alexa Fluor 546, Alexa Fluor 568, Alexa Fluor 594, Alexa Fluor 633, Alexa Fluor 660, Alexa Fluor 680, AMCA, aminoacridine, BODIPY 630/650, BODIPY 650/665, BODIPY-FL, BODIPY-R6G, BODIPY-TMR, BODIPY-TRX, BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin,.DM-NERF, Eosin, Erythrosin, Fluorescein, FA, Hydroxycoumarin, IRDyes (IRD40, IRD 700, IRD 800), JOE, Lissamine rhodamine B, Marina Blue, Methoxy coumarin, Naphtho fluorescein, Oregon Green 488, Oregon Green 500, Oregon Green 514, Pacific Blue, PyMPO, 5-carboxy-4',5,-dichloro-2',7'-dimethoxy fluorescein, 5-carboxy-2',4',5,7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, fluorescein, HEX, 6-JOE, NBD (7-nitrobenz-2-oxa-I,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, aUopycocyanin, allococyanin B, phycocyanin C, phycocyanin R, thiamine, phycoerythrocyanin, phycoerythrin R, REG, Rhodamine Green, rhodamine isothiocyanate, Rhodamine Red, TAMRA, TET, TRIT (tetramethyl rhodamine isothiol), Tetramethylrhodamine, or Texas Red. The fluorescent labels can be conjugated to the antibody via known techniques, such as those disclosed in Current Protocols in Immunology, supra, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methyl-umbelliferyl-β-D-galactosidase.

Numerous other enzyme-substrate combinations are available to those skilled in the art. For a general review of these, see U.S. Pat. Nos. 4,275,149 and 4,318,980.

In another embodiment, an anti-PD-1 antibody or antibody fragment of the invention is used unlabeled and detected with a labeled antibody that binds the anti-PD-1antibody or fragment thereof. For example, labeled anti-human Fc, or anti-human Fab antibodies may be used to detect the unlabeled anti-PD-1 antibody or fragment. The use of an unlabeled anti-PD-1 antibody or fragments thereof according to the invention may be advantageous to achieve a better tissue penetration, as the fluorescent label will increase the molecular weight and/or increase hydrophobicity of the antibody or antibody fragment it is fused to thereby reducing tissue penetration.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Diagnostic Kits.

A humanized anti-PD-1 antibody of the invention can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Diagnostic Kits

An anti-PD-1 antibody or fragment thereof can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Compositions and Administration Thereof

A composition comprising an anti-PD-1 antibody or an antigen-binding fragment thereof according to the invention can be administered to a subject having or at risk of the PD-1 pathway diseases or disorders described herein. The invention further provides for the use of an anti-PD-1 antibody or an antigen-binding fragment thereof in the manufacture of a medicament for prevention or treatment of a PD-1 pathway disease or disorder. The term "subject" as used herein means any mammalian patient to which an anti-PD-1 antibody or an antigen-binding fragment thereof can be administered, including, e.g., humans and certain non-human mammals, such as primates, and dogs. Subjects specifically intended for treatment using the methods described herein include humans. The anti-PD-1 antibody or an antigen-binding fragment thereof of the invention can be administered either alone or in combination with other compositions.

In one aspect, the present invention also provides pharmaceutical compositions comprising an antibody or antigen-binding fragment thereof of the present invention.

Various delivery systems are known and can be used to administer the anti-PD-1 antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-PD-1 antibody or an antigen-binding fragment thereof can be administered, for example by infusion, bolus or injection, and can be administered together with other biologically active agents. Administration can be systemic or local. Formulations for such injections may be prepared in, for example, prefilled syringes.

An anti-PD-1 antibody or an antigen-binding fragment thereof can be administered as pharmaceutical compositions comprising a therapeutically effective amount of the anti-PD-1 antibody or an antigen-binding fragment thereof and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-PD-1 antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-PD-1 antibody or antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-PD-1 antibody or antigen-binding fragment thereof that is effective in the treatment or prevention PD-1 pathway diseases or disorders can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-PD-1 antibody or antigen-binding fragment thereof can be determined in cell cultures or experimental animals by standard pharmaceutical procedures for determining the $ED_{50}$ (the dose therapeutically effective in 50% of the population). An anti-PD-1 antibody or antigen-binding fragment thereof that exhibits a large therapeutic index is preferred.

The data obtained from the cell culture assays and animal studies can be used in formulating a range of dosage for use in humans. The dosage of the anti-PD-1 antibody or antigen-binding fragment thereof typically lies within a range of circulating concentrations that include the $ED_{50}$ with little or no toxicity. The dosage may vary within this range depending upon the dosage form employed and the route of administration utilized. For any anti-PD-1 antibody or antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

In one embodiment, the anti-PD-1-antibody is administered at regular intervals.

In some embodiments, antibodies of the present invention can be formulated to doses, which include for example from 1 mg/ml to 250 mg/ml, for example from 20 mg/ml to 200 mg/ml.

In some embodiments, the pharmaceutical compositions comprising the anti-PD-1 antibody or antigen-binding fragment thereof can further comprise a therapeutic agent, either conjugated or unconjugated to the binding agent.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-PD-1 antibody or antigen-binding fragment thereof is administered concurrently with a therapeutic agent. In another specific embodiment, the therapeutic agent is administered prior or subsequent to administration of the anti-PD-1 antibody or antigen-binding fragment thereof.

Polynucleotides, Vectors, Host Cells, and Recombinant Methods

The present invention relates to isolated polynucleotides that comprise a sequence encoding an anti-PD-1 antibody or antigen-binding fragment thereof, vectors, and host cells comprising the polynucleotides, and recombinant techniques for production of the antibody. The isolated polynucleotides can encode any desired form of the anti-PD-1 antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-PD-1 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-PD-1 antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-PD-1 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-PD-1 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-PD-1 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-PD-1 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trpl lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-PD-1 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-PD-1 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657 or Baghban et al. Molecular Biotechnology (2019) 61:365-384. Yeast enhancers also are advantageously used with yeast promoters.

Anti-PD-1 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding an anti-PD-1 antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-PD-1 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PD-1 antibody. One useful transcription termination component is the bovine growth hormone polyadenylation region. See WO94/11026 and the expression vector disclosed therein. In some embodiments, anti-ANGPT2 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and

*Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-PD-1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger.*

Suitable host cells for the expression of glycosylated anti-PD-1 antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of Autographa californica NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

The anti-PD-1 antibodies or antigen-binding fragments thereof can also be incorporated in viral vectors, i.e. the polynucleotide encoding for the anti-PD-1 antibody or antigen-binding fragment thereof is introduced into the viral vector and then expressed in the body of the patient after infection with the virus.

In another aspect, expression of the anti-PD-1 antibody or antigen-binding fragment thereof is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/–DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for or antigen-binding fragment thereof antibody production and cultured in conventional nutrient media modified as appropriate for inducing promoters, selecting transformants, or amplifying the genes encoding the desired sequences.

The host cells used to produce an antibody or antigen-binding fragment thereof described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575).

A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, in particular under high stringency conditions, as defined herein, to all or a portion (e.g., the portion encoding the variable region) of the nucleotide sequence represented by isolated polynucleotide sequence(s) that encode an anti-PD-1 antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-PD-1 polypeptide (e.g., a heavy chain or light chain variable region), or its complement. Hybridizing nucleic acids of the type described herein can be used, for example, as a cloning probe, a primer, e.g., a PCR primer, or a diagnostic probe. In one aspect, "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

In one embodiment, the present invention relates to an isolated polynucleotide comprising a nucleotide sequence encoding a heavy chain variable region comprising the amino acid sequence of any one of SEQ ID NOs: 108 to 123.

In one embodiment, the present invention relates to an isolated polynucleotide comprising a nucleotide sequence encoding a light chain variable region comprising the amino acid sequence of any one of SEQ ID NOs: 92 to 107.

In one embodiment, the present invention relates to an isolated polynucleotide comprising a nucleotide sequence encoding a heavy chain variable region comprising the amino acid sequence of any one of SEQ NO: 131, SEQ NO: 133, SEQ NO: 135, SEQ NO: 137 or SEQ NO: 139.

In one embodiment, the present invention relates to an isolated polynucleotide comprising the nucleotide sequence of any one of SEQ NO: 130, SEQ NO: 132, SEQ NO: 134, SEQ NO: 136 or SEQ NO: 138.

In one embodiment, the present invention relates to an isolated polynucleotide comprising a nucleotide sequence encoding a light chain variable region comprising the amino acid sequence of any one of SEQ NO: 125, SEQ NO: 127 or SEQ NO: 129.

In one embodiment, the present invention relates to an isolated polynucleotide comprising the nucleotide sequence of any one of SEQ NO: 124, SEQ NO: 126 or SEQ NO: 128.

In one embodiment, the present invention relates to an isolated polynucleotide comprising a nucleotide sequence encoding a heavy chain comprising the amino acid sequence of any one of SEQ NO: 143, SEQ NO: 147, SEQ NO: 149, SEQ NO: 153 or SEQ NO: 155.

In one embodiment, the present invention relates to an isolated polynucleotide comprising the nucleotide sequence of any one of SEQ NO: 142, SEQ NO: 146, SEQ NO: 148, SEQ NO: 152 or SEQ NO: 154.

In one embodiment, the present invention relates to an isolated polynucleotide comprising a nucleotide sequence encoding a light chain comprising the amino acid sequence of any one of SEQ NO: 141, SEQ NO: 145 or SEQ NO: 151.

In one embodiment, the present invention relates to an isolated polynucleotide comprising the nucleotide sequence of any one of SEQ NO: 140, SEQ NO: 144 or SEQ NO: 150.

In one embodiment, the present invention relates to an isolated polynucleotide comprising a nucleotide sequence encoding a heavy chain comprising the amino acid sequence of any one of SEQ NO: 159, SEQ NO: 161 or SEQ NO: 163.

In one embodiment, the present invention relates to an isolated polynucleotide comprising the nucleotide sequence of any one of SEQ NO: 158, SEQ NO: 160 or SEQ NO: 162.

In one embodiment, the present invention relates to an isolated polynucleotide comprising a nucleotide sequence encoding a light chain comprising the amino acid sequence of SEQ NO: 157.

In one embodiment, the present invention relates to an isolated polynucleotide comprising the nucleotide sequence of SEQ NO: 156.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-PD-1 antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1

Antibody Generation (Immunization)

MHC Type A, C, D, E, H, G strain mice were immunized with recombinant monomeric human PD-1 or human PD-1- humanFc-His protein. The gene symbol for this recombinant protein is PDCD1 and the GeneID is 5133. Serology was then assessed by flow cytometry using CHO-human PD-1 cells, expressing human PD-1 antigen for binding. Selected serologically positive mice were given a final boost before B-cell isolation. All selected mice exhibited positive antibody titers in the sera. At positive serology, splenocytes were harvested for recovery of antigen-specific B-cells. All procedures were carried out in accordance with protocol approved by IACUC (Institutional Animal Care and Use Committee).

Example 2

Production of Humanized Anti-PD-1 Antibodies

Mouse lead antibody 723C2 was converted to chimeric antibodies consisting of the mouse variable domain of 723C2 and a human constant IgG1WT, IgG1 KO, or IgG4Pro domain. Sequences of mouse antibody 723C2 light chain variable region (Vκ) and heavy chain variable region (VH) are shown in Tables 1 and 2 herein above. The IgG4Pro has one replacement mutation (Ser228Pro) that prevents Fab-arm exchanging. The IgG1 KO has two mutations in the hinge region, Leu234Ala and Leu235Ala, to reduce effector function (ADCC). Chimeric antibodies are generated to confirm the function of the antibody and to ensure the correct sequence has been obtained. Sequences of the chimeric 723C2 in human IgG1WT, IgG1 KO, and IgG4Pro formats are shown in Table 8. The chimeric 723C2 in human IgG1WT and IgG4Pro contains a mutation in H-CDR3, DC to DY. However, the chimeric 723C2 in human IgG1 KO does not have the mutation. The mutation in this site is highlighted in Table 8. The variable region of the antibody is then humanized through a design and screening process. A library was made where human and mouse residues were varied in such a way that in any given position there could either be a human or mouse residue. Such a library was made for those amino acids that were different between human germline and mouse antibody. Only the clones that retain the function of the parent mouse antibody were selected. Representative humanized variable regions for antibody 723C2 are shown in Tables 5 and 6.

In this manner, Antibody A, Antibody B, Antibody C, Antibody D, and Antibody E were humanized antibodies derived from mouse antibody 723C2 (cloned into a human IgG4Pro/kappa backbone). Antibodies A, B, C, D and E are shown in Table 7.

Example 3

Binding of Antibodies to Recombinant PD-1 Protein

A) Kinetics and affinity of chimeric anti-PD-1 antibodies in human IgG4Pro backbone binding to recombinant human PD-1 are shown below (Table 9). Kinetics and binding affinities were measured using the ProteOn™ XPR36 (Bio-rad, Hercules, CA) surface plasmon resonance optical biosensor using material generated from transient transfection following single column purification.

TABLE 9

| Antibody | ka(1/Ms) | kd(1/s) | KD(nM) |
|---|---|---|---|
| Chimeric 306E6 | 1.36E+05 | 7.65E−03 | 56.4 |
| Chimeric 307A3 | 1.16E+05 | 7.40E−03 | 63.5 |
| Chimeric 313C12 | 6.71E+04 | 5.77E−05 | 0.859 |
| Chimeric 414A12 | 1.80E+05 | 2.69E−04 | 1.50 |
| Chimeric 502H1 | 5.47E+04 | 3.49E−04 | 6.39 |
| Chimeric 701C1 | 2.34E+04 | 3.05E−04 | 13.0 |
| Chimeric 701E9 | 8.83E+04 | 1.43E−04 | 1.62 |
| Chimeric 703D10 | 3.46E+04 | 3.29E−04 | 9.49 |
| Chimeric 708E4 | 4.31E+04 | 3.48E−04 | 8.08 |
| Chimeric 709A6 | 8.74E+04 | 4.83E−04 | 5.52 |
| Chimeric 718C2 | 2.84E+04 | 1.13E−04 | 3.98 |
| Chimeric 723C2 | 2.26E+05 | 5.82E−04 | 2.58 |
| Chimeric 803E6 | 1.06E+05 | 5.30E−04 | 5.02 |
| Chimeric 811G3 | 8.77E+04 | 8.01E−04 | 9.14 |
| Chimeric 814E10 | 8.07E+04 | 1.49E−04 | 1.85 |
| Chimeric 820C3 | 1.06E+04 | 2.86E−04 | 2.71 |

B) Affinities were measured for humanized anti-PD-1 antibodies derived from mouse antibody 723C2. Kinetic binding data, measured using the ProteOn™ XPR36 (Bio-rad, Hercules, CA) surface plasmon resonance optical biosensor and globally fit to a 1:1 binding model, demonstrated the interactions with recombinant human PD-1 to be in the range of 1 nM~10 nM (Table 10). Antibody PD1AB-6-4P (antibody in IgG4Pro backbone disclosed in WO2017/058859 to Celgene) was also tested.

TABLE 10

| | ka (1/Ms) | kd (1/s) | KD (nM) |
|---|---|---|---|
| Chimeric723C2 in IgG4Pro | 2.26E+05 | 5.82E−04 | 2.58 |
| Antibody A | 1.59E+05 | 4.34E−04 | 2.73 |
| Antibody B | 2.59E+05 | 4.21E−04 | 1.62 |
| Antibody C | 1.75E+05 | 4.63E−04 | 2.65 |
| Antibody D | 2.22E+05 | 5.74E−04 | 2.58 |
| Antibody E | 1.78E+05 | 4.92E−04 | 2.77 |
| PD1AB-6-4P | 2.10E+05 | 4.60E−03 | 22.0 |

C) Affinity and kinetic data for the anti-PD-1 antibodies binding to cynomologous PD-1 were measured on the ProteOn™ XPR36 surface plasmon resonance optical biosensor, and globally fit to a 1:1 binding model (Table 11). Antibody, PD1AB-6-4P was also tested.

TABLE 11

| Antibody | ka (1/Ms) | kd (1/s) | KD (nM) |
|---|---|---|---|
| Chimeric 723C2 in IgG4Pro | 1.85E+05 | 7.21E−03 | 38.9 |
| Antibody A | 1.78E+05 | 4.73E−03 | 26.5 |
| Antibody B | 1.69E+05 | 5.58E−03 | 32.9 |
| Antibody C | 1.54E+05 | 6.33E−03 | 41.0 |
| Antibody D | 1.49E+05 | 6.74E−03 | 45.2 |
| Antibody E | 1.73eE+05 | 6.63E−03 | 38.2 |
| PD1AB-6-4P | NA | NA | 25.0 |

D) Molecular Selectivity to Human PD-1

Selectivity of anti-PD-1 antibody to human PD-1 protein in a cell-based assay was evaluated by flow cytometry. Parental Jurkat cells that do not express the human PD-1 protein or Jurkat cells expressing the human PD-1 protein were incubated with the anti-PD-1 antibody labeled with AlexaFluor 647 at the concentrations indicated below. As a control, parental and PD-1 expressing Jurkat cells were incubated with anti-TNP isotype control antibodies. Following incubation, the cells were washed to remove non-bound antibody, fixed in PFA, and then washed in staining buffer.

Binding of the antibody to the Jurkat cells was evaluated by flow cytometry. Unstained cells were also evaluated by flow cytometry as a negative control. The anti-PD-1 antibody selectively binds to human PD-1 up to at least 1 micromolar, as indicated by dose-dependent antibody binding to Jurkat cells that express the human PD-1 protein and the lack of binding of AlexaFluor 647 labeled anti-PD-1 antibody to parental Jurkat cells lacking PD-1 expression. The results of a representative experiment using Antibody C (Ab C) are shown in FIG. 1.

Example 4

Competition Binding Assay of Human PD-1-Fc Binding to Human PD-L1-Fc

Figure 2A:
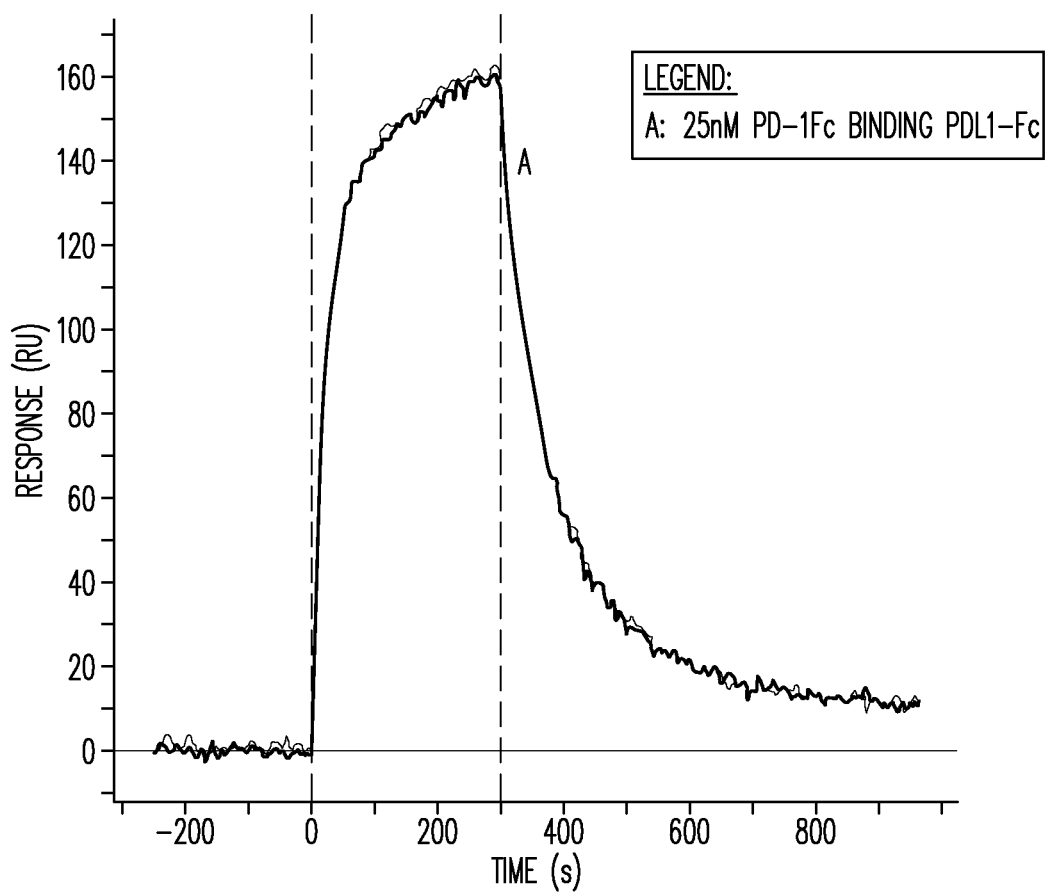
FIG. 2A, 2B: Competition binding assay of human PD-1-Fc binding to human PD-L1-Fc. Sensorgram depicting the binding curve of 25 nM PD-1-Fc to PD-L1-Fc amine coupled on the GLM chip surface (FIG. 2A). Sensorgrams of Antibody C, MK-3475, and PD1AB-6-4P (500 nM) pre-mixed with 25 nM PD-1-Fc binding to PD-L1-Fc amine coupled to the GLM chip surface (FIG. 2B).
Figure 2B:
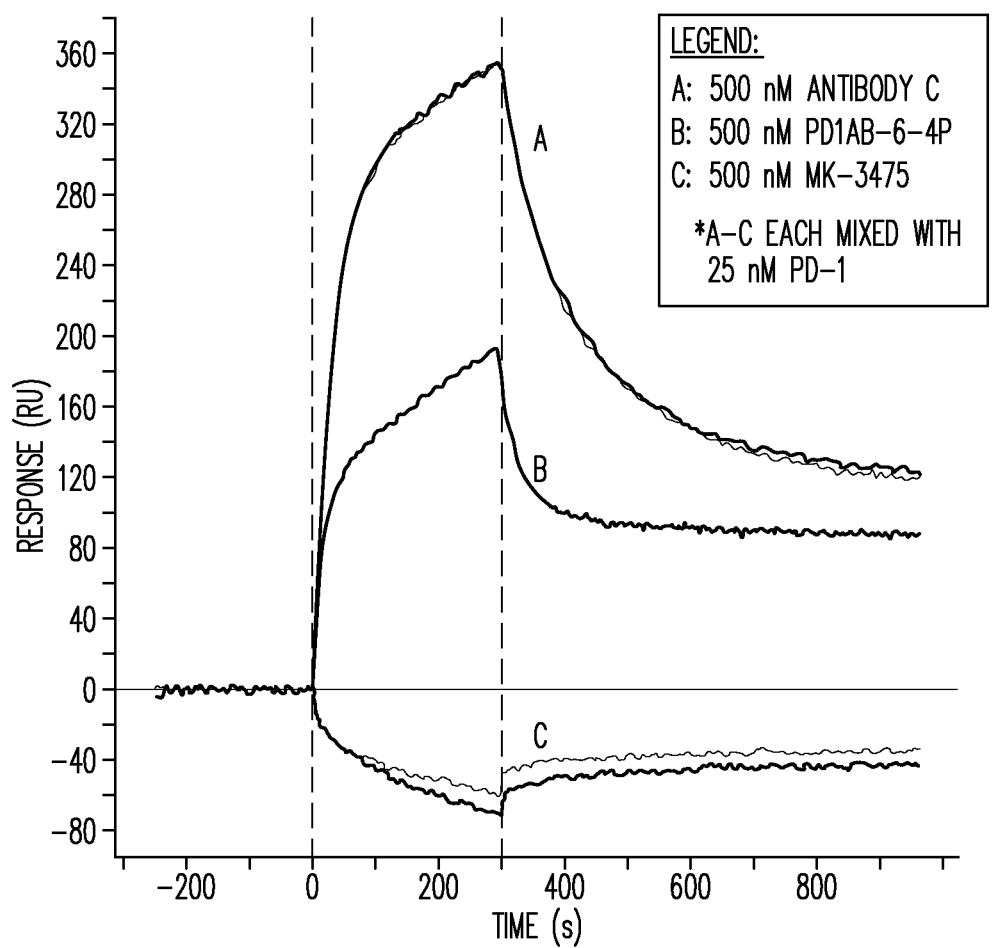

Human PD-L1-Fc was amine coupled onto channels 1-3 of a GLM chip on a BioRad ProteOn™ XPR36 surface plasmon resonance optical biosensor instrument at a concentration of 60 µg/mL; the three test antibodies, Antibody C, MK-3475 (pembrolizumab), and PD1AB-6-4P were amine coupled onto channels 4, 5, and 6, respectively at 30 µg/mL. Human PD1-Fc was injected across channels 1-6 on the chip surface at a concentration of 25 nM. The sensorgram indicates the specific binding between PD-L1 and the PD-1 receptor (FIG. 2A). 500 nM Antibody C, MK-3475, and PD1AB-6-4P were pre-mixed with 25 nM PD1-Fc and injected as analyte across all channels on the chip to assess whether the individual antibodies inhibit binding of PD-L1 to PD-1. Both Antibody C and PD1AB-6-4P are noncompetitive with PD-L1 for binding to the PD-1 antigen as demonstrated by the sensorgrams. MK-3475 and PD-L1 are potential binding blockers of one another with PD-1 based on the non-binding sensorgrams observed in the competition assay (FIG. 2B).

Example 5

Enhanced Binding of PD-L1 to PD-1 in the Presence of Anti-PD-1 Agonist Antibody

PD-1/PD-L1 interactions were interrogated in the presence of the PD-1 agonist antibody 723C2 in human IgG4Pro backbone without the DC to DY mutation in H-CDR3. Multiple assays were utilized to demonstrate that antibody 723C2 enhanced the binding of PD-L1 to PD-1. A biochemical ELISA-based assay was utilized to evaluate the binding of PD-1 to platebound PD-L1 (BPS Bioscience). White 96-well microplates were coated with 50 µl of PD-L1 at 2 µg/ml in PBS overnight at 4° C. Supernatants were removed and plates were washed three times with 1× immunobuffer provided by the manufacturer BPS Bioscience (Cat #72005) followed by blocking with blocking buffer for one hour at room temperature (RT). Antibodies, along with the relevant controls, were added followed by addition of PD-1 biotin at 0.5 ng/ml (10 ng) for two hours at room temperature. Plates were blocked with blocking buffer for 10 minutes. A streptavidin horseradish peroxidase secondary antibody was added to the washed plates for an hour followed by washing with PD-1 assay buffer. Plates were blocked for 10 minutes. Chemilumiscent substrate mixture was added to the plate just before reading. The chemiluminescent signal was read on a luminometer (Envision) or on a microtiter plate capable of reading chemiluminescence.

Figure 3A:
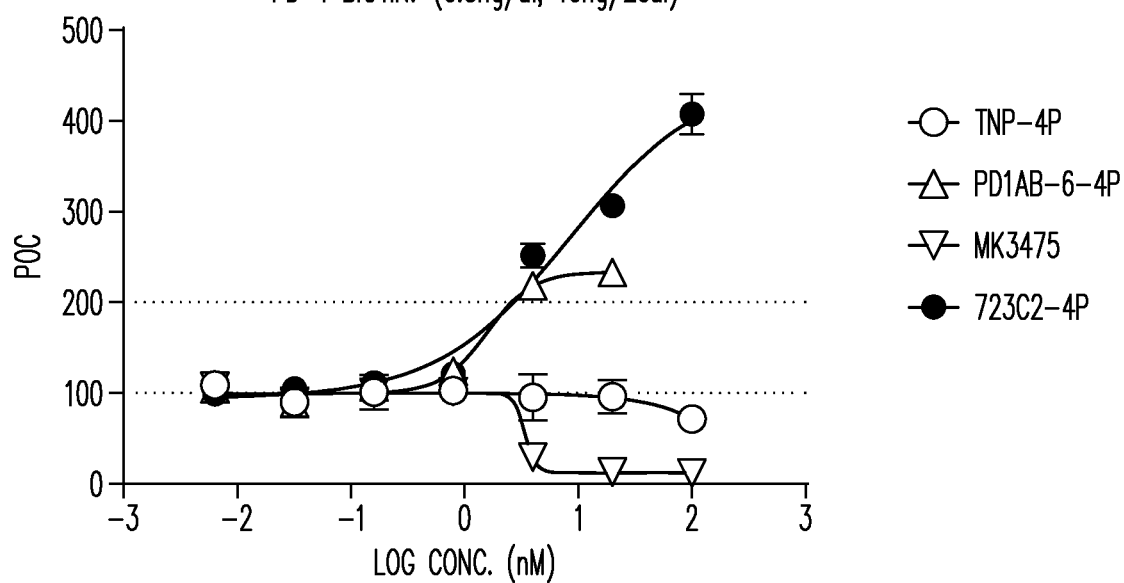
FIG. 3A, 3B, 3C, 3D: Enhanced binding of PD-L1 to PD-1 in the presence of anti-PD-1 agonist antibody. PD-1 Biotin: PD-L1 interaction assay (FIG. 3A). CHO PD-1-PD-L1 Delphia-Eu TRF assay (FIGS. 3B and 3D). CHO PD-1: Biotin PD-L1 binding assay (FIG. 3C).

Enhanced interactions of PD-1 with PD-L1 was observed in the presence of antibody 723C2, as indicated by increased chemiluminescence signal compared to isotype control treated samples (FIG. 3A). Antibody 723C2 is designated as 723C2-4P in FIG. 3A. This is in contrast to MK3475, a known anti-PD-1 antagonist antibody, which blocked the PD-L1-PD-1 interaction. Antibody PD1AB-6-4P demonstrated limited enhancement of PD-1-PD-L1 in this assay (FIG. 3A).

A cell-based assay was utilized to confirm the ELISA-based results demonstrating the enhancement of PD-1/PD-L1 interactions in the presence of the antibody 723C2. Here, the interaction of PD-1/PD-L1 was evaluated by measuring the binding of soluble PD-1 to CHO cells over-expressing PD-1 with a DELFIA (dissociation-enhanced lanthanide fluorescence immunoassay) receptor-ligand binding assay (Perkin Elmer).

Figure 3B:
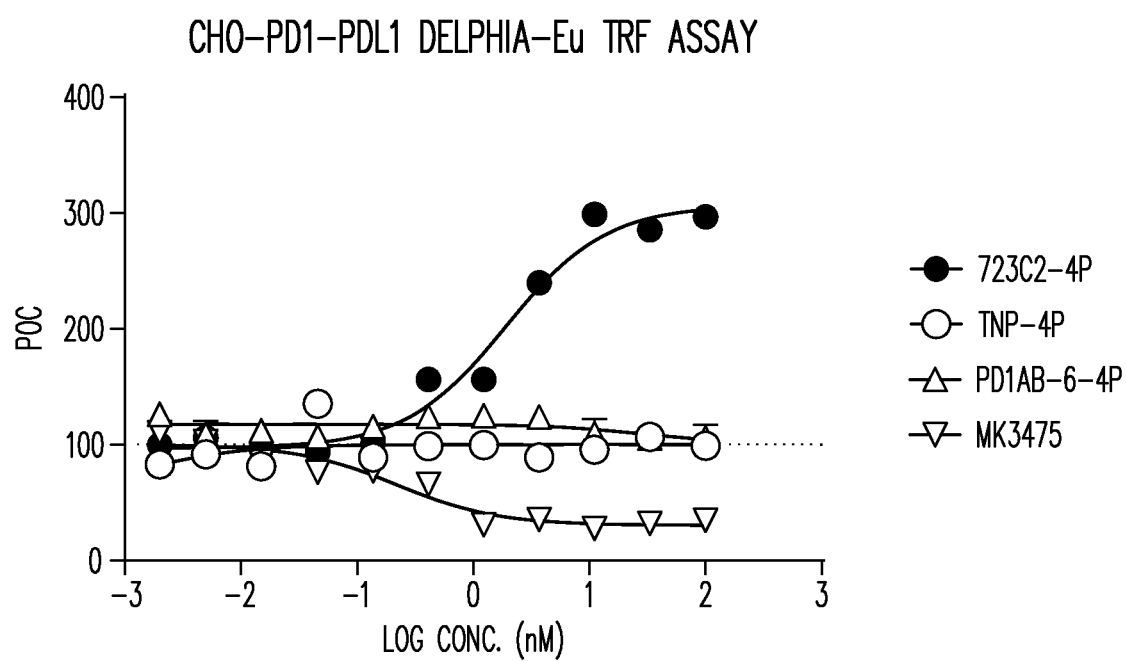

10,000 cells were plated and incubated overnight at 37° C.+5% CO2 incubator (humidified incubator). Biotin labeled PD-L1 EC 10 (130 nM) and 10 µl of PD-1 antibody was added to each well and incubated at RT for 1 hour. Plates were washed twice with 50 µl of 1×TRF Wash Buffer. 20 µl of Eu-Streptavidin reagent was added to the assay plate, and incubated at room temperature for one hour. Enhancement Solution was added and incubated for 30 minutes at RT. Plates were read on a Fluorescence Plate Reader (Excitation: 320 or 340 nm, Emission: 615 nm). In this assay, and in confirmation of the ELISA assay, the presence of antibody 723C2 in this cell-based assay enhanced the PD-1/PD-L1 interactions (FIG. 3B). Antibody 723C2 is designated as 723C2-4P in FIG. 3B.

Figure 3C:
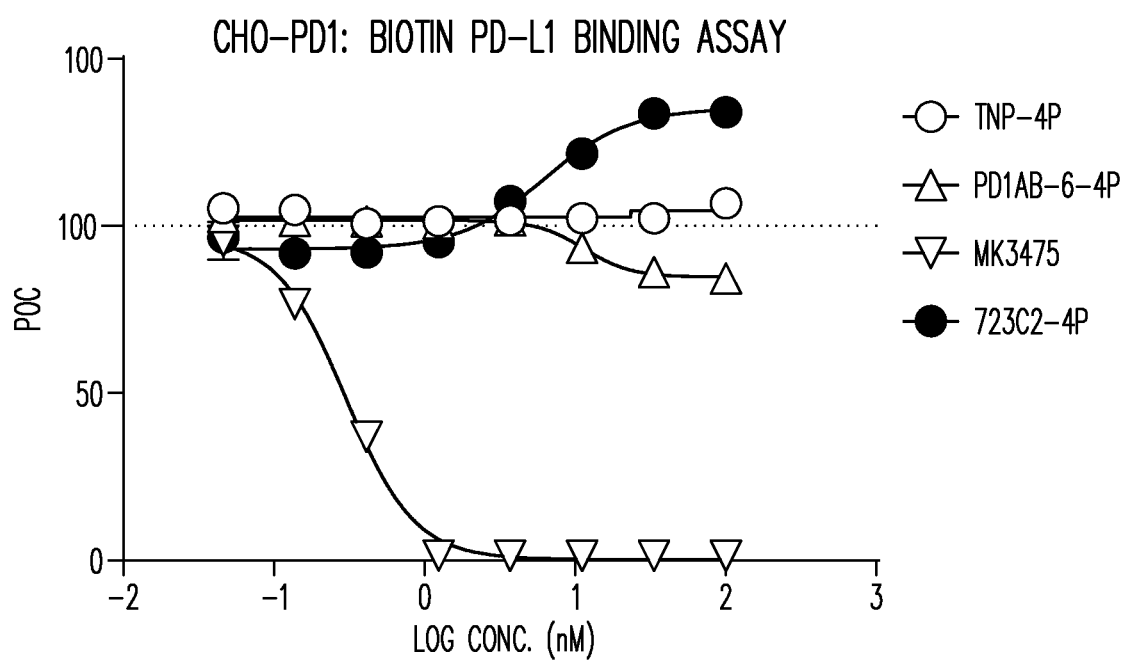

A second cell-based assay where PD-1 was expressed on CHO cells was also utilized to evaluate PD-1/PD-L1 interactions. In this assay, PD-L1-multimer binding to CHO cells expressing PD-1 was measured by flow cytometry. 50 µl of 2×10$^6$ cells/ml were added to each well (100,000 cells/well). Cells were centrifuged and re-suspended in 50 µl of the indicated antibody concentrations and incubated for 60 minutes on ice. PDL1-biotin and Streptavidin-APC were combined in stain buffer (1 µg/ml PDL1-biotin+0.25 µg/ml Streptavidin-APC). Add 50 µl of 2×PDL1-biotin/Streptavidin-APC mixture to the cells and incubate on ice for 60 minutes. Cells were washed and resuspended in 180 µl stain buffer+20µ PFA and data was acquired on a BD LSR II. As indicated in FIG. 3C, this cell-based assay also demonstrated the enhanced binding of PD-L1 to PD-1 in the presence of antibody 723C2. Antibody PD1AB-6-4P had no effect on PD-L1 binding, while the MK3475 antagonist antibody inhibited binding of PD-L1 to PD-1 (FIG. 3C). Antibody 723C2 is designated as 723C2-4P in FIG. 3C.

A CHO PD-1-PD-L1 Delphia-Eu TRF assay as described above was also performed with Antibody C, antibody PD1AB-6-4P, Antibody 1-4Pro, antibody PD1B1090-4Pro, antibody PD1B1094-4Pro and antibody ANB-030-4Pro. Antibody 1-4Pro comprises the heavy chain and light chain variable regions of Antibody 1 described in WO2019/168745 to Eli Lilly, in a IgG4-Pro backbone, Antibody PD1B1090-4Pro and antibody PD1B1094-4Pro comprise the heavy chain and light chain variable regions of PD1 B1090 and PD1 B1094, respectively, described in WO2018/226580 to Janssen Biotech, in a IgG4-Pro backbone. Antibody ANB-030-4Pro comprises the heavy chain and light chain variable regions of antibody ANB-030, described under CAS number CAS 2412764-40-8 in a IgG4-Pro backbone (also corresponds to the heavy chain and light chain variable regions of APE12537, described in WO2020/247648 to Anaptysbio). An anti-TNP antibody in IgG4-Pro backbone was also included.

Figure 3D:
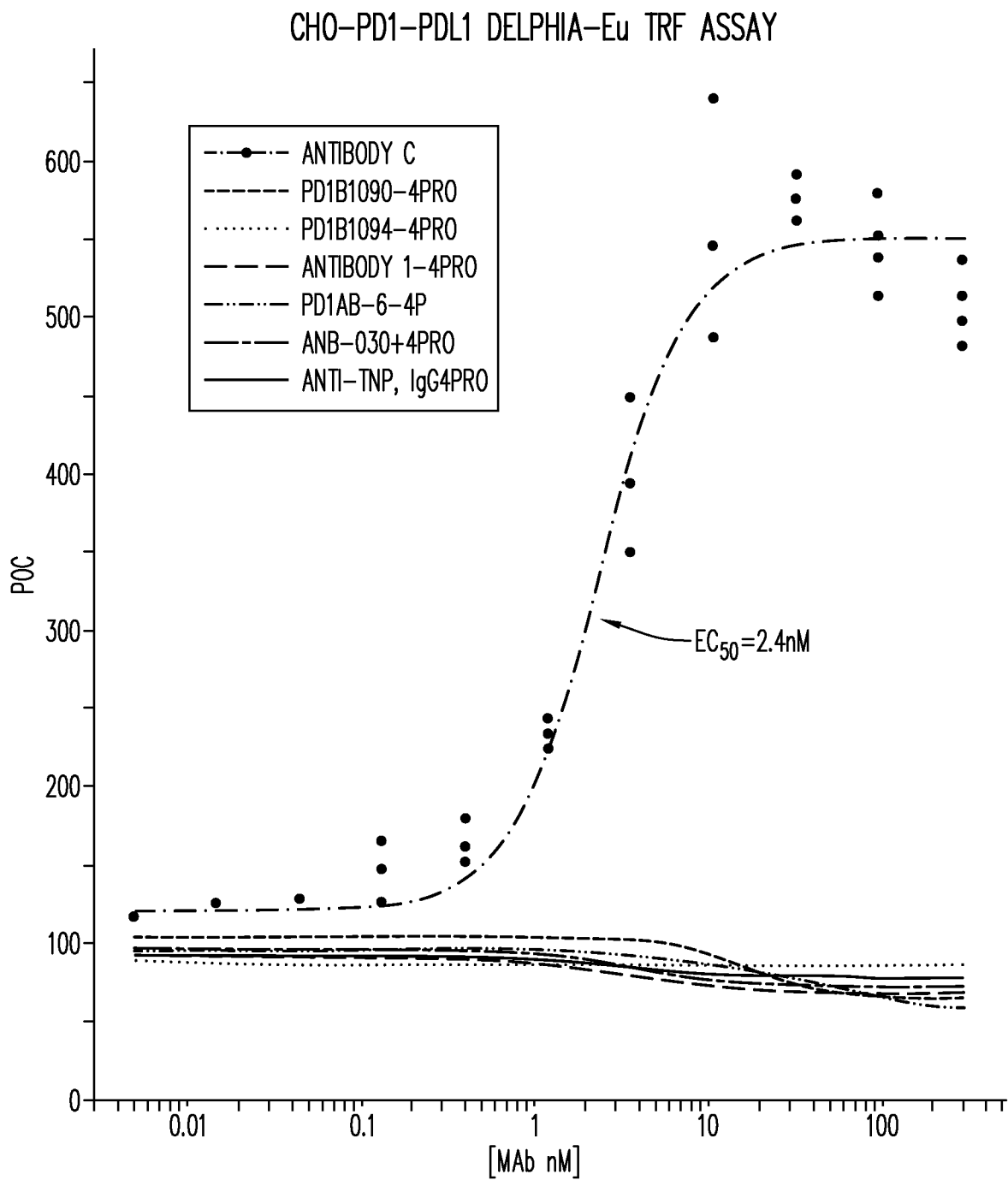

Antibody C showed consistent (N=3) enhancement of PD-1\PDL-1 binding in a concentration dependent manner (FIG. 3D). All other anti-PD-1 agonists consistently showed no enhancement of PD-1\PDL-1 binding (FIG. 3D).

Example 6

Functional Cell Assays, Inhibition of NFAT Activation in a THP-1/Jurkat-PD-1 Agonist Reporter Assay A THP-1/Jurkat PD1 NFAT co-culture assay was developed to assess the agonist activity of anti-PD1 antibodies generated from multiple campaigns. The THP-1 cell line was obtained from ATCC. The Jurkat reporter cell line was generated internally. The Jurkat reporter cells overexpress human PD-1 (hPD-1) on the cell surface and also express an NFAT-driven luciferase reporter to measure the activation status of the cells in response to stimulation. The Jurkat PD1 NFAT cells are activated with a CD3×CD33 BiTE in the presence of THP-1 cells. The anti-CD33 arm of the BiTE binds CD33 expressed on the THP-1 cells while the anti-CD3 arm binds the CD3 molecule on the Jurkat cells. The BiTE serves to engage the THP-1 and Jurkat cells resulting in the formation of an immune synapse between the two cells while activating the Jurkat cells. Activation of the Jurkat PD-1 NFAT cells is measured through the NFAT-driven luciferase reporter. This assay was run in the presence of anti-PD1 antibodies to identify agonist antibodies. Molecules that exhibited 20% or greater reduction in activation, as indicated by a loss of luciferase signal, were classified as agonist antibodies (Table 12). Anti-PD-1 antibodies 306E6 to 820C3 in Table 12 were on a mouse IgG1 backbone. Several of these antibodies were selected for additional profiling on a human IgG4Pro backbone (indicated as chimeric antibodies in Table 12).

TABLE 12

| Antibody | $IC_{50}$ Values (nM), inhibition of NFAT activity | Emax Values (%), inhibition of NFAT activity |
| --- | --- | --- |
| 306E6 | 1.14 | 45.5 |
| 307A3 | 1.03 | 42.6 |
| 313C12 | 0.37 | 42.2 |
| 414Al2 | 0.39 | 45.0 |
| 502H1 | 0.34 | 48.9 |
| 701C1 | 1.69 | 53.2 |
| 701E9 | 0.22 | 46.0 |
| 703D10 | 10.9 | 47.4 |
| 708E4 | 0.17 | 48.7 |
| 709A6 | 0.04 | 29.8 |
| 718C2 | 0.82 | 50.8 |
| 723C2 | 0.14 | 43.7 |
| 803E6 | 0.38 | 48.3 |
| 811G3 | 0.14 | 44.5 |
| 814E10 | 0.25 | 40.7 |
| 820C3 | 0.14 | 48.7 |
| Chimeric 718C2 | 0.38 | 44.4 |
| Chimeric 703D10 | 0.39 | 41.9 |
| Chimeric 723C2 | 0.13 | 42.6 |
| Chimeric 820C3 | 0.14 | 40.0 |

Example 7

Functional Cell Assays—Inhibition of IFNγ Production from Human PD-1 Knockin Splenocytes The primary cell assay used to select the top anti-PD1 antibodies was the hPD1 knock-in mouse splenocyte assay. Spleens were collected from C57BL/6 mice that express human PD1 in place of mouse PD1. Splenocytes were isolated from the spleens and activated with anti-CD3 (clone 2C11) at a concentration of 0.1 μg/ml. T cell activation was measured after 48 hours by quantitating mIFNγ levels by MSD analysis (Meso Scale Discovery). The assay was run in the presence of anti-PD1 antibodies selected from the THP-1/Jurkat PD1 NFAT screening assay. The top molecules identified from this assay were selected based on % inhibition of mIFNγ (50% or greater) and sequence clade. Inhibition and IC50 values are shown in Table 13.

TABLE 13

| Antibody | $IC_{50}$ Values (pM), Average, inhibition of IFNγ | Emax Values (%), Average, inhibition of IFNγ |
| --- | --- | --- |
| 306E6 | 22 | 19.5 |
| 703D10 | 3205 | 65 |
| 313C12 | 459 | 79 |
| 718C2 | 995 | 64.5 |
| 814E10 | 74.2 | 63 |
| 708E4 | 915 | 73.5 |
| 723C2 | 121.5 | 74 |
| 820C3 | 205 | 82 |

Example 8

Functional Cell Assays, Inhibition of IFNγ Production from Human PBMC Assay

The anti-PD-1 agonist antibodies were further characterized for their ability to modulate T cell functional activity, as measured by IFNγ production, in a human primary cell assay. PBMCs were isolated from human whole blood and activated with 1.5 pM of anti-CD3 (clone OKT3, BioLegend). T cell activation and function was assessed after 72 hours by quantitating hIFNγ levels by MSD analysis. Identified anti-PD-1 agonist antibodies were able to reduce IFNγ secretion compared to isotype control treated cells (Table 14A).

TABLE 14A

| Antibody | $IC_{50}$ Values (pM), Geomean, inhibition of IFNγ | Emax Values (%), Average, inhibition of IFNγ |
| --- | --- | --- |
| chimeric 723C2 in IgG4Pro | 18.0 | 66.5 |
| chimeric 820C3 in IgG4Pro | 38.5 | 56.7 |
| Antibody A | 7.4 | 49.0 |
| Antibody B | 18.4 | 48.9 |
| Antibody C | 17.7 | 46.8 |
| Antibody D | 18.0 | 50.1 |
| Antibody E | 8.1 | 47.8 |
| PD1AB-6-4P | 31.5 | 40.1 |

Antibody C, Antibody 1-4Pro, antibody PD1B1090-4Pro, antibody PD1B1094-4Pro, antibody ANB-030-4Pro and abatacept were also tested in this assay. The results are shown in Table 14B. Antibody C, the variable regions of Antibody 1-4Pro, antibody PD1B1090-4Pro, antibody PD1B1094-4Pro and antibody ANB-030-4Pro in a IgG1 wild-type backbone and in a IgG1 KO backbone, and abatacept were also tested in this assay. The results are shown in Table 14C summarized below. In each experiment, five donors were tested.

TABLE 14B

| Antibody | IC$_{50}$ Values (nM), Geomean, inhibition of IFNγ | Emax Values (%), Average, inhibition of IFNγ |
| --- | --- | --- |
| Antibody C | 0.03 | 59 |
| Antibody 1-4Pro | 0.01 | 55 |
| PD1B1090-4Pro | 0.79 | 72 |
| PD1B1094-4Pro | 0.46 | 64 |
| ANB-030-4Pro | 0.27 | 66 |
| Abatacept | 0.39 | 66 |

TABLE 14C

| Antibody | IC$_{50}$ Values (nM), Geomean, inhibition of IFNγ | Emax Values (%), Average, inhibition of IFNγ |
| --- | --- | --- |
| Antibody C | 0.03 | 59 |
| Antibody 1-IgG1WT | 0.01 | 46 |
| PD1B1090-IgG1WT | 0.07 | 83 |
| PD1B1094-IgG1WT | 0.12 | 79 |
| ANB-030-IgG1WT | 0.03 | 78 |
| abatacept | 0.39 | 66 |

The inhibition of IFNγ for the variable regions of Antibody 1-4Pro, antibody PD1B1090-4Pro, antibody PD1B1094-4Pro and antibody ANB-030-4Pro in a IgG1 KO backbone was less than 40% with IC$_{50}$ values above 30 nM.

Example 9

Functional Cell Assays, Inhibition of IL-17A Production from Th17-Monocyte Co-Culture Assay Anti-PD-1 agonist antibodies were tested for functional inhibition of IL-17 secretion by Th17 differentiated T cells. A primary cell co-culture assay was developed to assess modulation of IL-17 by PD-1. Human primary T cells isolated from PBMCs were Th17-differentiated under the following skewing conditions: CD4 T cells were stimulated with 0.5 µg/ml plate-bound anti-CD3 (clone UCHT1) for 4 days in Th17 skewing media (X-VIVO15 media+IL-1β (10 ng/mL), IL-23 (10 ng/mL), IL-6 (10 ng/mL), IL-2 (2 ng/mL), TGFβ (0.5 ng/mL), 5 µg/mL anti-IL4, 5 µg/mL anti-IFNγ). After 4 days, the cells were removed from the anti-CD3 coated plates and transferred to flasks containing Th17 skewing media. Following differentiation, Th17 cells were rested at least 3 days, then co-cultured with the autologous monocytes and re-stimulated with 40 fM anti-CD3 (clone OKT3) in the presence of the PD-1 antibodies. The co-culture system was required due to the Fc requirements necessary for the anti-PD-1 antibodies to demonstrate agonist activity. Inhibition of IL-17 was observed in this assay in the presence of anti-PD-1 agonist antibodies. Antibody IC$_{50}$ and maximum inhibition of the IL-17 response are shown in the table below (Table 15). Maximum inhibition was compared relative to an isotype control antibody.

TABLE 15

| Antibody | IC$_{50}$ Values (pM), Geomean, inhibition of IL-17A | Emax Values (%), Average, inhibition of IL-17A |
| --- | --- | --- |
| Chimeric 723C2 in IgG4Pro | 14.4 | 70.0 |
| Antibody A | 41.1 | 69.8 |
| Antibody B | 25.3 | 63.4 |
| Antibody C | 32.5 | 62.9 |
| Antibody D | 31.9 | 63.9 |
| Antibody E | 8.1 | 59.2 |
| PD1AB-6-4P | 175.8 | 67.5 |

Example 10

Functional Cell Assays, Inhibition of IL-21 Production from Tfh-Monocyte Co-Culture Assay An assay was developed to assess the ability of anti-PD-1 agonist antibodies to inhibit T follicular helper (Tfh) cell activity in vitro. CD4 T cells and autologous monocytes were obtained from ALLCELLS. T cells were skewed to the Tfh lineage by activating the cells with Dynabeads Human T-Activator CD3/CD28 (Gibco) in the presence of IL-23 (25 ng/ml) and TGFβ (5 ng/ml) for 5 days and then combined with autologous monocytes in the presence of 4.5 pM anti-CD3 (clone OKT3, BioLegend) and anti-PD-1 agonist antibodies after cells were washed and activation beads removed. 24 hours later, supernatants were collected and assayed for the presence of IL-21 (Meso Scale Discovery, MSD V-Plex Human IL-21 Kit). IL-21 production of restimulated Tfh-differentiated cells was inhibited by anti-PD-1 agonist antibodies. Representative IC50 and Emax inhibition values are shown in Table 16.

TABLE 16

| Antibody | IC$_{50}$ Values (pM), Geomean, inhibition of IL-21 | Emax Values (%), Average, inhibition of IL-21 |
| --- | --- | --- |
| Chimeric 723C2 in IgG4Pro | 12 | 85 |
| Antibody C | 6 | 84 |
| PD1AB-6-4P | 50 | 71 |

Example 11

Role of FcgR Interactions on PD-1 Agonist Activity

Figure 4A:
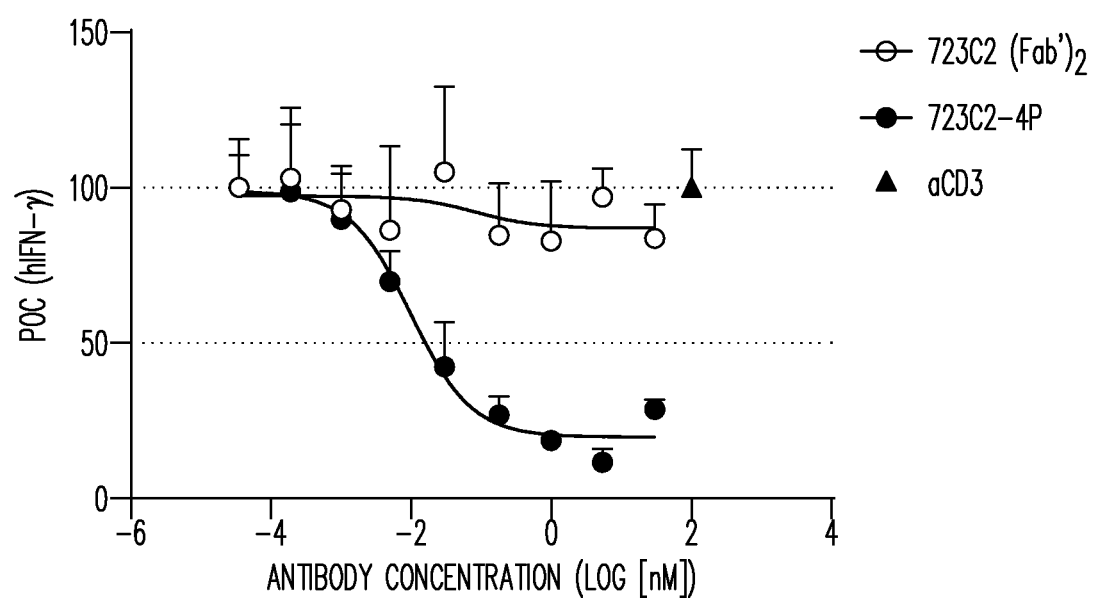
FIG. 4A, 4B: T cell functional activity in the presence of anti-PD-1 agonist antibody or F(ab')2 fragments derived from parental 723C2 agonist antibody (FIG. 4A) or parental agonist antibody 820C3 (FIG. 4B). POC stands for "percentage of control".
Figure 4B:
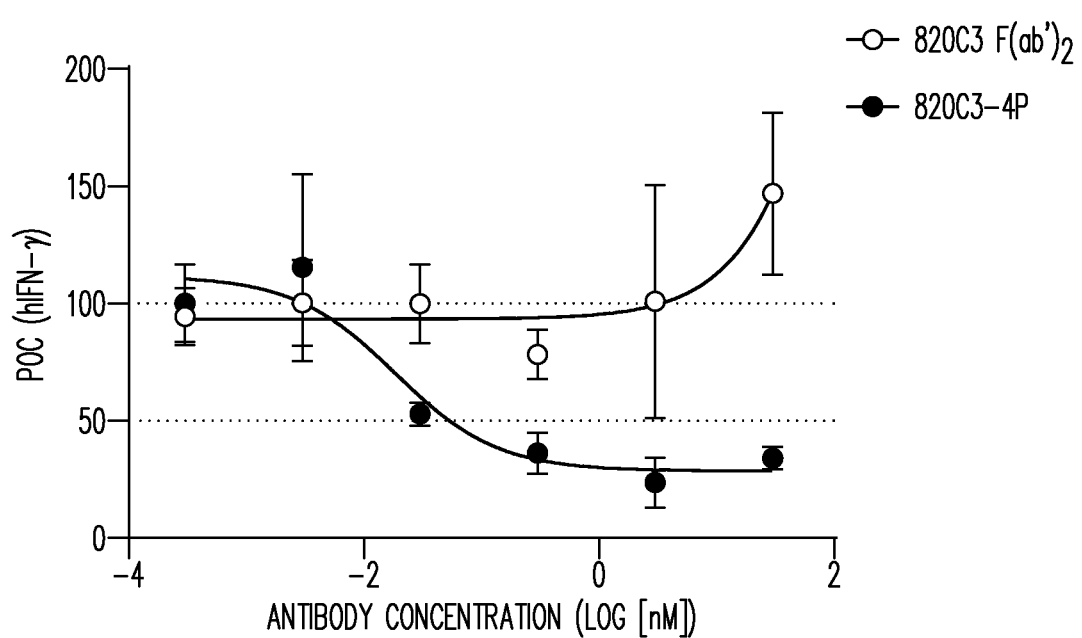

The role of Fc-Fcg receptor interactions on functional activity of the agonist antibodies was characterized by utilizing candidate anti PD-1 agonist antibodies on different backbone formats (IgG1 wild type, IgG1 KO, or IgG4 Pro) or divalent antibody fragments (F(ab')2 fragments). The functional activity of the antibody variants was evaluated by the ability to modulate IFNγ production from activated T cells in the human PBMC assay described above. Functional agonist activity, as measured by a reduction in IFNg production, is lost with the divalent F(ab')2 fragments of the parental 723C2 and 820C3 antibodies (FIGS. 4A and 4B). In contrast, the full-length antibody in a human IgG4Pro backbone inhibited IFNγ production in dose-dependent manner (FIGS. 4A and 4B, designated as 723C2-4P and 820C3-4P, respectively). In these assays, human PBMCs were isolated from whole blood and activated with 1.5 pM of anti-CD3 clone OKT3 in the presence of the anti-PD-1 antibody or the F(ab')2 fragment of the indicated anti-PD-1 antibody. After 72 hours, human IFN gamma cytokine levels in the supernatant were measured by MSD analysis.

As this suggested that Fc interactions are required for functional agonist activity of the anti-PD-1 antibody, the 723C2 antibody was generated on IgG1WT, IgG1 KO, and IgG4Pro backbones to further characterize these interactions (723-IgG1WT, 723-IgG1KO and 723-IgG4Pro, respectively, in Table 17 below). Both IgG1 WT and IgG4 Pro bind to human Fc receptors to differing degrees, while the IgG1 KO backbone has greatly reduced binding to Fc receptors. The anti-PD-1 agonist antibody on the IgG4 Pro demonstrated the highest degree of inhibition of IFNγ in the human PBMC assay, while the antibody on the IgG1 KO demonstrated greatly reduced activity (Table 17). Collectively, these data indicate that functional agonism of the anti-PD-1 antibody is dependent on Fc interactions.

TABLE 17

|  | % Inhibition IFNγ (mean, SD) | IC 50 (geomean (nM), SD) |
| --- | --- | --- |
| 723-IgG4Pro | 57 ± 17 | 0.03 ± 0.136 |
| 723-IgG1WT | 45 ± 16 | 0.015 ± 0.021 |
| 723-IgG1KO | 29 ± 17 | 0.02 ± 0.4 |

Example 12

In Vivo Model—Xenogeneic CD+ T Cell GvHD Model

An in vivo xenogeneic CD4+ T cell GvHD mouse model was used to test the efficacy of the PD-1 agonist antibodies. Eight NSG mice per group (NOD. Cg-Prkdc$^{scid}$Il2rg$^{tm1Wjl}$/SzJ, The Jackson Laboratory) were injected IV with 5×10$^6$ CD4+ T cells (purified by negative selection) from healthy donor leukopaks. Mice were dosed two times per week at 0.625 mg/kg IP according to the following; Group 1: 723 (IgG4-Pro), Group 2: PD1AB-6-4P (IgG4-Pro), Group 3: anti-TNP isotype (IgG4-Pro), Group 4: Avelumab (hIgG1-LALAPG), Group 5: anti-TNP isotype (hIgG1-LALAPG), Group 6: CTLA4-Ig (hIgG1-LALA). TNP is trinitrophenol. LALA represents the Leu234Ala/Leu235Ala mutations commonly used for disrupting antibody effector function. PG represents the Pro329Gly mutation, which eliminates effector function by preventing binding to Fc gamma receptors.

Three experimental repeats were run, each with a unique donor. By week four, significant inhibition of human cell accumulation was noted in Groups 1, 2 and 6 compared to their isotype-matched controls for all donors tested (Table 18). Quantification of inflammatory cytokines at week four showed a significant reduction in the levels of human IFNγ, TNFα, and IL-10 in all donors (Table 19). Human IL-1β, IL-2, IL-4, IL-6, IL-8, IL-12p70, and IL-13 were also tested, but all were below the limit of detection for the assay.

TABLE 18

HUMAN CD45+ CELL ACCUMULATION

| | % hCD45+ cells (mean ± SD) | | |
| --- | --- | --- | --- |
| | Donor 1 | Donor 2 | Donor 3 |
| Group 1 | 2.23 (2.83) | 3.52 (6.37) | 0.63 (0.68) |
| Group 2 | 14.86 (13.43) | 3.63 (3.12) | 1.31 (0.92) |
| Group 3 | 43.57 (18.33) | 21.92 (14.73) | 15.07 (14.48) |
| Group 4 | 40.70 (19.29) | 21.09 (9.41) | 24.70 (16.73) |
| Group 5 | 48.98 (17.87) | 25.22 (14.73) | 19.86 (3.95) |
| Group 6 | 3.24 (1.88) | 6.63 (5.50) | 1.76 (1.96) |

TABLE 19

HUMAN PLASMA CYTOKINE PRODUCTION

| | hIFNγ (pg/mL, mean ± SD) | | | hTNFα (pg/mL, mean ± SD) | | | hIL-10 (pg/mL, mean ± SD) | | |
| --- | --- | --- | --- | --- | --- | --- | --- | --- | --- |
| | Donor 1 | Donor 2 | Donor 3 | Donor 1 | Donor 2 | Donor 3 | Donor 1 | Donor 2 | Donor 3 |
| Group 1 | 331 (333) | 6616 (16780) | 372 (742) | 1 (1) | 8 (17) | 1 (1) | 1 (1) | 2 (5) | 0 (0) |
| Group 2 | 11475 (18275) | 2846 (3079) | 631 (606) | 9 (10) | 6 (4) | 1 (1) | 6 (8) | 1 (1) | 0 (0) |
| Group 3 | 40323 (36540) | 24450 (15273) | 11967 (9048) | 18 (7) | 43 (27) | 19 (13) | 12 (6) | 12 (6) | 4 (2) |
| Group 4 | 76077 (61582) | 28643 (12275) | 13302 (11700) | 29 (15) | 37 (15) | 19 (14) | 18 (7) | 10 (3) | 4 (3) |
| Group 5 | 39655 (48118) | 20180 (9671) | 15435 (10619) | 21 (9) | 34 (14) | 20 (9) | 16 (8) | 11 (7) | 4 (3) |
| Group 6 | 837 (1498) | 7163 (9580) | 871 (1907) | 1 (1) | 13 (15) | 3 (4) | 1 (1) | 8 (15) | 1 (1) |

Example 13

Pharmacokinetic Studies in Cynomolgus Monkey

Pharmacokinetics (PK) of Antibody C were assessed in male cynomolgus monkeys of Chinese origin following a single intravenous (IV) bolus dose of 0.1, 0.3 and 1.5 mg/kg or subcutaneous (SC) dose of 1.5 mg/kg (n=3 per group). Serum concentrations of Antibody C were determined using two different MSD immunoassay formats: (1) A "total" drug generic anti-human capture and detection assay and (2) A "free" drug assay with antigen (PD1-ECD) capture and anti-human detection. The PK profiles of both assays were superimposable, suggesting that endogenous sPD-1 did not interfere with the measurement of Antibody C and had little to no effect on TMDD. Antibody C demonstrated dose dependent CL (using both free and "total" assays), between 0.1 and 0.3 mg/kg suggestive of target mediated drug disposition (TMDD) contributions to overall clearance. The summary of NCA pharmacokinetic parameters for each of the respective doses is shown in Table 20 below.

TABLE 20

| Dose (mg/kg) | Route | CL (ml/d/kg) | Vc(ml/kg) | AUC (μg·h/ml) | $T_{1/2}$ (days) | MRT (days) | F % |
|---|---|---|---|---|---|---|---|
| 0.1 | i.v. | 14.3 | 35.6 | 171 | 2.9 | 4.1 | — |
| 0.3 | i.v. | 6.2 | 38.6 | 1,190 | 8.7 | 12.1 | — |
| 1.5 | i.v. | 3.0 | 33.9 | 12,400 | 18 | 25 | — |
| 1.5 | s.c. | — | — | 12,000 | — | 22.7 | 96.9 |

Example 14

Transfection and Production in CHO Cells and Biophysical Data

Transfection and Production in CHO Cells:

CHO-E cells are transfected at ~2×10E6 cells/mL in Irvine BalanCD Transfectory CHO+4 mM L-glutamine (or Glutamax). Amounts required for 1 L transfection are 0.15 mg of HC DNA plus 0.3 mg of LC DNA and 1.05 mg Filler DNA (Herring sperm) and 0.15 mg XBP1 DNA. The DNA is diluted in 100 mL of OptiPro SFM and sterile filtered through a 0.2 μm filter. 0.75 mL of Mirus TransIT Pro transfection reagent is added to the diluted DNA mixture and the DNA complex immediately added to the prepared CHO-E cells, and the shake flask returned to the 37° C., 5% CO2 shaker at 140 rpm. 24 hours post-transfection, temperature is shifted to 32° C., 2 mL of Gibco Anti-Clumping Agent and 100 ml Irvine Transfectory Supplement is added to the transfected cells. Five days post-transfection shaker temperature is shifted to 30° C. 200 mL of Irvine Transfectory Supplement is added between day 5 or day 7, depending on when glucose levels drops between 2 g/L-1 g/L. The transfected cultures is maintained for 10 days. Harvest is done by spinning down the cells, followed by sterile filtration through a 0.2 μm PES filter (Thermo Scientific).

After harvest, the clarified cell culture supernatants were sampled for titer by ForteBio/Pall Octet Red 96 instrument with Protein A biosensors as follows.

The titers for Antibody A, Antibody C, and Antibody E were between 18-38 mg/L, with about 80% recovery from protein purification, and more than 98% monomer after SEC purification. Proteins were buffer-exchanged in a final buffer containing 10 mM histidine-HCl, pH 6.0 and are stable at 4° C. for at least 4 months and with solubility up to 180 mg/ml in this buffer.

TABLE 21

| | Protein A Column | | | IEX Column | |
|---|---|---|---|---|---|
| | Titer (mg/L) | Yield (mg/L) | Recovery | Yield (mg/L) | Recovery |
| Antibody A | 22/18 | 25/21 | 114%/117% | 18/18 | 71%/83% |
| Antibody C | 23 | 22 | 95% | 18 | 83% |
| Antibody E | 38 | 38 | 100% | 31 | 80% |

TABLE 22

| | Quality | Stability | | Solubility |
|---|---|---|---|---|
| | SEC fresh (% M) | SEC 1 week at 40° C. (% M) | SEC 4 weeks at 40° C. (% M) | AUC at 180 mg/ml (% M) |
| Antibody A | 99.08 | 98.41 | 97.55 | 97.7 |
| Antibody C | 98.99 | 97.87 | 96.68 | 95.7 |
| Antibody E | 98.61 | 97.80 | 96.96 | 99.9 |

AUC: Analytical Ultracentrifugation as measured by the sedimentation velocity method at concentrations of 0.5-1 mg/ml; SEC: Size exclusion chromatography; % M: percent monomer.

Example 15

Bi-Specific Antibodies

Materials and Methods

Mouse antibodies and Reagents. anti-hPD1 (EH12.2H7) (Biolegend, 329912); Anti-hCD48 (Bio-gems, 10511-25-500); IgG1 (cat #16-4714-85), anti-hCD3 (OKT3) (16-0037-85), anti-hCD3 (UCHT1) (16-0038-85) and anti-CD11a (140011982) from eBiosciences; anti-hCD71 (Southern Biotech, 9670-14). aCD3/aCD28 human T-cell activator Dynabeads (Gibco, 11131 D)

Imagestream. Jurkat PD-1 cells were incubated in XVIVO 15 medium (Lonza) on ice for 10 minutes with AF-488 Cholera Toxin (Life Technologies, V-34403) and crosslinking antibody (Jackson ImmunoResearch) and either APC aCD3 (Biolegend, 317318), PV786 aPD-1 (Biolegend, 329930) or APC aCD48 (Sigma, SAB4700193). Cells were activated by transfer to pre-warmed X-VIVO 15 and allowed to incubate for an additional 12 minutes. Cell activation was stopped by addition of cold PBS-2% PFA (approximately 1:10 ratio, cells:PFA), and cells were incubated in fix solution for 20 minutes on ice. Cells were washed and resuspended in XVIVO and analyzed for cap formation and perimeter threshold using the Imagestream software.

Flow cytometry. $1\times10^5$ Jurkat, Jurkat-PD-1 or aCD3/aCD28-stimulated primary human T cells were incubated for 1 hr at 4° C. with 1 mg/ml of primary MAbs, or where bispecific molecules were tested, 8-point binding curves were generated from a starting concentration of 6.25 mg/ml and serially diluted 1:4. Cells were washed and stained for 1 hr at 4° C. with a 1:100 dilution of PE-anti-mouse Ig (Life Technologies, P852), or 1:800 dilution of PE-Goat anti-human F(ab')$_2$ (Invitrogen AHI1707), respectively. Samples were washed, fixed in 1× fix/lyse buffer (eBioscience, 00-5333-57) and analyzed on an LSR2 (BD)

PD-1 complementation assay. $2\times10^4$ Jurkat T cells over-expressing full-length PD-1-PK and intracellular full-length SHP1-EA fusion proteins were purchased from DiscoverX (DRX-BI-080515A) and cultured following manufacturer description. Cells were resuspended in cell plating media (DiscoverX, 93-0563R4B), and pre-incubated with primary mouse or human antibodies at 4° C. for 30 min. Depending of experiment, cells were additionally pre-incubated with 10 mM of pan-Src kinase inhibitor PP2 (Abcam, ab120308), or the inactive analog PP3 (Abcam, ab120617). Cells were washed and treated with or without crosslinking secondary goat anti-mouse IgG (Thermo Scientific, 31170). Cells were transferred to 384-white Opti-Plates (Perkin Elmer), received Flash Detection reagent (DiscoverX, 93-0247), and read in an EnVision Plate Reader (Perkin Elmer).

Primary huT cell activation. Primary human Pan-T cells (AllCells, PB009-1F) were labeled with 500 nM of Cell Trace Violet (Life technologies, cat #c34557). Epoxy-dynabeads M450 (Invitrogen, 14011) were covalently coated with 2.5 mg of mouse Abs/$10^7$ beads following manufacturer instructions. Cells were left unstimulated or were stimulated with plate bound anti-CD3 (UCHT1) (250 and 500 ng/mL) in the presence of Ab coated epoxy beads. Cells were harvested after 96 h, stained with BV510 anti-CD4 (BD, 562970) and PeCy7 anti-CD8 (BD, 335787) Abs, and cell proliferation was analyzed by Cell Trace Violet dilution in LSR2(BD). Primary memory $CD4^+/CD45RO^+$ T cells (AllCells, PB009-7F) were stimulated with 1 mg/well of plate bound anti-CD3 (UCHT1) in presence of 1 mg/well of plate bound isotype control (ISO) or BsAbs, respectively. Culture supernants were harvested at 72 h and analyzed for IL-2 and IL-10 secretion (MSD).

Figure 7A:
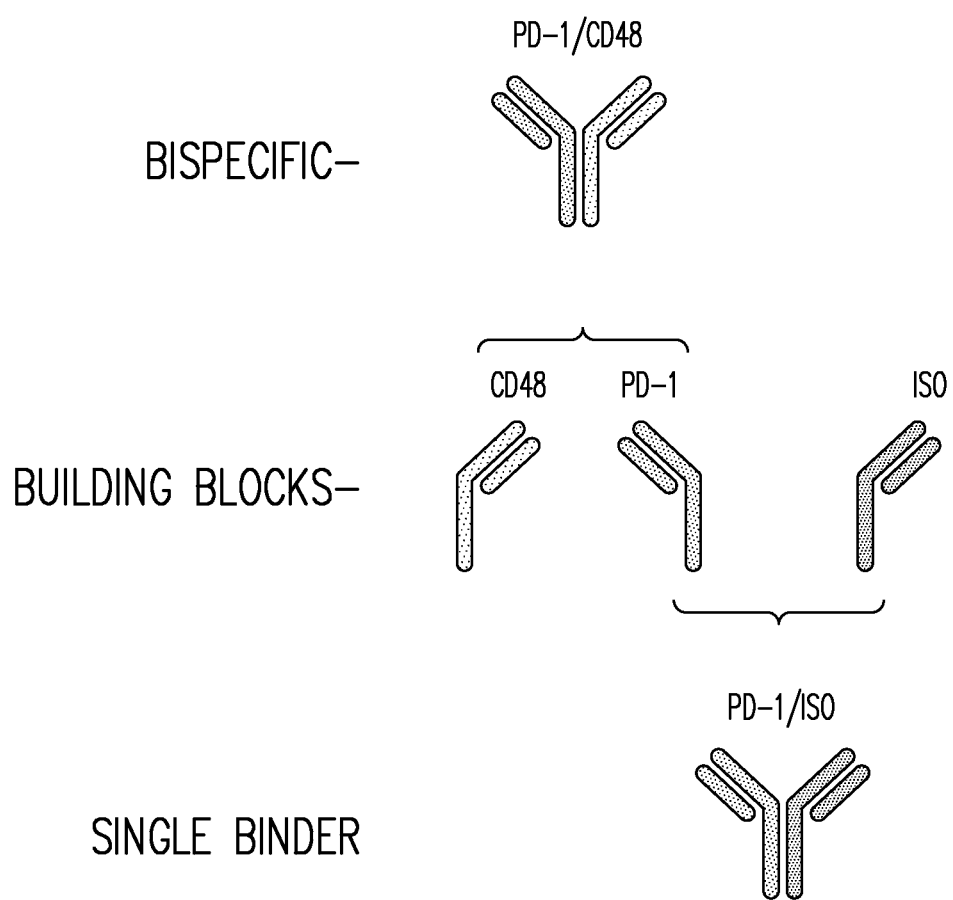
FIG. 7A, 7B, 7C: Bispecific constructs (FIG. 7A). Binding of each arm to PD-1 or CD48 demonstrated by flow cytometry on Jurkat cells overexpressing PD-1 (FIG. 7B). Stimulation of human memory CD4+ T (PD1$^+$) cells with plate-bound anti-CD3e in presence of plate-bound PD-1/CD48 BsAbs or control antibodies (FIG. 7C). MFI stands for "mean fluorescence intensity".

BsAbs generation and construct design. Bi-specific antibodies (BsAbs) were generated from published anti-CD48 (US2012/0076790) and anti-PD1 (WO 2011/110621AI) sequences that were used as building blocks. Bispecific constructs were designed with knob-into-hole technology to facilitate heterodimerization of two different target variable regions (IgG1-KO) to generate BsAbs containing anti-PD-1 and anti-CD48 (PD-1/CD48), or anti-PD-1 and anti-TNP as control (PD-1/ISO) (FIG. 7A). Variable-region sequences obtained for respective targets were cloned into pTT-5 (licensed from National Research Council Canada) expression vectors containing human constant regions. Briefly, variable region amino acid sequences were codon-optimized for mammalian expression. Light and heavy chains of the target V-gene were cloned into the same expression vector containing a joining linker segment. The vector was linearized by restriction-enzyme digest using EcoRI and NheI recognition sites. DNA sequences for variable regions were ordered as G-blocks (dsDNA) from Integrated DNA Technologies (IDTDNA) with overlapping homologous ends to the vector and adjoining linker segment. G-blocks were then joined via Gibson assembly method (NEBuilder HiFi kit, New England Biolabs, cat #E5510S) according to the manufacturer's protocol. Traditional cloning was then completed by transforming the assembly mixture into competent cells (NEB 5-alpha C2987, New England Biolabs) and then grown overnight at 37 C on LB agar plates with 100 µg/ml carbenicillin (Teknova). Individual colonies were picked and grown at 37 C overnight in LB media with carbenicillin. Positive clones for insert were confirmed by sequence analysis using Lasergene software package (DNAstar). Sequence-confirmed plasmid DNA was scaled-up in 0.5 L cultures and then purified via Plasmid Plus megaprep kit (Qiagen, cat #12981) according to the manufacturer's protocol.

CHO-E Transient Transfection. CHO-E cells are transfected at 2e6 cells/mL in FS-CHO supplemented with 2 mM Glutamine. For a 1 L mAb transfection volume, 1 mg light chain (LC) plasmid DNA and 0.5 mg heavy chain (HC) plasmid DNA are diluted in 100 mL of OptiPro SFM (Gibco) and sterile filtered through a 0.2 µm filter (Millipore). 1.5 mL of TransiT Pro (Mirus Bio LLC) transfection reagent is added and allowed to incubate for 15-30 minutes at room temperature. The complex is then added to the prepared CHO-E cells, and the shake flask returned to the shaker. 24 hours post transfection, 10 mL of Anti-Clumping Agent and 150 mL of CHO CD Efficient Feed B (both from Gibco) are added to the transfected cells and the temperature is shifted to 32° C. The transfected culture is maintained for 6-12 days and monitored routinely throughout the culture for cell growth, viability and nutrient consumption. Culture harvest is completed by centrifugation at 4700 rpm at 4° C., followed by sterile filtration.

BsAbs Purification. Load harvested culture supernatant onto 1 ml HiTrap MabSelect SuRe column from GE (Cat #11003493) pre-equilibrated with buffer A (DPBS, pH7.2) at 1.0 ml/min. Wash the columns with 10 ml each of buffer A, buffer B (DPBS plus 1.0 M NaCl) and buffer A again at 1 ml/min. Then, elute the bound proteins with 30 mM Sodium Acetate, pH3.5. Neutralize 5 ml fraction with 1% volume to volume of 3M Sodium Acetate, pH~9. The final buffer is 60 mM NaOAc, pH-5 after Protein A elution. The monomer percentage was 71% for PD1/ISO & 63% for PD1/CD48 by aSEC.

MabSelect Sure purified materials were further polished to remove aggregates by Cation exchange. Poros GoPure HS Pre-packed column from Thermo Fisher (Cat #4481316) was used for ion exchange. Load the Protein A sample onto a 1 ml Poros HS column pre-equilibrated with buffer A (60 mM NaOAc. pH 5.0) and wash the column with 10 column volume of buffer A. Then elute the bound proteins with a gradient from 0% to 40% of buffer B (60 mM NaOA, 1 M NaCl, pH 5.0) in 20 column volume at 0.5 ml/min. Pool fractions around peak and adjust salt concentration to 100 mM NaCl. Sterilely filter the samples with filtration units Measure protein concentration, determine endotoxin level and run SDS-PAGE as well as aSEC.

NFAT Luciferase assay. The Jurkat PD-1 NFAT reporter cell line was generated in-house. Human PD-1 from GeneCopoeia (EX-B0169-M02) was cloned into a vector which was transfected into the Jurkat cells (ATCC) via electroporation. The NFAT luciferase reporter (Promega E8481) was then transfected into PD-1 expressing clones via electroporation. The THP-1 cell line was purchased ATCC (TIB-202) and cultured following manufacturer instructions.

Jurkat PD-1 and NFAT reporter cells were re-suspended in assay media (RPMI, 2% HI-FBS), and $3 \times 10^4$ cells/condition were pre-incubated with doses of BsAbs (starting concentration of 100 nM and 1:3 dilutions) for 15 min in 384 flat-bottom Opti-Plates. THP-1 cells ($3 \times 10^4$ cells/condition) were added, and cells were stimulated with a 10 nM solution of aCD3xaCD33 activator for 6 h at 37° C. NFAT reporter was analyzed by addition of Steady-Glo® Luciferase Assay reagent form 15 min (Promega, E2520) and read in EnVision Plate Reader.

Results

CD48 and PD-1 crosslinking enhance PD-1 phosphorylation. CD48 is a well-established lipid raft- and IS-resident protein in mouse and human lymphocytes (Elishmereni and Levi-Schaffer, 2011). To better qualify the presence and abundance of CD48 in lipid rafts relative to that of PD-1 and CD3 we carried out ImageStream experiments to quantify at the single cell level the co-localization of these receptors with Cholera Toxin (CT)-induced lipid-raft coalescence (capping) in Jurkat cells overexpressing PD-1. Analysis of co-localization of CD48, CD3 and PD-1 within the lipid raft caps induced by CT was carried out using flurophore-labeled MAbs. This analysis showed that, unlike PD-1, CD3 and CD48 were readily observed within the capping induced by CT. Perimeter quantification, in which smaller perimeter values correlate with capping, revealed that after activation the capping of CD48 was evident, yet slightly less abundant than CD3. In contrast, PD-1 normally did not colocalize with CT, consistent with the hypothesis that PD-1 requires an active process (e.g. interaction with PDL-1) in order to be recruited to the lipid-raft enriched IS (Yokosuka et al., 2012).

Figure 5:
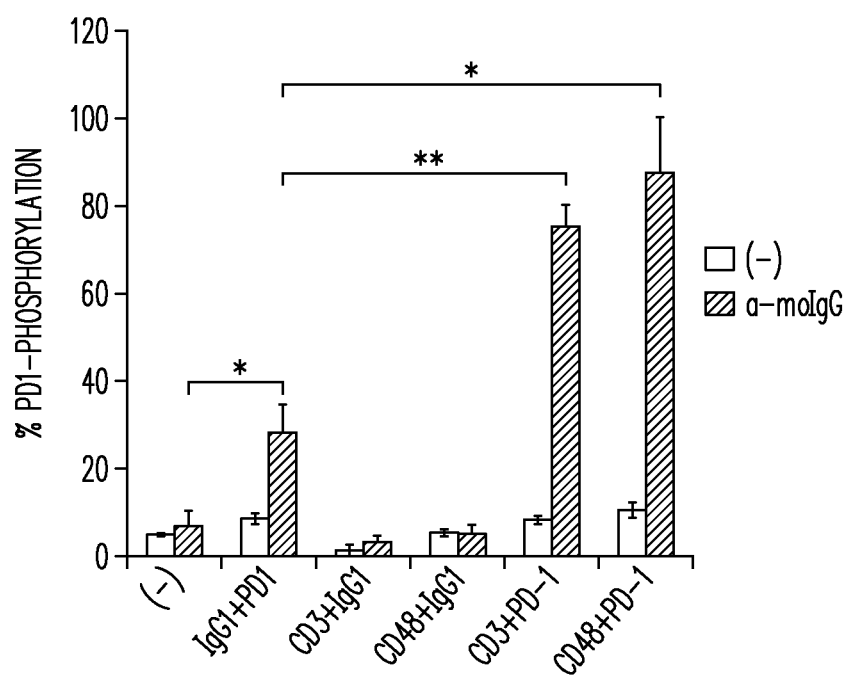
FIG. 5: Induction of PD-1 activation by a MAb against CD48 to upon crosslinking.

Presence of CD48 into lipid rafts and constitutive association with Src kinases (Lck in T cells), allowed us to hypothesized that, similar to CD3, approximation of CD48 with PD-1 will induce PD-1 activation/phosphorylation, as the canonical mechanism for PD-1 activation requires Lck-mediated phosphorylation of the intracellular ITSM and ITIM domains of PD-1 (Chemnitz et al., 2004; Parry et al., 2005; Sheppard et al., 2004). To test this hypothesis, a customized Jurkat cell line was generated to express human PD-1 fusion protein with one half of b-galactosidase (PK), and a cytosolic full-length SHP1 fusion protein with the complementary half of b-galactosidase (EA). PD-1 activation was thus measured as a function of PK/EA complementation due to recruitment of SHP1 to phosphorylated PD1, which produces a functional b-galactosidase. After confirming expression of PD-1, CD48 and CD3 in these cells, experiments were set up to evaluate the potential of a MAb against CD48 to induce PD-1 activation upon cross-linking (FIG. 5). PD-1 activation was not induced in the absence of PD-1 MAb or a Fc-specific secondary F(ab')2 antibody. Crosslinking with the secondary antibody induced PD-1 activation by ~3 fold; however, in the presence of CD48 or CD3 Mabs, PD-1 activation was enhanced by ~9 fold, indicating that close association of CD48 or CD3 with PD-1 can boost PD-1 activation. The low level of PD-1 activation induced by self-crosslinking was not surprising as studies have demonstrated that a small fraction of Lck is constitutively associated with PD-1 in T cells (Sheppard et al., 2004).

CD48-dependent activation of PD-1 requires Src-kinase activity. To determine whether the enhancement of PD-1 activation/phosphorylation by CD48 is dependent on Src kinase activity, crosslinking experiments were carried out in the presence of a pan-Src kinase inhibitor PP2, or the inactive analog PP3. Src-kinase inhibition abrogated PD-1 activation upon self-crosslinking or co-crosslinking with CD48, indicating that Lck activity is required for PD-1 activation. To further validate this concept, PD-1 activation was evaluated by crosslinking PD-1 with suboptimal amounts of anti-PD-1 in presence of antibodies against CD71, a receptor that does not migrate into lipid rafts or associate with Src-kinases (Schatzlmaier et al., 2015). Crosslinking of PD-1 with CD71 did not result in PD-1 activation, supporting the finding that translocation of PD-1 to an environment rich in activated Src kinases enables PD-1 phosphorylation and activation.

Figure 6:
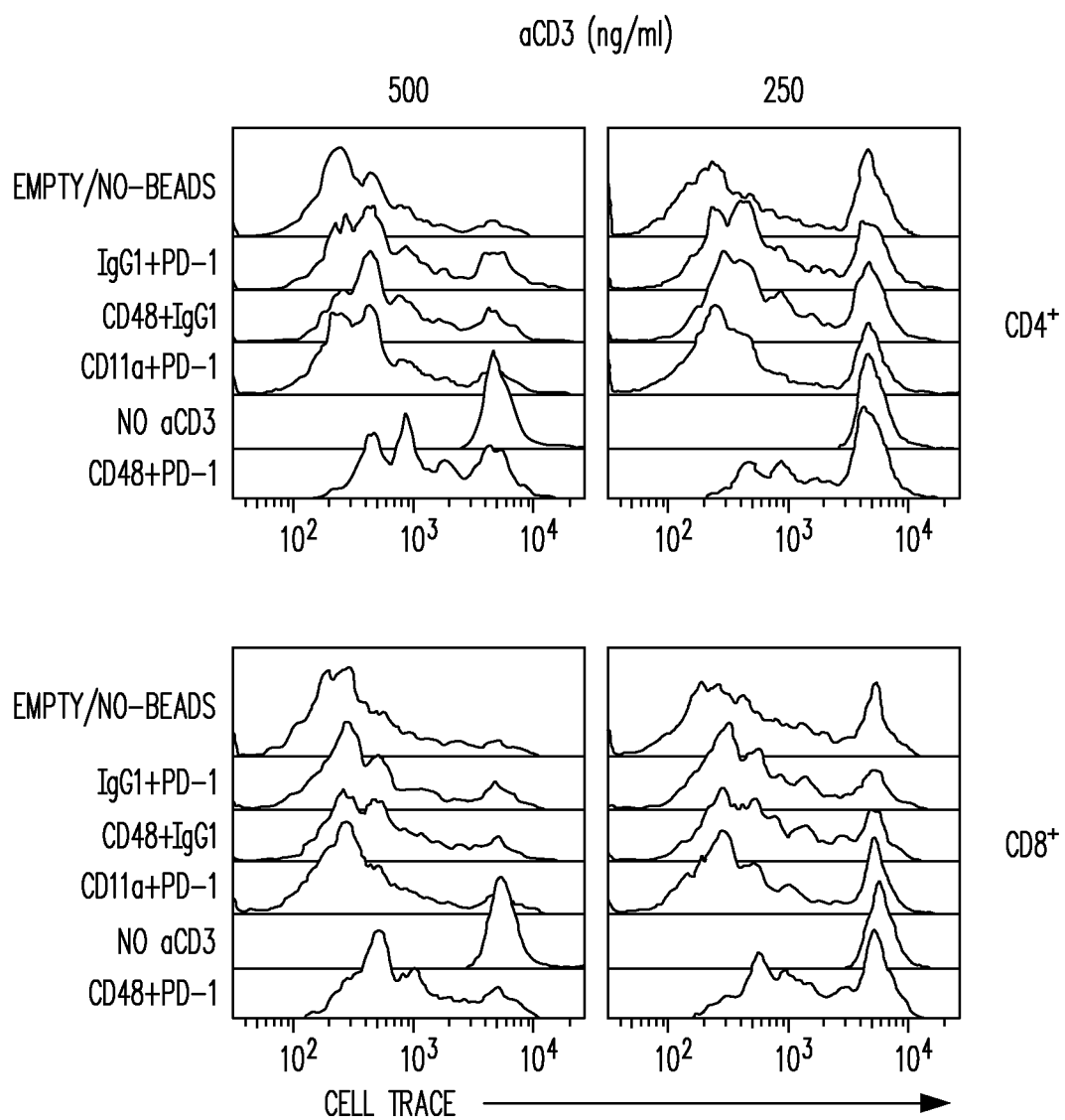
FIG. 6: Labeling of human pan-T cell with CellTrace-Violet, activation with CD3 MAbs, and analysis of cell proliferation by dilution of the CellTrace.

CD48-dependent PD-1 activation blunts AR-induced proliferation of primary human T cells. To functionally evaluate the ability of the CD48-dependent PD-1 activation to modulate T cell functions, magnetic beads were covalently co-coated with CD48, PD-1 MAbs, and isotype control, and tested on primary human T cells (CD4+ and CD8+) stimulated with plate bound anti-CD3. First, we confirmed expression of CD48 and PD-1 in pre-activated human $CD4^+$ and $CD8^+$ T lymphocytes. To evaluate the effect of the coated beads on cell activation, human pan-T cell were labeled with CellTrace-Violet, then activated with CD3 MAbs, and cell proliferation was analyzed by dilution of the CellTrace (FIG. 6). As shown in FIG. 6, beads co-coated with both CD48 and PD-1 MAbs were able to significantly reduce T cell proliferation relative to cells treated with beads coated with CD48 or PD-1 MAbs alone, and the inhibitory effect was more significant on $CD4^+$ than $CD8^+$ cells. As an additional control, we also tested beads co-coated with PD-1 and CD11a Mabs; the latter selected on the premise that CD11a is not a constitutively lipid-raft resident protein. As expected, PD-1 had no inhibitory function upon co-recruitment co-rectruiment with CD11a. These results further support the hypothesis that PD-1 activation by lipid-raft resident molecules (i.e. CD48) can effectively activate PD-1 to inhibit T cell expansion.

Figure 7B:
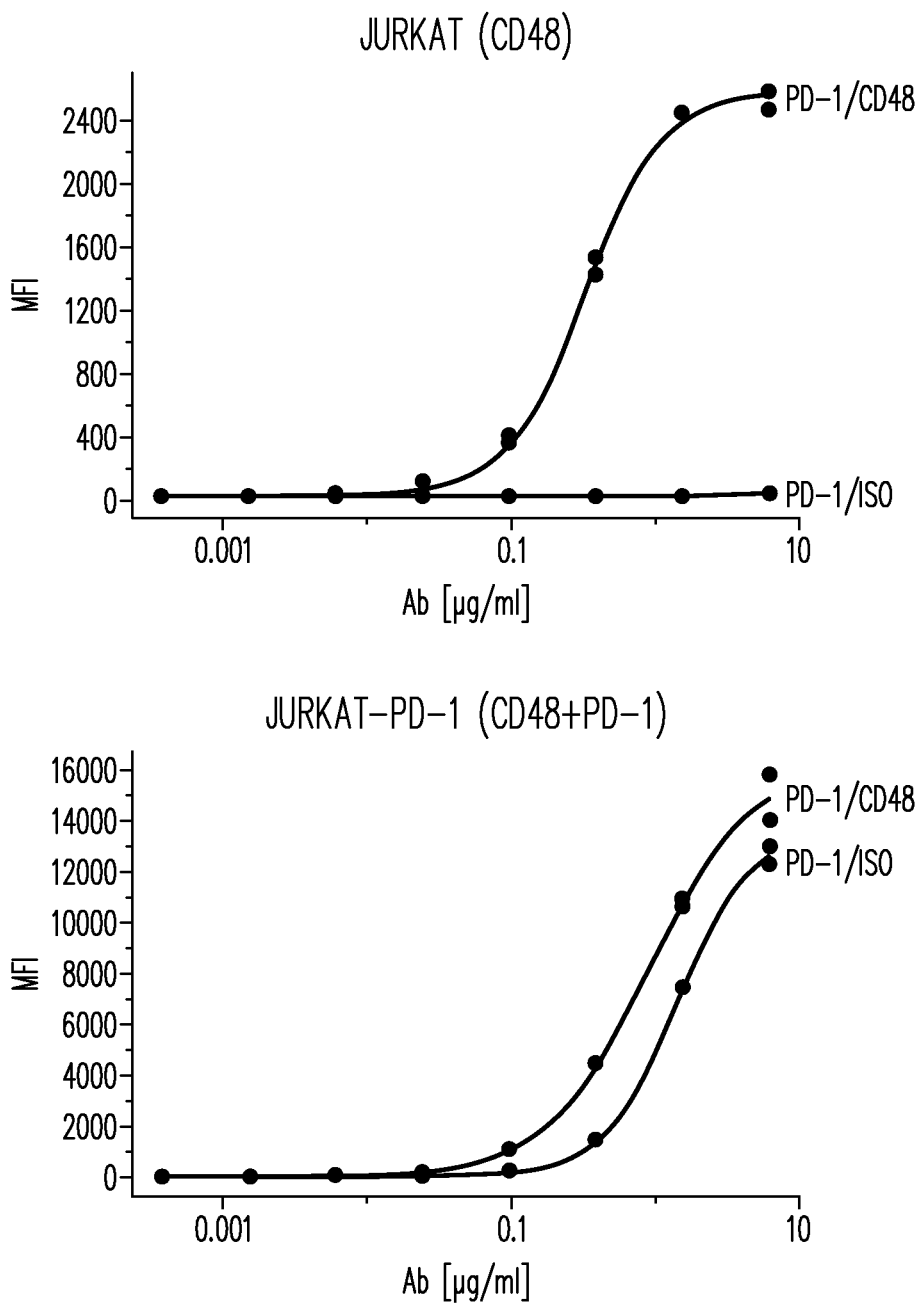
Figure 7C:
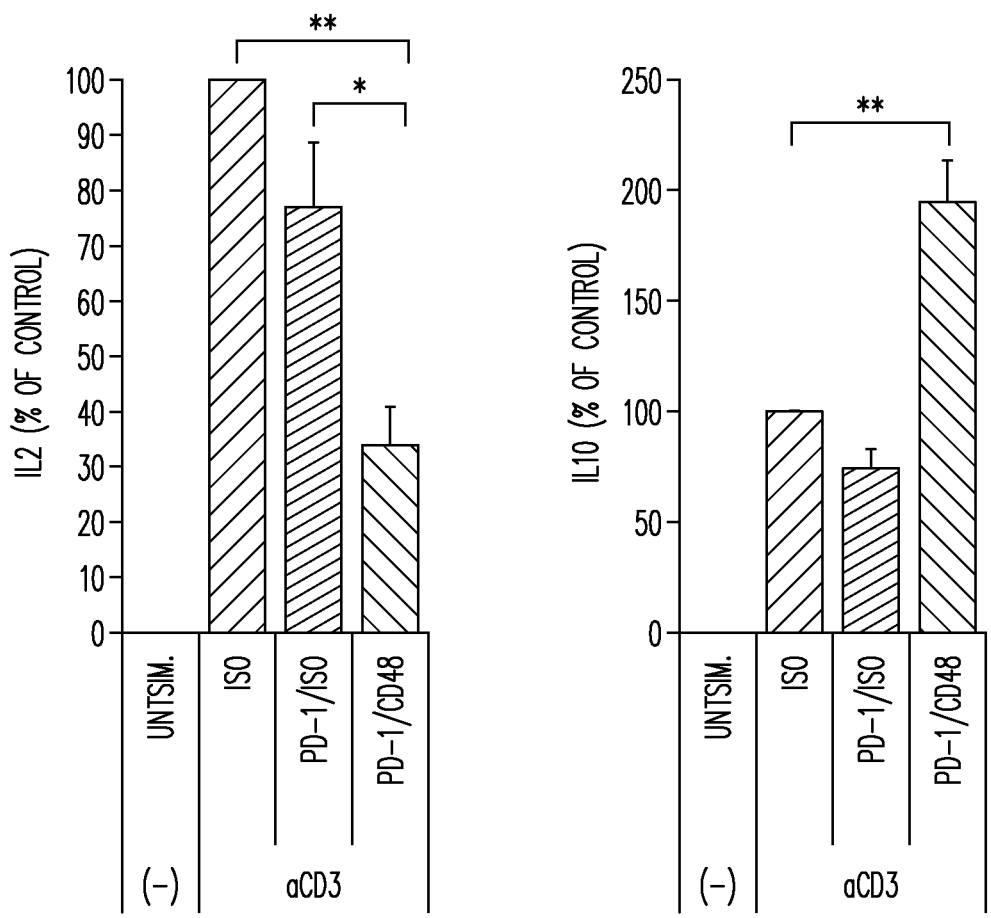

A bispecific antibody against PD-1 and CD48 induces PD-1 activation to modulate cytokine secretion and NFAT activation in AR-stimulated human T cells. The results obtained using separate monoclonal antibody-coated beads, prompted us to generate bispecific antibodies (BsAbs) in order to test the hypothesis that molecular localization of PD-1 with CD48 would provide an inhibitory signal on activated human T cells (FIG. 7A, 7B, 7C). Published antibodies were generated (agonistic anti-PD-1 antibody from patent application WO 2011/110621AI), and anti-CD48 Ab from US2012/0076790), and BsAbs were engineered as knob or hole single heavy/light chain constructs to generate BsAbs containing anti-PD-1 and anti-CD48 (PD-1/CD48), or anti-PD-1 and anti-TNP as control (PD-1/ISO) (FIG. 7A). Binding of each arm to PD-1 or CD48 was demonstrated by flow cytometry on Jurkat cells overexpressing PD-1 in order to detect both PD-1 and CD48 binding, or lacking PD-1 expression, to detect only CD48 binding (FIG. 7B). Using the Jurkat PD-1 complementation assay system described above, we demonstrated that PD-1/CD48 BsAb was ~3-fold more potent inducing PD-1activation than the PD-1/ISO control, confirming that PD-1/CD48 colocalization using this BsAb format results in enhanced PD-1 phosphorylation as well (FIG. 6). To evaluate the functional effect of the PD-1/CD48 BsAb, human memory CD4+T (PD1+) cells were stimulated with plate-bound anti-CD3e in presence of plate-bound PD-1/CD48 BsAbs or control antibodies, and analyzed for cytokine secretion (FIG. 7C). This analysis revealed an immunomodulatory effect of the PD-1/CD48 BsAb as it significantly reduced secretion of the pro-inflammatory cytokine IL2, but enhanced production of the anti-inflammatory cytokine IL-10. As IL-2 secretion requires NFAT transcriptional activation (Chow et al., 1999), the effect of the PD-1/CD48 BsAb on NFAT activation was evaluated in Jurkat T cells expressing both PD-1 and a NFAT-Luciferase reporter, and activated with anti-CD3e in presence of THP-1 cells for co-stimulation. This analysis showed that PD-1/CD48 BsAb was able to reduce the NFAT reporter >10-30% than control antibodies, and indicates that CD48-dependent activation of PD-1 is also to inhibit a key T cell effector transcriptional event leading to IL-2 production.

What is claimed is:

1. An anti-Programmed cell death 1 (PD-1) antibody or antigen-binding fragment thereof comprising:
   a heavy chain variable region comprising the amino acid sequence of SEQ ID NO: 43 (H-CDR1); the amino acid sequence of SEQ ID NO: 44 (H-CDR2); and the amino acid sequence of SEQ ID NO: 45 (H-CDR3), and
   a light chain variable region comprising the amino acid sequence of SEQ ID NO: 1 (L-CDR1); the amino acid sequence of SEQ ID NO: 2 (L-CDR2); and the amino acid sequence of SEQ ID NO: 3 (L-CDR3),
   or
   a heavy chain variable region comprising the amino acid sequence of SEQ ID NO: 43 (H-CDR1); the amino acid sequence of SEQ ID NO: 46 (H-CDR2); and the amino acid sequence of SEQ ID NO: 45 (H-CDR3), and
   a light chain variable region comprising the amino acid sequence of SEQ ID NO: 1 (L-CDR1); the amino acid sequence of SEQ ID NO: 2 (L-CDR2); and the amino acid sequence of SEQ ID NO: 3 (L-CDR3),
   or
   a heavy chain variable region comprising the amino acid sequence of SEQ ID NO: 47 (H-CDR1); the amino acid sequence of SEQ ID NO: 48 (H-CDR2); and the amino acid sequence of SEQ ID NO: 49 (H-CDR3), and
   a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3),
   or
   a heavy chain variable region comprising the amino acid sequence of SEQ ID NO: 50 (H-CDR1); the amino acid sequence of SEQ ID NO: 51 (H-CDR2); and the amino acid sequence of SEQ ID NO: 52 (H-CDR3), and
   a light chain variable region comprising the amino acid sequence of SEQ ID NO: 7 (L-CDR1); the amino acid sequence of SEQ ID NO: 8 (L-CDR2); and the amino acid sequence of SEQ ID NO: 9 (L-CDR3),
   or
   a heavy chain variable region comprising the amino acid sequence of SEQ ID NO: 53 (H-CDR1); the amino acid sequence of SEQ ID NO: 54 (H-CDR2); and the amino acid sequence of SEQ ID NO: 55 (H-CDR3), and
   a light chain variable region comprising the amino acid sequence of SEQ ID NO: 10 (L-CDR1); the amino acid sequence of SEQ ID NO: 11 (L-CDR2); and the amino acid sequence of SEQ ID NO: 12 (L-CDR3),
   or
   a heavy chain variable region comprising the amino acid sequence of SEQ ID NO: 56 (H-CDR1); the amino acid sequence of SEQ ID NO: 57 (H-CDR2); and the amino acid sequence of SEQ ID NO: 58 (H-CDR3), and
   a light chain variable region comprising the amino acid sequence of SEQ ID NO: 13 (L-CDR1); the amino acid sequence of SEQ ID NO: 14 (L-CDR2); and the amino acid sequence of SEQ ID NO: 15 (L-CDR3),
   or
   a heavy chain variable region comprising the amino acid sequence of SEQ ID NO: 59 (H-CDR1); the amino acid sequence of SEQ ID NO: 60 (H-CDR2); and the amino acid sequence of SEQ ID NO: 61 (H-CDR3), and
   a light chain variable region comprising the amino acid sequence of SEQ ID NO: 16 (L-CDR1); the amino acid sequence of SEQ ID NO: 17 (L-CDR2); and the amino acid sequence of SEQ ID NO: 18 (L-CDR3),
   or
   a heavy chain variable region comprising the amino acid sequence of SEQ ID NO: 62 (H-CDR1); the amino acid sequence of SEQ ID NO: 63 (H-CDR2); and the amino acid sequence of SEQ ID NO: 64 (H-CDR3), and
a light chain variable region comprising the amino acid sequence of SEQ ID NO: 19 (L-CDR1); the amino acid sequence of SEQ ID NO: 20 (L-CDR2); and the amino acid sequence of SEQ ID NO: 21 (L-CDR3),
or
a heavy chain variable region comprising the amino acid sequence of SEQ ID NO: 65 (H-CDR1); the amino acid sequence of SEQ ID NO: 66 (H-CDR2); and the amino acid sequence of SEQ ID NO: 67 (H-CDR3), and
a light chain variable region comprising the amino acid sequence of SEQ ID NO: 22 (L-CDR1); the amino acid sequence of SEQ ID NO: 23 (L-CDR2); and the amino acid sequence of SEQ ID NO: 24 (L-CDR3),
or
a heavy chain variable region comprising the amino acid sequence of SEQ ID NO: 68 (H-CDR1); the amino acid sequence of SEQ ID NO: 69 (H-CDR2); and the amino acid sequence of SEQ ID NO: 70 (H-CDR3), and
a light chain variable region comprising the amino acid sequence of SEQ ID NO: 25 (L-CDR1); the amino acid sequence of SEQ ID NO: 26 (L-CDR2); and the amino acid sequence of SEQ ID NO: 27 (L-CDR3),
or
a heavy chain variable region comprising the amino acid sequence of SEQ ID NO: 71 (H-CDR1); the amino acid sequence of SEQ ID NO: 72 (H-CDR2); and the amino acid sequence of SEQ ID NO: 58 (H-CDR3), and
a light chain variable region comprising the amino acid sequence of SEQ ID NO: 28 (L-CDR1); the amino acid sequence of SEQ ID NO: 14 (L-CDR2); and the amino acid sequence of SEQ ID NO: 29 (L-CDR3),
or
a heavy chain variable region comprising the amino acid sequence of SEQ ID NO: 73 (H-CDR1); the amino acid sequence of SEQ ID NO: 74 (H-CDR2); and the amino acid sequence of SEQ ID NO: 75 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3),
or
a heavy chain variable region comprising the amino acid sequence of SEQ ID NO: 80 (H-CDR1); the amino acid sequence of SEQ ID NO: 81 (H-CDR2); and the amino acid sequence of SEQ ID NO: 82 (H-CDR3), and
a light chain variable region comprising the amino acid sequence of SEQ ID NO: 33 (L-CDR1); the amino acid sequence of SEQ ID NO: 14 (L-CDR2); and the amino acid sequence of SEQ ID NO: 34 (L-CDR3),
or
a heavy chain variable region comprising the amino acid sequence of SEQ ID NO: 83 (H-CDR1); the amino acid sequence of SEQ ID NO: 84 (H-CDR2); and the amino acid sequence of SEQ ID NO: 85 (H-CDR3), and
a light chain variable region comprising the amino acid sequence of SEQ ID NO: 16 (L-CDR1); the amino acid sequence of SEQ ID NO: 35 (L-CDR2); and the amino acid sequence of SEQ ID NO: 36 (L-CDR3),
or
a heavy chain variable region comprising the amino acid sequence of SEQ ID NO: 86 (H-CDR1); the amino acid sequence of SEQ ID NO: 87 (H-CDR2); and the amino acid sequence of SEQ ID NO: 88 (H-CDR3), and
a light chain variable region comprising the amino acid sequence of SEQ ID NO: 37 (L-CDR1); the amino acid sequence of SEQ ID NO: 38 (L-CDR2); and the amino acid sequence of SEQ ID NO: 39 (L-CDR3), or
a heavy chain variable region comprising the amino acid sequence of SEQ ID NO: 89 (H-CDR1); the amino acid sequence of SEQ ID NO: 90 (H-CDR2); and the amino acid sequence of SEQ ID NO: 91 (H-CDR3), and
a light chain variable region comprising the amino acid sequence of SEQ ID NO: 40 (L-CDR1); the amino acid sequence of SEQ ID NO: 41 (L-CDR2); and the amino acid sequence of SEQ ID NO: 42 (L-CDR3).

2. The anti-PD-1 antibody or antigen-binding fragment thereof of claim 1 comprising:
a heavy chain variable region comprising the amino acid sequence of SEQ ID NO: 73 (H-CDR1); the amino acid sequence of SEQ ID NO: 74 (H-CDR2); and the amino acid sequence of SEQ ID NO: 75 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 30 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3).

3. The anti-PD-1 antibody or antigen-binding fragment thereof of claim 1, wherein said antibody or antigen-binding fragment thereof comprises a heavy chain variable region and a light chain variable region comprising the amino acid sequences of SEQ ID NO: 108 and SEQ ID NO: 92, respectively;
SEQ ID NO: 109 and SEQ ID NO: 93, respectively; SEQ ID NO: 110 and SEQ ID NO: 94, respectively; SEQ ID NO: 111 and SEQ ID NO: 95, respectively; SEQ ID NO: 112 and SEQ ID NO: 96, respectively; SEQ ID NO: 113 and SEQ ID NO: 97, respectively; SEQ ID NO: 114 and SEQ ID NO: 98, respectively; SEQ ID NO: 115 and SEQ ID NO: 99, respectively; SEQ ID NO: 116 and SEQ ID NO: 100, respectively; SEQ ID NO: 117 and SEQ ID NO: 101, respectively; SEQ ID NO: 118 and SEQ ID NO: 102, respectively; SEQ ID NO: 119 and SEQ ID NO: 103, respectively; SEQ ID NO: 120 and SEQ ID NO: 104, respectively; SEQ ID NO: 121 and SEQ ID NO: 105, respectively; SEQ ID NO: 122 and SEQ ID NO: 106, respectively; SEQ ID NO: 123 and SEQ ID NO: 107, respectively; SEQ ID NO: 131 and SEQ ID NO: 125, respectively; SEQ ID NO: 133 and SEQ ID NO: 127, respectively; SEQ ID NO: 135 and SEQ ID NO: 127, respectively; SEQ ID NO: 137 and SEQ ID NO: 129, respectively; or SEQ ID NO: 139 and SEQ ID NO: 129, respectively.

4. The anti-PD-1 antibody or antigen-binding fragment thereof of claim 1, wherein said antibody or antigen-binding fragment thereof comprises:
a heavy chain variable region and a light chain variable region having at least 90% identity to the amino acid sequences of SEQ ID NO: 131 and SEQ ID NO: 125, respectively;
a heavy chain variable region and a light chain variable region having at least 90% identity to the amino acid sequences of SEQ ID NO: 133 and SEQ ID NO: 127, respectively;
a heavy chain variable region and a light chain variable region having at least 90% identity to the amino acid sequences of SEQ ID NO: 135 and SEQ ID NO: 127, respectively;
a heavy chain variable region and a light chain variable region having at least 90% identity to the amino acid sequences of SEQ ID NO: 137 and SEQ ID NO: 129, respectively; or
a heavy chain variable region and a light chain variable region having at least 90% identity to the amino acid sequences of SEQ ID NO: 139 and SEQ ID NO: 129, respectively.

5. The anti-PD-1 antibody of claim 1, wherein said antibody comprises a heavy chain constant region selected from the group consisting of IgG1, IgG2, IgG3, IgG4, IgM, IgA and IgE constant regions.

6. The anti-PD-1 antibody of claim 5, wherein the heavy chain constant region is a heavy chain constant region of an IgG1.

7. The anti-PD-1 antibody of claim 5, wherein the heavy chain constant region is a heavy chain constant region of an IgG1 with a leucine to alanine mutation at a position corresponding to residue 235 of SEQ ID NO: 161 and at a position corresponding to residue 236 of SEQ ID NO: 161.

8. The anti-PD-1 antibody of claim 1, wherein the heavy chain constant region is a heavy chain constant region of an IgG4.

9. The anti-PD-1 antibody of claim 5, wherein the heavy chain constant region is a heavy chain constant region of an IgG4 with a serine to proline mutation at a position corresponding to residue 226 of SEQ ID NO: 143, SEQ ID NO: 147, SEQ ID NO: 149, SEQ ID NO: 153, or SEQ ID NO: 155.

10. The anti-PD-1 antibody or antigen-binding fragment thereof of claim 1, wherein the antibody or antigen-binding fragment thereof comprises a light chain constant region selected from the group consisting of kappa and lambda.

11. The anti-PD-1 antibody or antigen-binding fragment thereof of claim 1, wherein said antibody or antigen-binding fragment thereof is a humanized antibody or antigen-binding fragment thereof.

12. The anti-PD-1 antibody or antigen-binding fragment thereof of claim 1, wherein said antibody or antigen-binding fragment thereof is selected from the group consisting of a monoclonal antibody, a Fab, a F(ab')2, a Fv and an scFv.

13. The PD-1 antibody or antigen-binding fragment thereof of claim 1, wherein said antibody or antigen-binding fragment thereof is a monoclonal antibody.

14. A pharmaceutical composition comprising an anti-PD-1 antibody or antigen-binding fragment thereof of claim 1, and a pharmaceutically acceptable excipient.

15. An isolated polynucleotide encoding a heavy chain variable region and/or a light chain variable region of claim 3.

16. An expression vector comprising a polynucleotide according to claim 15.

17. An isolated host cell comprising an expression vector according to claim 16.

18. The isolated host cell of claim 17, wherein the cell is a mammalian cell.

19. A method of manufacturing an antibody comprising the steps of:
culturing an isolated host cell comprising an expression vector comprising an isolated polynucleotide encoding a heavy chain variable region according to claim 3 and an expression vector comprising an isolated polynucleotide encoding a light chain variable region according to claim 3 under conditions that allow formation of an antibody; and
recovering said antibody.

20. The method of claim 19, further comprising the step of purifying said antibody.

21. The method of claim 19, further comprising the step of formulating said antibody into a pharmaceutical composition.

22. An anti-PD-1 antibody or antigen-binding fragment thereof comprising a heavy chain variable region comprising the amino acid sequence of any one of SEQ NO: 131, SEQ NO: 133, SEQ NO: 135, SEQ NO: 137 or SEQ NO: 139 and a light chain variable region comprising the amino acid sequence of any one of SEQ NO: 125, SEQ NO: 127 or SEQ NO: 129.

23. An anti-PD-1 antibody or antigen-binding fragment thereof comprising:
a heavy chain variable region and a light chain variable region comprising the amino acid sequences of SEQ ID NO: 131 and SEQ ID NO: 125, respectively;
a heavy chain variable region and a light chain variable region comprising the amino acid sequences of SEQ ID NO: 133 and SEQ ID NO: 127, respectively;
a heavy chain variable region and a light chain variable region comprising the amino acid sequences of SEQ ID NO: 135 and SEQ ID NO: 127, respectively;
a heavy chain variable region and a light chain variable region comprising the amino acid sequences of SEQ ID NO: 137 and SEQ ID NO: 129, respectively; or
a heavy chain variable region and a light chain variable region comprising the amino acid sequences of SEQ ID NO: 139 and SEQ ID NO: 129, respectively.

24. The anti-PD-1 antibody of claim 23, wherein the heavy chain constant region is a heavy chain constant region of an IgG4.

25. The anti-PD-1 antibody of claim 23 comprising a heavy chain constant region of an IgG4 with a serine to proline mutation at a position corresponding to residue 226 of SEQ ID NO: 143, SEQ ID NO: 147, SEQ ID NO: 149, SEQ ID NO: 153, or SEQ ID NO: 155.

26. An isolated polynucleotide encoding a heavy chain variable region and/or a light chain variable region of claim 23.

27. An expression vector comprising a polynucleotide according to claim 26.

28. An isolated host cell comprising an expression vector according to claim 27.

29. The isolated host cell of claim 28, wherein the cell is a mammalian cell.

30. A method of manufacturing an antibody comprising the steps of:
culturing an isolated host cell comprising an expression vector comprising an isolated polynucleotide encoding a heavy chain variable region according to claim 23 and an expression vector comprising an isolated polynucleotide encoding a light chain variable region according to claim 23 under conditions that allow formation of an antibody; and
recovering said antibody.

31. An anti-PD-1 antibody comprising:
a heavy chain and a light chain comprising the amino acid sequences of SEQ ID NO: 143 and SEQ ID NO: 141, respectively;
a heavy chain and a light chain comprising the amino acid sequences of SEQ ID NO: 147 and SEQ ID NO: 145, respectively;
a heavy chain and a light chain comprising the amino acid sequences of SEQ ID NO: 149 and SEQ ID NO: 145, respectively;
a heavy chain and a light chain comprising the amino acid sequences of SEQ ID NO: 153 and SEQ ID NO: 151, respectively; or
a heavy chain and a light chain comprising the amino acid sequences of SEQ ID NO: 155 and SEQ ID NO: 151, respectively.

32. An isolated polynucleotide encoding a heavy chain and/or a light chain according to claim 31.

33. An expression vector comprising a polynucleotide according to claim 32.

34. An isolated host cell comprising an expression vector according to claim 33.

35. The isolated host cell of claim 34, wherein the cell is a mammalian cell.

36. A method of manufacturing an antibody comprising the steps of:
culturing an isolated host cell comprising an expression vector comprising an isolated polynucleotide encoding a heavy chain according to claim 31 and an expression vector comprising an isolated polynucleotide encoding a light chain according to claim 31 under conditions that allow formation of an antibody; and
recovering said antibody.

37. The method of claim 36, further comprising the step of purifying said antibody.

38. The method of claim 36, further comprising the step of formulating said antibody into a pharmaceutical composition.

39. An anti-PD-1 antibody or antigen-binding fragment thereof comprising:
a heavy chain variable region comprising the amino acid sequence of SEQ ID NO: 73 (H-CDR1); the amino acid sequence of SEQ ID NO: 76, SEQ ID NO: 78, or SEQ ID NO: 79 (H-CDR2); and the amino acid sequence of SEQ ID NO: 77 (H-CDR3), and
a light chain variable region comprising the amino acid sequence of SEQ ID NO: 164 or SEQ ID NO: 165 (L-CDR1); the amino acid sequence of SEQ ID NO: 31, SEQ ID NO: 166, or SEQ ID NO: 167 (L-CDR2); and the amino acid sequence of SEQ ID NO: 32 (L-CDR3).

40. An anti-PD-1 antibody or antigen-binding fragment thereof comprising:
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO:
73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3),
or
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3).

41. The anti-PD-1 antibody or antigen-binding fragment thereof of claim 40 comprising:
a heavy chain variable region comprising the amino acid sequence of SEQ ID NO: 73 (H-CDR1); the amino acid sequence of SEQ ID NO: 76 (H-CDR2); and the amino acid sequence of SEQ ID NO: 77 (H-CDR3), and
a light chain variable region comprising the amino acid sequence of SEQ ID NO: 164 (L-CDR1); the amino acid sequence of SEQ ID NO: 31 (L-CDR2); and the amino acid sequence of SEQ ID NO: 32 (L-CDR3).

42. The anti-PD-1 antibody or antigen-binding fragment thereof of claim 40 comprising:
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3).

43. The anti-PD-1 antibody or antigen-binding fragment thereof of claim 40 comprising:
a heavy chain variable region comprising the amino acid sequence of SEQ ID NO: 73 (H-CDR1); the amino acid sequence of SEQ ID NO: 78 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 166 (L-CDR2); and the amino acid sequence of SEQ ID NO: 32 (L-CDR3).

44. The anti-PD-1 antibody or antigen-binding fragment thereof of claim 40 comprising:
a heavy chain variable region comprising the amino acid sequence of SEQ ID NO: 73 (H-CDR1); the amino acid sequence of SEQ ID NO: 79 (H-CDR2); and the amino acid sequence of SEQ ID NO: 77 (H-CDR3), and
a light chain variable region comprising the amino acid sequence of SEQ ID NO: 165 (L-CDR1); the amino acid sequence of SEQ ID NO: 167 (L-CDR2); and the amino acid sequence of SEQ ID NO: 32 (L-CDR3).

45. The anti-PD-1 antibody of claim 40, wherein the heavy chain constant region is a heavy chain constant region of an IgG4.

46. The anti-PD-1 antibody of claim 40 comprising a heavy chain constant region of an IgG4 with a serine to proline mutation at a position corresponding to residue 226 of SEQ ID NO: 143, SEQ ID NO: 147, SEQ ID NO: 149, SEQ ID NO: 153, or SEQ ID NO: 155.

47. An anti-PD-1 antibody or antigen-binding fragment thereof, wherein said antibody or antigen-binding fragment thereof comprises a heavy chain variable region and a light chain variable region comprising the amino acid sequences of SEQ ID NO: 131 and SEQ ID NO: 125, respectively.

48. The anti-PD-1 antibody or antigen-binding fragment thereof of claim 47, wherein the heavy chain constant region is a heavy chain constant region of an IgG4.

49. An anti-PD-1 antibody or antigen-binding fragment thereof, wherein said antibody or antigen-binding fragment thereof comprises a heavy chain variable region and a light chain variable region comprising the amino acid sequences of SEQ ID NO: 133 and SEQ ID NO: 127, respectively.

50. The anti-PD-1 antibody or antigen-binding fragment thereof of claim 49, wherein the heavy chain constant region is a heavy chain constant region of an IgG4.

51. An anti-PD-1 antibody or antigen-binding fragment thereof, wherein said antibody or antigen-binding fragment thereof comprises a heavy chain variable region and a light chain variable region comprising the amino acid sequences of SEQ ID NO: 135 and SEQ ID NO: 127, respectively.

52. The anti-PD-1 antibody or antigen-binding fragment thereof of claim 51, wherein the heavy chain constant region is a heavy chain constant region of an IgG4.

53. An anti-PD-1 antibody or antigen-binding fragment thereof, wherein said antibody or antigen-binding fragment thereof comprises a heavy chain variable region and a light chain variable region comprising the amino acid sequences of SEQ ID NO: 137 and SEQ ID NO: 129, respectively.

54. The anti-PD-1 antibody or antigen-binding fragment thereof of claim 53, wherein the heavy chain constant region is a heavy chain constant region of an IgG4.

55. An anti-PD-1 antibody or antigen-binding fragment thereof, wherein said antibody or antigen-binding fragment thereof comprises a heavy chain variable region and a light chain variable region comprising the amino acid sequences of SEQ ID NO: 139 and SEQ ID NO: 129, respectively.

56. The anti-PD-1 antibody or antigen-binding fragment thereof of claim 55, wherein the heavy chain constant region is a heavy chain constant region of an IgG4.

57. An anti-PD-1 antibody comprising a heavy chain and a light chain comprising the amino acid sequences of SEQ ID NO: 143 and SEQ ID NO: 141, respectively.

58. A pharmaceutical composition comprising the anti-PD-1 antibody of claim 57 and a pharmaceutically acceptable excipient.

59. The anti-PD-1 antibody of claim 57, wherein the antibody consists of a heavy chain and a light chain consisting of the amino acid sequences of SEQ ID NO: 143 and SEQ ID NO: 141, respectively.

60. An isolated polynucleotide encoding a heavy chain and/or a light chain of claim 57.

61. An expression vector comprising a polynucleotide according to claim 60.

62. An isolated host cell comprising an expression vector according to claim 61.

63. An anti-PD-1 antibody comprising a heavy chain and a light chain comprising the amino acid sequences of SEQ ID NO: 147 and SEQ ID NO: 145, respectively.

64. A pharmaceutical composition comprising the anti-PD-1 antibody of claim 63 and a pharmaceutically acceptable excipient.

65. The anti-PD-1 antibody of claim 63, wherein the antibody consists of a heavy chain and a light chain consisting of the amino acid sequences of SEQ ID NO: 147 and SEQ ID NO: 145, respectively.

66. An isolated polynucleotide encoding a heavy chain and/or a light chain of claim 63.

67. An expression vector comprising a polynucleotide according to claim 66.

68. An isolated host cell comprising an expression vector according to claim 67.

69. An anti-PD-1 antibody comprising a heavy chain and a light chain comprising the amino acid sequences of SEQ ID NO: 149 and SEQ ID NO: 145, respectively.

70. A pharmaceutical composition comprising the anti-PD-1 antibody of claim 69 and a pharmaceutically acceptable excipient.

71. The anti-PD-1 antibody of claim 69, wherein the antibody consists of a heavy chain and a light chain consisting of the amino acid sequences of SEQ ID NO: 149 and SEQ ID NO: 145, respectively.

72. An isolated polynucleotide encoding a heavy chain and/or a light chain of claim 69.

73. An expression vector comprising a polynucleotide according to claim 72.

74. An isolated host cell comprising an expression vector according to claim 73.

75. An anti-PD-1 antibody comprising a heavy chain and a light chain comprising the amino acid sequences of SEQ ID NO: 153 and SEQ ID NO: 151, respectively.

76. A pharmaceutical composition comprising the anti-PD-1 antibody of claim 75 and a pharmaceutically acceptable excipient.

77. The anti-PD-1 antibody of claim 75, wherein the antibody consists of a heavy chain and a light chain consisting of the amino acid sequences of SEQ ID NO: 153 and SEQ ID NO: 151, respectively.

78. An isolated polynucleotide encoding a heavy chain and/or a light chain of claim 75.

79. An expression vector comprising a polynucleotide according to claim 78.

80. An isolated host cell comprising an expression vector according to claim 79.

81. An anti-PD-1 antibody comprising a heavy chain and a light chain comprising the amino acid sequences of SEQ ID NO: 155 and SEQ ID NO: 151, respectively.

82. A pharmaceutical composition comprising the anti-PD-1 antibody of claim 81 and a pharmaceutically acceptable excipient.

83. The anti-PD-1 antibody of claim 81, wherein the antibody consists of a heavy chain and a light chain consisting of the amino acid sequences of SEQ ID NO: 155 and SEQ ID NO: 151, respectively.

84. An isolated polynucleotide encoding a heavy chain and/or a light chain of claim 81.

85. An expression vector comprising a polynucleotide according to claim 84.

86. An isolated host cell comprising an expression vector according to claim 85.

* * * * *